(12) United States Patent
Bitner et al.

(10) Patent No.: US 9,464,072 B2
(45) Date of Patent: Oct. 11, 2016

(54) TREATMENT OF CENTRAL NERVOUS SYSTEM DISORDERS

(71) Applicant: AbbVie Inc., North Chicago, IL (US)

(72) Inventors: R. Scott Bitner, Pleasant Prairie, WI (US); Kaitlin E. Browman, Deerfield, IL (US); Michael E. Brune, Mundelein, IL (US); Yixian Long, Glenview, IL (US); Jurgen Dinges, Wadsworth, IL (US); Karla Drescher, Dossenheim (DE); Peer Jacobson, Libertyville, IL (US); Hwan-soo Jae, Glencoe, IL (US); Ravi Kurukulasuriya, Groton, CT (US); James T. Link, Stanford, CA (US); David J. Madar, Gilbert, AZ (US); Jyoti R. Patel, Libertyville, IL (US); Marina A. Pliushchev, Vernon Hills, IL (US); Jeffrey J. Rohde, Evanston, IL (US); Lynne E. Rueter, Round Lake Beach, IL (US); Qi Shuai, Dekalb, IL (US); Bryan K. Sorensen, Antioch, IL (US); Jiahong Wang, Lake Bluff, IL (US); Karsten M. Wicke, Altrip (DE); Martin Winn, Deerfield, IL (US); Dariusz Wodka, Monmouth Junction, NJ (US); Vince Yeh, LaJolla, CA (US); Hong Yong, Libertyville, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 14/569,203

(22) Filed: Dec. 12, 2014

(65) Prior Publication Data

US 2015/0099740 A1   Apr. 9, 2015

Related U.S. Application Data

(60) Division of application No. 13/554,698, filed on Jul. 20, 2012, now Pat. No. 8,940,902, which is a continuation of application No. 12/195,937, filed on Aug. 21, 2008, now abandoned, which is a continuation-in-part of application No. 11/697,044, filed on Apr. 5, 2007, now Pat. No. 7,435,833.

(60) Provisional application No. 60/790,141, filed on Apr. 7, 2006, provisional application No. 60/957,082, filed on Aug. 21, 2007.

(51) Int. Cl.

| | | |
|---|---|---|
| A61K 31/451 | (2006.01) | |
| A61K 31/4523 | (2006.01) | |
| A61K 31/55 | (2006.01) | |
| C07D 403/12 | (2006.01) | |
| A61K 31/44 | (2006.01) | |
| A61K 31/495 | (2006.01) | |
| C07D 207/267 | (2006.01) | |
| C07D 401/12 | (2006.01) | |
| C07D 401/14 | (2006.01) | |

(52) U.S. Cl.
CPC ............ *C07D 403/12* (2013.01); *A61K 31/44* (2013.01); *A61K 31/495* (2013.01); *C07D 207/267* (2013.01); *C07D 401/12* (2013.01); *C07D 401/14* (2013.01)

(58) Field of Classification Search
None
See application file for complete search history.

(56) References Cited

U.S. PATENT DOCUMENTS

| | | | |
|---|---|---|---|
| 4,273,704 A | 6/1981 | Mazur | |
| 4,324,791 A | 4/1982 | Welstead | |
| 4,514,332 A | 4/1985 | Hansen, Jr. et al. | |
| 4,751,292 A | 6/1988 | Fox | |
| 4,921,958 A | 5/1990 | Abou-Gharbia et al. | |
| 5,397,788 A | 3/1995 | Horwell et al. | |
| 5,622,983 A | 4/1997 | Horwell et al. | |
| 6,368,816 B2 | 4/2002 | Walker et al. | |
| 6,784,167 B2 | 8/2004 | Wood et al. | |
| 7,087,400 B2 | 8/2006 | Walker et al. | |
| 7,122,531 B2 | 10/2006 | Walker et al. | |
| 7,217,838 B2 | 5/2007 | Rohde et al. | |
| 7,435,833 B2 | 10/2008 | Yeh et al. | |
| 7,737,137 B2* | 6/2010 | Brune ................. | C07D 207/26 514/217.08 |
| 8,344,181 B2 | 1/2013 | Jaroskova et al. | |
| 2004/0122033 A1 | 6/2004 | Nargund et al. | |
| 2004/0133011 A1 | 7/2004 | Waddell et al. | |

(Continued)

FOREIGN PATENT DOCUMENTS

| | | |
|---|---|---|
| EP | 0215297 A2 | 3/1987 |
| EP | 0336356 A2 | 10/1989 |

(Continued)

OTHER PUBLICATIONS

Albrecht S., et al., "Nonpituitary Tumors of the Sellar Region" in: The Pituitary, Chapter 16, Melmed S., et al., eds., 2nd Edition, Blackwell Publishing, 2002, pp. 592-609.
Anstead G.M., "Steroids, Retinoids, and Wound Healing ," Advanced Wound Care, 1998, vol. 11, pp. 277-285.
Armaly M.F., et al., "Dexamethasone Ocular Hypertension and Eosinopenia, and Glucose Tolderance Test ," Archives of Ophthalmology, 1967, vol. 78, pp. 193-197.

(Continued)

*Primary Examiner* — Michael Barker
(74) *Attorney, Agent, or Firm* — Portia Chen

(57) ABSTRACT

A method for treating a patient suffering from disorders and deficits of the central nervous system associated with diabetes, associated with aging and neurodegeneration, comprising attention deficit disorder in general, attention deficit hyperactivity disorder (ADHD), Alzheimer's disease (AD), mild cognitive impairment, senile dementia, AIDS dementia, neurodegeneration, depression, and schizophrenia, comprising administering to a patient in need of such treatment an effective amount of a selective inhibitor of the 11-β-hydroxysteroid dehydrogenase Type 1 enzyme activity.

11 Claims, 9 Drawing Sheets

(56) References Cited

U.S. PATENT DOCUMENTS

| | | |
|---|---|---|
| 2005/0245534 A1 | 11/2005 | Link et al. |
| 2005/0261302 A1 | 11/2005 | Hoff et al. |
| 2005/0277647 A1 | 12/2005 | Link et al. |
| 2005/0288338 A1 | 12/2005 | Yao et al. |
| 2006/0004049 A1 | 1/2006 | Yao et al. |
| 2006/0009471 A1 | 1/2006 | Yao et al. |
| 2006/0009491 A1 | 1/2006 | Yao et al. |
| 2006/0079506 A1 | 4/2006 | Linders et al. |
| 2006/0089349 A1 | 4/2006 | Gundertofte et al. |
| 2006/0094699 A1 | 5/2006 | Kampen et al. |
| 2006/0100235 A1 | 5/2006 | Andersen et al. |
| 2006/0106008 A1 | 5/2006 | Andersen et al. |
| 2006/0106071 A1 | 5/2006 | Lin et al. |
| 2006/0111348 A1 | 5/2006 | Kampen et al. |
| 2006/0111366 A1 | 5/2006 | Andersen et al. |
| 2006/0149070 A1 | 7/2006 | Rohde et al. |
| 2006/0281773 A1 | 12/2006 | Patel et al. |
| 2007/0161641 A1 | 7/2007 | Hendrix et al. |

FOREIGN PATENT DOCUMENTS

| | | |
|---|---|---|
| EP | 405537 A1 | 1/1991 |
| EP | 0564924 A2 | 10/1993 |
| EP | 0697403 A1 | 2/1996 |
| EP | 1180513 A1 | 2/2002 |
| WO | WO-9113081 A1 | 9/1991 |
| WO | WO-9214697 A1 | 9/1992 |
| WO | WO-9428885 A1 | 12/1994 |
| WO | WO-9500146 A1 | 1/1995 |
| WO | WO-9902145 A1 | 1/1999 |
| WO | WO-0129007 A1 | 4/2001 |
| WO | WO-03059905 A1 | 7/2003 |
| WO | WO-03065983 A2 | 8/2003 |
| WO | WO-03075660 A1 | 9/2003 |
| WO | WO-2004011310 A1 | 2/2004 |
| WO | WO-2004033427 A1 | 4/2004 |
| WO | WO-2004037251 A1 | 5/2004 |
| WO | WO-2004056744 A1 | 7/2004 |
| WO | WO-2004056745 A2 | 7/2004 |
| WO | WO-2004065351 A1 | 8/2004 |
| WO | WO-2004089367 A1 | 10/2004 |
| WO | WO-2004089380 A2 | 10/2004 |
| WO | WO-2004089416 A2 | 10/2004 |
| WO | WO-2004089470 A2 | 10/2004 |
| WO | WO-2004089471 A2 | 10/2004 |
| WO | WO-2004089896 A1 | 10/2004 |
| WO | WO-2004113310 A1 | 12/2004 |
| WO | WO-2005016877 A2 | 2/2005 |
| WO | WO-2005041750 A2 | 5/2005 |
| WO | WO-2005042513 A1 | 5/2005 |
| WO | WO-2005046685 A1 | 5/2005 |
| WO | WO-2005047250 A1 | 5/2005 |
| WO | WO-2005060963 A1 | 7/2005 |
| WO | WO-2005097764 A1 | 10/2005 |
| WO | WO-2005103023 A1 | 11/2005 |
| WO | WO-2005108359 A1 | 11/2005 |
| WO | WO-2005108361 A1 | 11/2005 |
| WO | WO-2005116002 A2 | 12/2005 |
| WO | WO-2006002349 A1 | 1/2006 |
| WO | WO-2006002350 A1 | 1/2006 |
| WO | WO-2006002361 A2 | 1/2006 |
| WO | WO-2006012173 A1 | 2/2006 |
| WO | WO-2006012226 A2 | 2/2006 |
| WO | WO-2006012227 A2 | 2/2006 |
| WO | WO-2006012642 A2 | 2/2006 |
| WO | WO-2006017542 A1 | 2/2006 |
| WO | WO-2006020598 A2 | 2/2006 |
| WO | WO-2006024627 A2 | 3/2006 |
| WO | WO-2006024628 A1 | 3/2006 |
| WO | WO-2006040329 A1 | 4/2006 |
| WO | WO-2006048330 A1 | 5/2006 |
| WO | WO-2006048331 A1 | 5/2006 |
| WO | WO-2006048750 A2 | 5/2006 |
| WO | WO-2006049952 A1 | 5/2006 |
| WO | WO-2006050908 A1 | 5/2006 |
| WO | WO-2006053024 A2 | 5/2006 |
| WO | WO-2006066109 A2 | 6/2006 |
| WO | WO-2006104280 A1 | 10/2006 |

OTHER PUBLICATIONS

Baxter J.D., "Glucocorticoid Hormone Action ," Pharmacology and Therapeutics, 1976, vol. 2, pp. 605-659.

Becker K., "Inhibitors of the 11-beta-hydroxysteroid dehydrogenase type 1 enzyme," Prin. and Pract. of Endocrin. and Metabolism, 2001, pp. 723-738.

Beer H.D., et al., "Glucocorticoid-Regulated Gene Expression During Cutaneous Wound Repair ," Vitamins and Hormones, 2000, vol. 59, pp. 217-239.

Belanoff J.K., et al., "Corticosteroids and Cognition ," Journal of Psychiatric Research, 2001, vol. 35, pp. 127-145.

Bellows C.G., et al., "Osteoprogenitor Cells in Cell Populations Derived from Mouse and Rat Calvaria Differ in Their Response to Corticosterone, Cortisol, and Cortisone ," Bone, 1998, vol. 23 (2), pp. 119-125. Bennett J.C., Cecil Textbook of Medicine, 20th Edition, W.B. Saunders Company, 1996, vol. 2, pp. 1992-1996.

Bennett J.C., Cecil Textbook of Medicine, 20th Edition, W.B. Saunders Company, 1996, vol. 2, pp. 2050-2057.

Bertagna X, "Cushing's Disease," The Pituitary, 2002, pp. 496-612, Chap. 13 Sec. 3.

Billaudel B., et al., "Direct Effect of Corticostrone upon Insuline Secretion Studied by Three Different Techniques ," Hormone and Metabolic Research, 1979, vol. 11, pp. 555-560.

Billaudel B., et al., "Immediate in-Vivo Effect of Corticosterone on Glucose-Induced Insulin Secretion in the Rat ," Journal of Endocrinology, 1982, vol. 95, pp. 315-320.

Bland R., et al., "Characterization of 11.beta.-hydroxysteroid Dehydrongenase Activity and Corticosteroid Receptor Expression in Human Osterosarcoma Cell Lines ," Journal of Endocrinology, 1999, vol. 161, pp. 455-464.

Boscaro M., et al., "Cushing's Syndrome ," The Lancet, 2001, vol. 357, pp. 783-791.

Budziszewska B., "Effect of Antidepressant Drugs on the Hypothalamic-Pituitary-Adrenal Axis Activity and Glucocorticoid Receptor Function," Polish Journal of Pharmacology and Pharmacy , 2002, vol. 54, pp. 343-349.

Cooper M.S., et al., "Expression and Functional Consequences of 11.Beta.-Hydroxysteroid Dehydrogenase Activity in Human Bone," Bone, 2000, vol. 27 (3), pp. 375-381.

Cooper M.S., et al., "Modulation of 11β-Hydroxysteroid Dehydrogenase Enzymes by Proinflammatory Cytokines in Osteoblasts: An Autocrine Switch from Glucocorticoid Inactivation to Activation," Journal of Bone and Mineral Research, 2001, vol. 16 (6), pp. 1037-1044.

Cooper M.S., et al., "Osteoblastic 11.Beta.-Hydroxysteroid Dehydrogenase Type 1 Activity Increases With Age and Glucocorticoid Exposure," Journal of Bone and Mineral Research, 2002, vol. 17 (6), pp. 979-986.

Davani B., et al., "Type 1 11.Beta.-Hydroxysteroid Dehydrogenase Mediates Glucocorticoid Activation and Insulin Release in Pancreatic Islets," Journal of Biological Chemistry, 2000, vol. 275 (45), pp. 34841-34844.

De Quervain D.J., et al., "Glucocorticoid-Related Genetic Susceptibility for Alzheimers Disease," Human Molecular Genetics, 2004, vol. 13 (1), pp. 47-52.

Debattista C., et al., "The Use of Mifepristone in the Treatment of Neuropsychiatric Disorders," Trends in Endocrinology & Metabolism, 2006, vol. 17 (3), pp. 117-120.

FDA Mulls Drug to Slow Late-Stage Alzheimer's [online], [retrieved on Sep. 23, 2003]. Retrieved from the Internet:It; URL: http://www.cnn.com/2003/HEALTH/conditions/09/24/alzheimers.drug.ap/indexhtml>.

Gomez-Sanchez E.P., et al., "Central Hypertensinogenic Effects of Glycyrrhizic Acid and Carbenoxolone," American Journal of Physiology, 1992, vol. 263 (6 Pt 1), pp. E1125-E1130.

(56) References Cited

OTHER PUBLICATIONS

Good Man ,Gilman's., "The Pharmacological Basis of Therapeutics, seventh Edition MacMillan Publishing Company New York, NY," 1985.
Greene T.W., et al., in: Protective Groups in Organic Synthesis, 3rd Edition, John Wiley and Sons, Inc., 1999, Preface, Table of Contents, Abbreviations.
Greene T.W., et al., "Protection for the Amino group," Protective Groups in Organic Synthesis, 1999, Third Edition, pp. 494-653.
Hammami M.M., et al., "Regulation of 11β-Hydroxysteroid Dehydrogenase Activity in Human Skin Fibroblasts: Enzymatic Modulation of Glucocorticoid Action," Journal of Clinical Endocrinology & Metabolism, 1991, vol. 73 (2), pp. 326-334.
Han Z., et al., "Properly Designed Modular Asymmetric Synthesis for Enantiopure Sulfinamise Auxiliaries from N-Sulfonyl 1,2,3-oxathiazolidine-2-oxide Agents," Journal of American Chemical Society, 2002, vol. 124 (27), pp. 7880-7881.
Harris H.J., et al., "Intracellular Regeneration of Glucocorticoids by 11beta-Hydroxysteroid Dehydrogenase (11beta-Hsd)-1 Plays A Key Role in Regulation of The Hypothalamic-Pituitary-Adrenal Axis: Analysis of llbeta-Hsd-1-Deficient Mice," Endocrinology, 2001, vol. 142 (1), pp. 114-120.
Hermanowski-Vosatka A., et al., "11 beta-HSD1 Inhibition Ameliorates Metabolic Syndrome and Prevents Progression of Atherosclerosis in Mice," Journal of Experimental Medicine, 2005, vol. 202 (4), pp. 517-527.
Higuchi T., et al., eds., Pro-drugs as Novels Delivery Systems, vol. 14, ACS Symposium Series, Washington, D.C., 1975, Table of Contents.
Hodge G., et al., "Salt-Sensitive Hypertension Resulting from Nitric Oxide Synthase Inhibition is Associated with Loss of Regulation of Angiotensin II in the Rat," Experimental Physiology, 2002, vol. 87(1), pp. 1-8.
Hong F., et al., "Synthesis and Biological Studies of Novel Neurotensin (8-13) Mimetics," Bioorganic & Medicinal Chemistry, 2002, vol. 10 (12), pp. 3849-3858.
International Preliminary Report on Patentability and Written Opinion for Application No. PCT/US2006/000210, mailed on Jul. 10, 2007, 8 pages.
International Preliminary Report on Patentability and Written Opinion for Application No. PCT/US2006/000402, mailed on Jul. 10, 2007, 10 pages.
International Preliminary Report on Patentability and Written Opinion for Application No. PCT/US2007/066125, mailed on Oct. 8, 2008, 8 pages.
International Preliminary Report on Patentability and Written Opinion for Application No. PCT/US2008/073830, mailed on Feb. 24, 2010, 5 pages.
International Search Report for Application No. PCT/US2006/000210, mailed on Aug. 11, 2006, 4 pages.
International Search Report for Application No. PCT/US2006/000402, Mailed on Sep. 11, 2006, 5 pages.
International Search Report for Application No. PCT/US2007/066125, mailed on Sep. 21, 2007, 5 pages.
International Search Report for Application No. PCT/US2008/073830, mailed on Mar. 12, 2009, 3 pages.
Issa A.M., et al., "Hypothalamic-Pituitary-Adrenal Activity in Aged, Cognitively Impaired and Cognitively Unimpaired Rats," Journal of Neuroscience, 1990, vol. 10 (10), pp. 3247-3254.
Jones, C.D. et al., "Effects of Substituent Modification on Face Selection in Reduction," Journal of Organic Chemistry, 1998, vol. 63 (8), pp. 2758-2760.
Kerr D.S., et al., "Modulation of Hippocampal Long-Term Potentiation and Long-Term Depression by Corticosteroid Receptor Activation," Psychobiology, 1994, vol. 22 (2), pp. 123-133.
Kershaw E.E., et al., "Adipocyte-Specific Glucocorticoid Inactivation Protects Against Diet-Induced Obesity," Diabetes, 2005, vol. 54 (4), pp. 1023-1031.
Kim C.H., et al., "Effects of Dexamethasone on Proliferation, Activity, and Cytkine Secretion of Normal Human Bone Marrow Stromal Cells: Possible Mechanisms of Glucocorticoidinduced Bone Loss," Journal of Endocrinology, 1999, vol. 162 (3), pp. 371-379.
Kolocouris N., et al., "Synthesis and Antiviral Activity Evaluation of Some New Aminoadamantane Derivatives. 2," Journal of Medicinal Chemistry, 1996, vol. 39 (17), pp. 3307-3318.
Kornel L., et al., "Steroids Mechanism of the Effects of Glucocorticoids and mineralocorticoids on Vascular Smooth Muscle Contractility," Steroids, 1993, vol. 58 (12), pp. 580-587.
Kozlowski J.A., et al., "Substituted 2-(R)-Methyl Piperazines as Muscarinic M2 Selective Ligands," Bioorganic & Medicinal Chemistry Letters, 2002, vol. 12 (5), pp. 791-794.
Lakshmi V., et al., "Regional Distribution of 11 beta-Hydroxysteroid Dehydrogenase in Rat Brain," Endocrinology, 1991, vol. 128 (4), pp. 1741-1748.
Landfield P.W., et al., "Hippocampal Cell Death," Science, 1996, vol. 272 (5266), pp. 1249-1251.
Le Noble W.J., et al., "5-tert-Butyladamantan-2-one," Journal of Organic Chemistry, 1983, vol. 48 (7), pp. 1099-1101.
Lupien S., "Cortisol Levels during Human aging Predict Hippocampal Atrophy and Memory Deficits," Nature Neuroscience, 1998, vol. 1 (1), pp. 69-73.
Mason D., "Genetic Variation in the Stress Response: Susceptibility to Experimental Allergic Encephalomyelitis and Implications for Human Inflammatory Disease," Immunology Today, 1991, vol. 12 (2), pp. 57-60.
Masuzaki H., et al., "A Transgenic Model of Fisceral Obesity and the Metabolic Syndrome," Science, 2001, vol. 294, pp. 2166-2170.
Masuzaki H., et al., "Transgenic Amplification of Glucocorticoid Action in Adipose Tissue Causes High Blood Pressure in Mice," Journal of Clin Invest, 2003, vol. 112 (1), pp. 83-90.
McEwen B.S., "Glucocorticoids, Depression, and Mood Disorders: Structural Remodeling in the Brain," Metabolism—Clinical and Experimental, 2005, vol. 54 (5 Suppl), pp. 20-23.
Moisan M.P., et al., "11-beta-Hydroxysteroid Dehydrogenase Bioactivity and Messenger RNA Expression in Rat Forebrain: Localization in Hypothalamus, Hippocampus, and Cortex," Endocrinology, 1990, vol. 127 (3), pp. 1450-1455.
Monder C., et al., "11 P-Hydroxysteroid Dehydrogenase," Vitamins and Hormones, 1983, vol. 47, pp. 187-271.
Montague C.T., et al., "The Perils of Portliness: Causes and Consequences of Fisceral Adiposity," Diabetes, 2000, vol. 49 (6), pp. 883-888.
Morton N.M., et al., "Improved Lipid and Lipoprotein Profile, Hepatic Insulin Sensitivity, and Glucose Tolerance in 11.beta.-Hydroxysteroid Dehydrogenase Type 1 Null Mice," Journal of Biological Chemistry, 2001, vol. 276 (44), pp. 41293-41300.
Nagasawa H.T., et al., "Potential Latentiation Forms of Biologically Active Compounds Based on Action of Leucine Aminopeptidase. Dipeptide Derivatives of the Tricycloaliphatic Alpha-Amino Acid, Adamantanine," Journal of Medicinal Chemistry, 1975, vol. 18 (8), pp. 826-830.
Norman T.R., et al., "Emerging Treatments for Major Depression," Expert Review of Neurotherapeutics, 2007, vol. 7 (2), pp. 203-213.
Orstater H., et al., "Regulation of 11.Beta.-Hydroxysteroid Dehydrogenase Type 1 and Glucose-Stimulated Insulin Secretion in Pancreatic Islets of Langerhans," Diabetes/Metabolism Research and Reviews, 2005, vol. 21 (4), pp. 359-366.
Orth DN., "Cushing's Syndrome," The New England Journal of Medicine, 1995, vol. 332 (12), pp. 791-803.
Parks W.G., "Gordon Research Conferences: Program for 1966," Science, 1966, vol. 272, pp. 1249-1251.
Paterson J.M., et al., "Metabolic Syndrome without Obesity: Hepatic over Expression of 11.Beta.-Hydroxysteroid Dehydrogenase Type 1 in Transgenic Mice," The Proceedings of the National Academy of Sciences of the United States of America, 2004, vol. 101 (18), pp. 7088-7093.
Pirkle, "Use of Intercalative Effects to Enhance Enantioselectivity Chiral Stationary Phase Design," Journal of Chromatography, 1993, vol. 641, pp. 11-19.
Pirpiris M., "Hypertension Pressor Responsiveness in Corticosteroid-Induced Hypertension in Humans," Hypertension, 1992, vol. 19 (6 pt 1), pp. 567-574.

(56) References Cited

OTHER PUBLICATIONS

Rajan V., et al., "11 beta-Hydroxysteroid Dehydrogenase in Cultured Hippocampal Cells Reactivates Inert 11-dehydrocorticosterone, Potentiating Neurotoxicity," Journal of Neuroscience, 1996, vol. 16 (1), pp. 65-70.
Rauz S., et al., "Expression and Putative Role of 11.beta.-Hydroxysteroid Dehydrogenase Isozymes within the Human Eye," Investigative Ophthalmology & Visual Science, 2001, vol. 42 (9), pp. 2037-2042.
Rauz S., et al., "Inhibition of 11.beta.-Hydroxysteroid Dehydrogenase type 1 lowers Intraocular Pressure in Ptients with Ocular Hypertension," QJM Monthly Journal of the Associtaion of Physicians, 2003, vol. 96 (7), pp. 481-490.
Rehman Q., et al., "Effect of Glucocorticoids on Bone Density," Medical and Pediatric Oncology, 2003, vol. 41 (3), pp. 212-216.
Ringman, J.M.,, "What the Study of Persons at Risk for Familial Alzheimer's Disease Can Tell Us about the Earliest Stages of the disorder," Journal of Geriatric Psychiatry and Neurology, 2005, vol. 18, pp. 228-233.
Roche E.B., ed., Bioreversible Carries in Drug Design Theory and Application, Pergamon Press, 1987, Table of Contents.
Rook G.A., "Glucocorticoids and Immune Function," Baillieres Best Practice and Research Clinical Endocrinology Metabolism, 1999, vol. 13 (4), pp. 567-581.
Sakai R.R., et al., "Immunocytochemical Localization of 11 Beta-Hydroxysteroid Dehydrogenase in Hippocampus and Other Brain Regions of the Rat," Journal of Neuroendocrinology, 1992, vol. 4 (1), pp. 101-106.
Sandeep T.C., et al., "11Beta-hydroxysteroid Dehydrogenase Inhibition Improves Cognitive Function in Healthy Elderly Men and Type 2 Diabetics," Proceedings of the National Academy of Sciences, 2004, vol. 101 (17), pp. 6734-6739.
Schteingart D.E., "Cushing Syndrome," in: Principles and Practice of Endocrinology and Metabolism, 3rd Edition Chapter 75, Lippincott Williams & Wilkins, 2001, pp. 723-728.
Seckl J.R., et al., "11Beta-Hydroxysteroid Dehydrogenase Type 1-A Tissue Specific Amplifier of Glucocorticoid Action," Endocrinology Minireview, 2001, vol. 142, pp. 1371-1376.
Seckl J.R., et al., "The 11-beta Hydroxysteroid Dehydrogenase Inhibitor Glycyrrhetinic Acid Affects Corticosteroid Feedback Regulation of Hypothalamic Corticotrophin-releasing Peptides in Rats," Journal of Endocrinology, 1993, vol. 136 (3), pp. 471-477.
Small G.R., et al., "Preventing local regeneration of glucocorticoids by 11β-hydroxysteroid dehydrogenase type 1 enhances angiogenesis," Proceedings of the National Academy of Sciences, 2005, vol. 102 (34), pp. 12165-12170.
Stokes J., et al., "Altered Peripheral Sensitivity to Glucocorticoids in Primary Open-Angle Glaucoma," Investigative Ophthalmology & Visual Science, 2003, vol. 44 (12), pp. 5163-5167.
Strohle A., et al., "Stress Responsive Neurohormones in Depression and Anxiety," Pharmacopsychiatry, 2003, vol. 36 suppl, pp. S207-S214.
Tadayyon M., "Insulin Sensitization in the Treatment of Type 2 Diabetes," Expert Opinion on Investigational Drugs, 2003, vol. 12 (3), pp. 307-324.
Tronche F., et al., "Disruption of the Glucocorticoid Receptor Gene in the Nervous System Results in Reduced Anxiety," Nature Genetics, 1999, vol. 23 (1), pp. 99-103.
Turner R.T., et al., "Prednisone Inhibits Formation of Cortical Bone in Sham-Operated and Ovariectomized Female Rats," Calcified Tissue International, 1995, vol. 56, pp. 311-315.
Vaidyanathan G., et al., "Decarboxylation of 1-Aminocyclopropanecarboxylic Acid and Its Derivatives," Journal Organic Chemistry, 1989, vol. 54, pp. 1810-1815.
Walker B.R., et al., "Carbenoxolone Increases Hepatic Insulin Sensitivity in Man: A Novel Role for 11-0xosteroid Reductase in Enhancing Glucocorticoid Receptor Activation," The Journal of Clinical Endocrinology and Metabolism, 1995, vol. 80 (11), pp. 3155-3159.
Walker B.R., et al., "Corticosteroids and Vascular Tone: Mapping the Messenger Maze," Clinical Science, 1992, vol. 82 (6), pp. 597-605.
Wolkowitz O.M., et al., "The Steroid Dementia Syndrome: An Unrecognized Complication of Glucocorticoid Treatment," Annalsof the New York Academy of Sciences, 2004, vol. 1032, pp. 191-194.
Woolley C.S., et al., "Exposure to Excess Glucocorticoids Alters Dendritic Morphology of Adult Hippocampal Pyramidal Neurons," Brain Research, 1990, vol. 531, pp. 225-231.
Yau J.L., et al., "Glucocorticoids, Hippocampal Corticosteroid Receptor Gene Expression and Antidepressant Treatment: Relationship with Spatial learning in Young and Aged Rats," Neuroscience, 1995, vol. 66 (3), pp. 571-581.
Yau J.L., et al., "Lack of Tissue Glucocorticoid Reactivation in 11.Beta.-Hydroxysteroid Dehydrogenase Type 1 Knockout Mice Ameliorates Age-Related Learning Impairments," Proceedings of National Academy of Sciences, 2001, vol. 98 (8), pp. 4716-4721.
Yeh V.S., et al., "A Highly Efficient Synthesis of Potent and Selective Butyrolactam Inhibitors of L1beta-Hsd1," Organic Letters, 2006, vol. 8 (18), pp. 3963-3966.
Yeh V.S., et al., "Discovery of Orally Active Butyrolactam L1beta-Hsd1 Inhibitors," Bioorganic and Medicinal Chemistry Letters, 2006, vol. 16 (21), pp. 5555-5560.
Ziegler F.E., et al. , "Substitution Reactions of Specifically ortho-Metalated Piperonal Cyclohexylimine," Journal of Organic Chemistry, 1976, vol. 41 (9), pp. 1564-1566.

* cited by examiner

Effects of Compound C at 30 mg/kg, po, on acetylcholine release in rat prefrontal cortex in rats transferred from home cage to novel cage and back to home cage.

Effects of Compound C at 30 mg/kg, po,. on acetylcholine release in rat hippocampus in rats transferred from home cage to novel cage and back to home cage.

Effects of Compound C at 30 mg/kg, po,. on acetylcholine release in rat prefrontal cortex and hippocampus under resting conditions Data means ± SEM percentage change of the average of two pre-application basal levels Data are means ± SEM are under the curve $AUC_{0-240}$ minutes arbitrary units.

TREATMENT OF CENTRAL NERVOUS SYSTEM DISORDERS

CROSS-REFERENCE TO RELATED APPLICATIONS

This is a divisional of U.S. patent application Ser. No. 13/554,698, filed on Jul. 20, 2012, which is a continuation of U.S. patent application Ser. No. 12/195,937, filed on Aug. 21, 2008, which is a continuation-in-part of U.S. patent application Ser. No. 11/697,044, filed on Apr. 5, 2007, now U.S. Pat. No. 7,435,833, which claims priority to U.S. Patent Application No. 60/790,141, filed on Apr. 7, 2006; U.S. patent application Ser. No. 12/195,937 also claims priority to U.S. Patent Application No. 60/957,082, filed on Aug. 21, 2007, the entire contents of all of which are fully incorporated herein by reference.

TECHNICAL FIELD AND BACKGROUND

The present invention relates to a treatment of central nervous system disorders, cognitive deficits and dementias associated with a diversity of conditions, including age-related or glucocorticoid-related declines in cognitive function such as those seen in Alzheimer's and associated dementias, major depressive disorder, psychotic depression, anxiety, panic disorder, post traumatic stress disorder, depression in Cushing's syndrome, and treatment resistant depression, using 11β-HSD1 inhibitors.

11-β-hydroxysteroid dehydrogenase Type 1 enzyme (11β-HSD-1) is a low affinity enzyme with $K_m$ for cortisone in the micromolar range that prefers NADPH/NADP$^+$ (nicotinamide adenine dinucleotide phosphate) as cofactors. 11β-HSD-1 is widely expressed and particularly high expression levels are found in liver, brain, lung, adipose tissue, and vascular smooth muscle cells. In vitro studies indicate that 11β-HSD-1 is capable of acting both as a reductase and a dehydrogenase. However, many studies have shown that it functions primarily as a reductase in vivo and in intact cells. It converts inactive 11-ketoglucocorticoids (i.e., cortisone or dehydrocorticosterone) to active 11-hydroxyglucocorticoids (i.e., cortisol or corticosterone), and thereby amplifies glucocorticoid action in a tissue-specific manner.

11β-HSD-1 is expressed in mammalian brain, and published data indicates that elevated levels of glucocorticoids may cause neuronal degeneration and dysfunction, particularly in the aged (de Quervain et al.; Hum Mol Genet. Vol. 13 pages 47-52, 2004; Belanoff et al. J. Psychiatr Res. Vol. 35, pages 127-35, 2001). Evidence in rodents and humans suggests that prolonged elevation of plasma glucocorticoid levels impairs cognitive function that becomes more profound with aging. (See, A. M. Issa et al., J. Neurosci. Vol. 10, pages 3247-3254, 1990; S. J. Lupien et. al., Nat. Neurosci., Vol. 1, pages 69-73, 1998; J. L. Yau et al. Neuroscience, Vol. 66, pages 571-581, 1995). Chronic excessive cortisol levels in the brain may result in neuronal loss and neuronal dysfunction. (See, D. S. Kerr et al., Psychobiology, Vol. 22 pages 123-133, 1994, C. Woolley, Brain Res. Vol. 531 pages 225-231, 1990, P. W. Landfield, Science, Vol. 272 pages 1249-1251, 1996). Furthermore, glucocorticoid-induced acute psychosis exemplifies a more pharmacological induction of this response, and is of major concern to physicians when treating patients with these steroidal agents (Wolkowitz et al.; Ann NY Acad Sci. Vol. 1032 pages 191-194, 2004). It has been recently shown that 11β-HSD-1 mRNA is expressed in human hippocampus, frontal cortex and cerebellum, and that treatment of elderly diabetic individuals with the non-selective 11β-HSD-1 and 11β-HSD-2 inhibitor carbenoxolone improved verbal fluency and memory (Thekkapat et al., Proc Natl Acad Sci USA. Vol. 101, pages 6743-6749, 2004). Excessive glucocorticoid levels also affects psychopathology, as shown in animal models, it leads to increased anxiety and aggression. Chronic elevation of cortisol has been also associated with depression in Cushing's disease (McEwen, Metab. Clin. & Exp. Vol. 54, pages 20-23 (2005)). A number of animal and clinical studies have provided evidence for the correlation between increases in glucocorticoid levels and neuropsychiatric disorders such as major depressive disorder, psychotic depression, anxiety, panic disorder, post traumatic stress disorder, and depression in Cushing's syndrome (Budziszcwska, Polish J. of Pharmacol. Vol. 54 pages 343-349, 2002; Ströhle and Holboer, Pharmacopsychiatry Vol. 36 pages S207-S214, 2003; DeBattista and Belanoff, TRENDS in Endocr. Metab., Vol. 17 pages 117-120, 2006; Norman and Burrows, Expert Rev. Neurotherapeutics Vol. 7, pages 203-213, 2007).

The compounds disclosed in the present application are selective inhibitors of 11β-HSD-1 as described in U.S. patent application publication Nos. 2005/0277747, 2006/0281773, and 2006/0149070, and in U.S. patent application Ser. No. 11/697,044, which are hereby incorporated herein by reference. These compounds are useful in the treatment of non-insulin dependent type 2 diabetes, insulin resistance, obesity, lipid disorders, metabolic syndrome, and other diseases and conditions that are mediated by excessive glucocorticoid action.

The present application describes the utility of these selective inhibitors of 11β-HSD-1 in the treatment of central nervous system disorders, age-related or glucocorticoid-related declines in cognitive function such as those seen in Alzheimer's and associated dementias, major depressive disorder, psychotic depression, anxiety, panic disorder, post traumatic stress disorder, depression in Cushing's syndrome, and treatment resistant depression.

DETAILED DESCRIPTION

Figure 1:
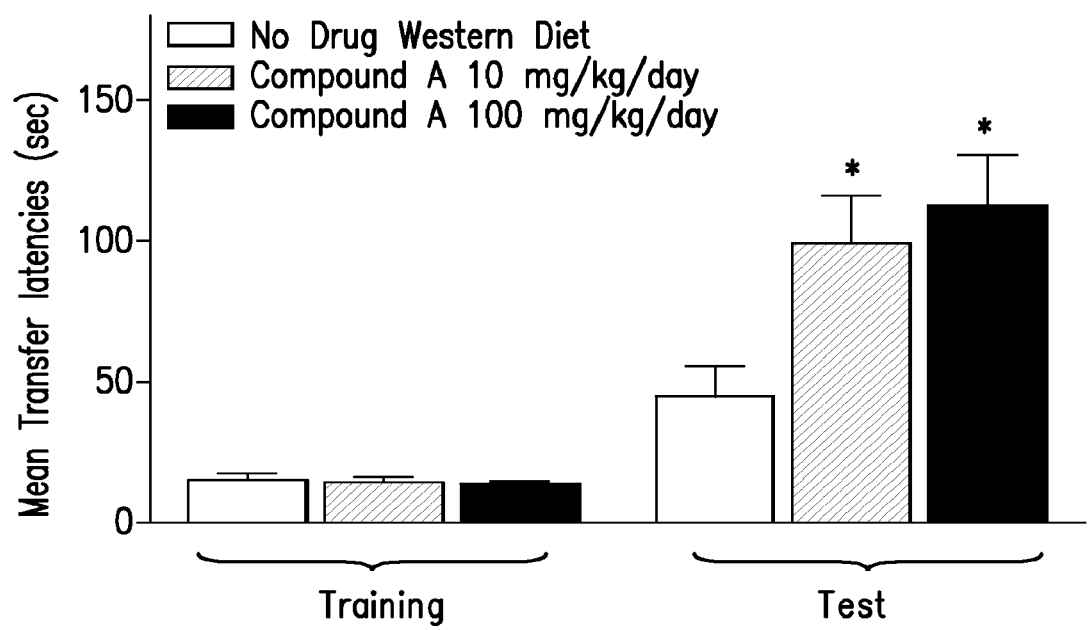
FIG. 1 shows the results of memory consolidation in treated and untreated mice measured as Mean Transfer Latency.

Cognitive symptoms of Alzheimer's are currently treated with acetylcholine esterase inhibitors such as donepezil or NMDA antagonists such as memantine. The efficacy is minimal and short-lived. There is currently no treatment available that will halt or slow the degenerative progression of the disease.

Cognitive deficits associated with schizophrenia are minimally treated with atypical antipsychotics such as olanzapine. There is no adequate treatment for these deficits.

11β-HSD1 ligands regulate central glucocorticoid functioning, which in turn has a significant role in cognitive disorders, stress and mood disorders, schizophrenia and related psychoses, etc. Significant evidence indicates that selective HSD-1 inhibitors will protect against age- or glucocorticoid-related declines in cognitive function such as those seen in Alzheimer's and associated dementias. In addition, evidence implicates excessive glucocorticoids as a risk factor in the development and progression of schizophrenia and indicates that cognitive deficits seen in the disorder are linked to abnormalities in glucocorticoid regulation. Thus, ligands that regulate glucocorticoid levels such as 11β-HSD1 inhibitors can provide useful treatment for these disorders by enhancing cognitive function and delaying disease progression in patients with Alzheimer's, schizophrenia or related disorders. For example, it has been shown that a non-selective 11βHSD1 inhibitors like carbenoxolone improves cognitive function in humans, however the liability of adverse cardiovascular effects liability in particular hypertension, diminishes the value of non-selective 11β-HSD1 inhibitors as useful therapeutic agents. The compounds described in U.S. patent application publication Nos. 2005/0277747, 2006/0281773, and 2006/0149070, and in U.S. patent application Ser. No. 11/697,044, are selective 11β-HSD1 inhibitors. As demonstrated below, these compounds significantly enhance cognitive functioning and induce biochemical events necessary for synaptic plasticity in preclinical species.

Unlike currently available medications for cognitive deficits in Alzheimer's and related dementias, 11β-HSD1 inhibitors such as those in the series described have the potential to be both symptom alleviating and disease modifying. In addition, unlike current treatments such as acetylcholinesterase inhibitors that target neurochemical systems that are deteriorating with the progression of Alzheimer's, a fact that may underlie their short-lived efficacy, 11β-HSD1 inhibitors target a system that is upregulated during aging thereby suggesting they will not lose potency or efficacy over time.

Unlike currently available antipsychotics that have very limited efficacy against the cognitive deficits associated with schizophrenia and related disorders, 11β-HSD1 inhibitors such as those in the series described have the potential to meaningfully alleviate cognitive deficits as well as slow the progressive deterioration in function in schizophrenic patients.

Even if antidepressant drugs remain one of the principal form of treatment for depressive disorders, compounds such as 11β-HSD1 inhibitors represent a potential novel therapeutic strategy to treat all forms of depression, including depression resistant to antidepressant therapies.

Definition of Terms

The term "alkenyl" as used herein, refers to a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl. Alkenyls of the present invention can be unsubstituted or substituted with one substituent selected from the group consisting of carboxy, alkoxycarbonyl and aryloxycarbonyl.

The term "alkoxy" as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy and hexyloxy.

The term "alkoxyalkyl" as used herein, refers to an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl and methoxymethyl.

The term "alkoxycarbonyl" as used herein, refers to an alkoxy group, as defined herein, appended to the parent molecular moiety through a carbonyl group, as defined herein. Representative examples of alkoxycarbonyl include, but are not limited to, methoxycarbonyl, ethoxycarbonyl and tert-butoxycarbonyl.

The term "alkyl" as used herein, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl and n-decyl.

The term "alkylcarbonyl" as used herein, refers to an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl and 1-oxopentyl.

The term "alkylsulfonyl" as used herein, refers to an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkyl-NH" as used herein, refers to an alkyl group, as defined herein, appended to the parent molecular moiety through a nitrogen atom.

The term "alkyl-NH-alkyl" as used herein, refers to an alkyl-NH group, as defined herein, appended to the parent molecular moiety through an alkyl group, as defined herein.

The term "aryl" as used herein, means a phenyl group, or a bicyclic or a tricyclic fused ring system. Bicyclic fused ring systems are exemplified by a phenyl group appended to the parent molecular moiety and fused to a cycloalkyl group, as defined herein, a phenyl group, a heteroaryl group, as defined herein, or a heterocycle, as defined herein. Tricyclic fused ring systems are exemplified by an aryl bicyclic fused ring system, as defined herein and fused to a cycloalkyl group, as defined herein, a phenyl group, a heteroaryl group, as defined herein, or a heterocycle, as defined herein. Representative examples of aryl include, but are not limited to, anthracenyl, azulenyl, fluorenyl, indanyl, indenyl, naphthyl, phenyl and tetrahydronaphthyl.

The aryl groups of this invention may be optionally substituted with 1, 2, 3, 4 or 5 substituents independently selected from alkenyl, alkoxy, alkoxyalkoxy, alkoxyalkyl, alkoxycarbonyl, alkoxycarbonylalkyl, alkyl, alkylcarbonyl, alkylsulfonyl, alkynyl, aryl, arylalkoxy, arylcarbonyl, aryloxy, arylsulfonyl, carboxy, carboxyalkyl, cyano, cyanoalkyl, ethylenedioxy, formyl, haloalkoxy, haloalkyl, halogen, heteroaryl, heteroarylalkyl, heteroarylcarbonyl, heterocycle, heterocyclecarbonyl, heterocycleoxy, heterocyclesulfonyl, hydroxy, hydroxyalkyl, nitro, $R_fR_gN—$, $R_fR_g$Nalkyl, $R_fR_g$Ncarbonyl, $—N(H)C(O)N(H)(alkyl)$, and $R_fR_g$Nsulfonyl, wherein $R_f$ and $R_g$ are independently selected from the group consisting of hydrogen, alkyl, alkoxyalkyl, alkoxycarbonyl, alkylcarbonyl, alkylsulfonyl, cycloalkyl, haloalkyl, haloalkylcarbonyl and cycloalkylalkyl wherein the cycloalkyl, the cycloalkyl of cycloalkylalkyl as represented by $R_f$ and $R_g$ are each independently unsubstituted or substituted with 1, 2 or 3 substituents independently selected from the group consisting of halogen, alkyl and haloalkyl. The substituent aryl, the aryl of arylalkoxy, the awl of arylcarbonyl, the awl of aryloxy, the aryl of arylsulfonyl, the substituent heteroaryl, the heteroaryl of heteroarylalkyl, the heteroaryl of heteroarylcarbonyl, the substituent heterocycle, the heterocycle of heterocyclecarbonyl, the heterocycle of heterocycleoxy, the heterocycle of heterocyclesulfonyl may be optionally substituted with 1, 2 or 3 substituents independently selected from the group consisting of alkoxy, alkoxyalkyl, alkoxycarbonyl, alkyl, alkylcarbonyl, alkynyl, carboxy, carboxyalkyl, cyano, haloalkyl, halogen, hydroxy, hydroxyalkyl, nitro, $R_fR_gN—$, $R_fR_gNalkyl$, $R_fR_gNcarbonyl$ and $R_fR_gNsulfonyl$ wherein $R_f$ and $R_g$ are as described herein.

The term "arylalkenyl" as used herein, refers to an aryl group, as defined herein, appended to the parent molecular moiety through an alkenyl group, as defined herein.

The term "arylalkoxy" as used herein, refers to an aryl group, as defined herein, appended to the parent molecular moiety through an alkoxy group, as defined herein.

The term "arylalkyl" as used herein, refers to an aryl group, as defined herein, appended to the parent molecular moiety through an alkyl group, as defined herein. Representative examples of arylalkyl include, but are not limited to, benzyl, 2-phenylethyl, 3-phenylpropyl and 2-naphth-2-ylethyl.

The term "arylcarbonyl" as used herein, refers to an aryl group, as defined herein, appended to the parent molecular moiety through a carbonyl group, as defined herein. Representative examples of arylcarbonyl include, but are not limited to, benzoyl and naphthoyl.

The term "aryl-heterocycle," as used herein, refers to an aryl group, as defined herein, appended to the parent molecular moiety through a heterocycle group, as defined herein.

The term "aryl-NH—," as used herein, refers to an aryl group, as defined herein, appended to the parent molecular moiety through a nitrogen atom.

The term "aryl-NH-alkyl," as used herein, refers to an aryl-NH— group, as defined herein, appended to the parent molecular moiety through an alkyl group, as defined herein.

The term "aryloxy," as used herein, refers to an aryl group, as defined herein, appended to the parent molecular moiety through an oxy moiety, as defined herein. Representative examples of aryloxy include, but are not limited to, phenoxy, naphthyloxy, 3-bromophenoxy, 4-chlorophenoxy, 4-methylphenoxy, and 3,5-dimethoxyphenoxy.

The term "aryloxyalkyl," as used herein, refers to an aryloxy group, as defined herein, appended to the parent molecular moiety through an alkyl group, as defined herein.

The term "aryloxycarbonyl," as used herein, refers to an aryloxy group, as defined herein, appended to the parent molecular moiety through a carbonyl group, as defined herein.

The term "arylsulfonyl," as used herein, refers to an aryl group, as defined herein, appended to the parent molecular moiety through a sulfonyl group, as defined herein. Representative examples of arylsulfonyl include, but are not limited to, phenylsulfonyl, 4-bromophenylsulfonyl and naphthylsulfonyl.

The term "carbonyl" as used herein refers to a —C(O)— group.

The term "carboxy" as used herein refers to a —C(O)—OH group.

The term "carboxyalkyl" as used herein refers to a carboxy group as defined herein, appended to the parent molecular moiety through an alkyl group as defined herein.

The term "carboxycycloalkyl" as used herein refers to a carboxy group as defined herein, appended to the parent molecular moiety through an cycloalkyl group as defined herein.

The term "cycloalkyl" as used herein, refers to a monocyclic, bicyclic, or tricyclic ring system. Monocyclic ring systems are exemplified by a saturated cyclic hydrocarbon group containing from 3 to 8 carbon atoms. Examples of monocyclic ring systems include cyclopropyl, cyclobutyl, cyclopentyl, cyclohexyl, cycloheptyl and cyclooctyl. Bicyclic fused ring systems are exemplified by a cycloalkyl group appended to the parent molecular moiety and fused to a cycloalkyl group, as defined herein, a phenyl group, a heteroaryl group, as defined herein, or a heterocycle, as defined herein. Tricyclic fused ring systems are exemplified by a cycloalkyl bicyclic fused ring system, as defined herein and fused to a cycloalkyl group, as defined herein, a phenyl group, a heteroaryl group, as defined herein, or a heterocycle, as defined herein. Bicyclic ring systems are also exemplified by a bridged monocyclic ring system in which two non-adjacent carbon atoms of the monocyclic ring are linked by an alkylene bridge of between one and three additional carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane and bicyclo[4.2.1]nonane. Tricyclic ring systems are also exemplified by a bicyclic ring system in which two non-adjacent carbon atoms of the bicyclic ring are linked by a bond or an alkylene bridge of between one and three carbon atoms. Representative examples of tricyclic-ring systems include, but are not limited to, tricyclo[3.3.1.0$^{3,7}$]nonane and tricyclo[3.3.1.1$^{3,7}$]decane (adamantane).

The cycloalkyl groups of this invention may be substituted with 1, 2, 3, 4 or 5 substituents independently selected from alkenyl, alkoxy, alkoxyalkoxy, alkoxyalkyl, alkoxycarbonyl, alkoxycarbonylalkyl, alkyl, alkylcarbonyl, alkynyl, aryl, arylalkyl, arylcarbonyl, aryloxy, arylsulfonyl, carboxy, carboxyalkyl, cyano, cyanoalkyl, cycloalkyl, ethylenedioxy, formyl, haloalkoxy, haloalkyl, halogen, heteroaryl, heteroarylalkyl, heteroarylcarbonyl, heterocycle, heterocyclealkyl, heterocyclecarbonyl, heterocycleoxy, hydroxy, hydroxyalkyl, nitro, $R_fR_gN—$, $R_fR_gNalkyl$, $R_fR_gNcarbonyl$ and $R_fR_gNsulfonyl$, wherein $R_f$ and $R_g$ are independently selected from the group consisting of hydrogen, alkyl, alkoxyalkyl, alkoxycarbonyl, alkylcarbonyl, alkylsulfonyl, cycloalkyl, haloalkyl, haloalkylcarbonyl and cycloalkylalkyl wherein the cycloalkyl, the cycloalkyl of cycloalkylalkyl as represented by $R_f$ and $R_g$ are each independently unsubstituted or substituted with 1, 2 or 3 substituents independently selected from the group consisting of halogen, alkyl and haloalkyl. The substituent aryl, the aryl of arylalkyl, the aryl of arylcarbonyl, the aryl of aryloxy, the aryl of arylsulfonyl, the substituent heteroaryl, the heteroaryl of heteroarylalkyl, the heteroaryl of heteroarylcarbonyl, the substituent heterocycle, the heterocycle of heterocyclealkyl, the heterocycle of heterocyclecarbonyl, the heterocycle of heterocycleoxy, the heterocycle of heterocyclesulfonyl may be optionally substituted with 0, 1, 2 or 3 substituents independently selected from the group consisting of alkoxy, alkoxyalkyl, alkoxycarbonyl, alkyl, alkylcarbonyl, alkynyl, carboxy, carboxyalkyl, cyano, haloalkyl, halogen, hydroxy, hydroxyalkyl, nitro, $R_fR_gN$—, $R_fR_g$Nalkyl, $R_fR_g$Ncarbonyl and $R_fR_g$Nsulfonyl wherein $R_f$ and $R_g$ are as described herein.

The term "cycloalkylalkyl" as used herein, refers to a cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl and 4-cycloheptylbutyl.

The term "cycloalkylcarbonyl" as used herein, refers to cycloalkyl group, as defined herein, appended to the parent molecular moiety through a carbonyl group, as defined herein. Representative examples of cycloalkylcarbonyl include, but are not limited to, cyclopropylcarbonyl, 2-cyclobutylcarbonyl and cyclohexylcarbonyl.

The term "cycloalkyloxy" as used herein, refers to cycloalkyl group, as defined herein, appended to the parent molecular moiety through an oxy group, as defined herein.

The term "cycloalkylsulfonyl" as used herein, refers to cycloalkyl group, as defined herein, appended to the parent molecular moiety through a sulfonyl group, as defined herein. Representative examples of cycloalkylsulfonyl include, but are not limited to, cyclohexylsulfonyl and cyclobutylsulfonyl.

The term "halo" or "halogen" as used herein, refers to —Cl, —Br, —I or —F.

The term "haloalkyl" as used herein, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl and 2-chloro-3-fluoropentyl.

The term "haloalkylcarbonyl" as used herein, refers to a haloalkyl group, as defined herein, appended to the parent molecular moiety through a carbonyl group, as defined herein.

The term "heteroaryl" as used herein, refers to an aromatic monocyclic ring or an aromatic bicyclic ring system. The aromatic monocyclic rings are five or six membered rings containing at least one heteroatom independently selected from the group consisting of N, O and S. The five membered aromatic monocyclic rings have two double bonds and the six membered aromatic monocyclic rings have three double bonds. The bicyclic heteroaryl groups are exemplified by a monocyclic heteroaryl ring appended to the parent molecular moiety and fused to a monocyclic cycloalkyl group, as defined herein, a monocyclic aryl group, as defined herein, a monocyclic heteroaryl group, as defined herein, or a monocyclic heterocycle, as defined herein. Representative examples of heteroaryl include, but are not limited to, benzimidazolyl, benzofuranyl, benzothiazolyl, benzothienyl, benzoxazolyl, furyl, imidazolyl, indazolyl, indolyl, indolizinyl, isobenzofuranyl, isoindolyl, isoxazolyl, isoquinolinyl, isothiazolyl, naphthyridinyl, oxadiazolyl, oxazolyl, phthalazinyl, pyridinyl, pyridazinyl, pyrimidinyl, pyrazinyl, pyrazolyl, pyrrolyl, quinolinyl, quinolizinyl, quinoxalinyl, quinazolinyl, tetrazolyl, thiadiazolyl, thiazolyl, thienyl, triazolyl and triazinyl.

The term "heteroarylalkyl" as used herein, refers to a heteroaryl, as defined herein, appended to the parent molecular moiety through an alkyl group, as defined herein.

The heteroaryls of this invention may be optionally substituted with 1, 2 or 3 substituents independently selected from alkenyl, alkoxy, alkoxyalkoxy, alkoxyalkyl, alkoxycarbonyl, alkoxycarbonylalkyl, alkyl, alkylcarbonyl, alkynyl, aryl, arylalkyl, arylcarbonyl, aryloxy, arylsulfonyl, carboxy, carboxyalkyl, cyano, cyanoalkyl, cycloalkyl, ethylenedioxy, formyl, haloalkoxy, haloalkyl, halogen, heteroaryl, heteroarylalkyl, heterocycle, heterocyclealkyl, heterocyclecarbonyl, heterocycleoxy, hydroxy, hydroxyalkyl, nitro, $R_fR_gN$—, $R_fR_g$Nalkyl, $R_fR_g$Ncarbonyl and $R_fR_g$Nsulfonyl, wherein $R_f$ and $R_g$ are independently selected from the group consisting of hydrogen, alkyl, alkoxyalkyl, alkoxycarbonyl, alkylcarbonyl, alkylsulfonyl, cycloalkyl, haloalkyl, haloalkylcarbonyl and cycloalkylalkyl wherein the cycloalkyl, the cycloalkyl of cycloalkylalkyl as represented by $R_f$ and $R_g$ are each independently unsubstituted or substituted with 1, 2 or 3 substituents independently selected from the group consisting of halogen, alkyl and haloalkyl. The substituent aryl, the aryl of arylalkyl, the aryl of arylcarbonyl, the aryl of aryloxy, the aryl of arylsulfonyl, the substituent heteroaryl, the heteroaryl of heteroarylalkyl, the substituent heterocycle, the heterocycle of heterocyclealkyl, the heterocycle of heterocyclecarbonyl, the heterocycle of heterocycleoxy may be optionally substituted with 1, 2 or 3 substituents independently selected from the group consisting of alkoxy, alkoxyalkyl, alkoxycarbonyl, alkyl, alkylcarbonyl, alkynyl, carboxy, carboxyalkyl, cyano, haloalkyl, halogen, hydroxy, hydroxyalkyl, nitro, $R_fR_gN$—, $R_fR_g$Nalkyl, $R_fR_g$Ncarbonyl and $R_fR_g$Nsulfonyl wherein $R_f$ and $R_g$ are as described above.

The term "heterocycle" as used herein, refers to a non-aromatic monocyclic ring or a non-aromatic bicyclic ring. The non-aromatic monocyclic ring is a three, four, five, six, seven, or eight membered ring containing at least one heteroatom, independently selected from the group consisting of N, O and S. Representative examples of monocyclic ring systems include, but are not limited to, azetidinyl, aziridinyl, diazepinyl, dithianyl, imidazolinyl, imidazolidinyl, isothiazolinyl, isoxazolinyl, isoxazolidinyl, morpholinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydro-2H-pyranyl, tetrahydro-2H-pyran-2-yl, tetrahydro-2H-pyran-4-yl, tetrahydrothienyl, thiazolinyl, thiazolidinyl, thiomorpholinyl, 1,1-dioxidothiomorpholinyl (thiomorpholine sulfone) and thiopyranyl. The bicyclic heterocycles are exemplified by a monocyclic heterocycle appended to the parent molecular moiety and fused to a monocyclic cycloalkyl group, as defined herein, a monocyclic awl group, a monocyclic heteroaryl group, as defined herein, or a monocyclic heterocycle, as defined herein. Bicyclic ring systems are also exemplified by a bridged monocyclic ring system in which two non-adjacent atoms of the monocyclic ring are linked by a bridge of between one and three additional atoms selected from the group consisting of carbon, nitrogen and oxygen. Bicyclic ring systems are exemplified by any of the above monocyclic ring systems fused to a phenyl group, a monocyclic cycloalkenyl group, as defined herein, a monocyclic cycloalkyl group, as defined herein, or an additional monocyclic heterocycle group, as defined herein. Representative examples of bicyclic ring systems include, but are not limited to, benzodioxinyl, benzodioxolyl, benzopyranyl, benzothiopyranyl, 2,3-dihydroindol-3-yl, 2,3-dihydrobenzofuran-3-yl, 2,3-dihydrobenzothien-3-yl, 2,3-dihydroisoindol-3-yl, 1,3-dihydro-isobenzofuran-3-yl, 1,3-dihydrobenzo[c]thien-3-yl, tetrahydroisoquinolinyl, tetrahydroquinolinyl, 3-azabicyclo[3.2.0]heptyl, 3,6-diazabicyclo[3.2.0]heptyl, octahydrocyclopenta[c]pyrrolyl, hexahydro-1H-furo[3,4-c]pyrrolyl, cinnolinyl, 1,5-diazocanyl, 3,9-diaza-bicyclo[4.2.1]non-9-yl, 3,7-diazabicyclo[3.3.1]nonane, octahydro-pyrrrolo[3,4-c]pyrrole, indolinyl, isoindolinyl, 2,3,4,5-tetrahydro-1H-benzo[c]azepine, 2,3,4,5-tetrahydro-1H-benzo[b]azepine, 2,3,4,5-tetrahydro-1H- benzo[d]azepine, tetrahydroisoquinolinyl, tetrahydroquinolinyl and octahydropyrrolo[3,4-c]pyrrolyl. The monocyclic or bicyclic ring systems as defined herein can have two of the non-adjacent carbon atoms connected by a heteroatom selected from nitrogen, oxygen, or sulfur, or an alkylene bridge of between one and three additional carbon atoms. Representative examples of monocyclic or bicyclic ring systems that contain such connection between two non-adjacent carbon atoms include, but are not limited to, 2-azabicyclo[2.2.2]octyl, 2-oxa-5-azabicyclo[2.2.2]octyl, 2,5-diazabicyclo[2.2.2]octyl, 2-azabicyclo[2.2.1]heptyl, 2-oxa-5-azabicyclo[2.2.1]heptyl, 2,5-diazabicyclo[2.2.1]heptyl, 2-azabicyclo[2.1.1]hexyl, 5-azabicyclo[2.1.1]hexyl, 3-azabicyclo[3.1.1]heptyl, 6-oxa-3-azabicyclo[3.1.]heptyl, 8-azabicyclo[3.2.1]octyl, 8-azabicyclo[3.2.1]oct-8-yl, 3-oxa-8-azabicyclo[3.2.1]octyl, 1,4-diazabicyclo[3.2.2]nonyl, 1,4-diazatricyclo[4.3.1.1$^{3,8}$]undecyl, 3,10-diazabicyclo[4.3.1]decyl, 8-oxa-3-azabicyclo[3.2.1]octyl, octahydro-1H-4,7-methanoisoindolyl, and octahydro-1H-4,7-epoxyisoindolyl. The heterocycle groups of the invention are substituted or unsubstituted, and are connected to the parent molecular moiety through any substitutable carbon or nitrogen atom in the groups. The nitrogen heteroatom can or cannot be quaternized, and the nitrogen or sulfur heteroatom can or cannot be oxidized. In addition, the nitrogen including heterocyclic rings can or cannot be N-protected.

The heterocycles of this invention may be optionally substituted with 1, 2 or 3 substituents independently selected from alkenyl, alkoxy, alkoxyalkoxy, alkoxyalkyl, alkoxycarbonyl, alkoxycarbonylalkyl, alkyl, alkylcarbonyl, alkynyl, aryl, arylalkyl, arylcarbonyl, aryloxy, arylsulfonyl, carboxy, carboxyalkyl, cyano, cyano alkyl, ethylenedioxy, formyl, haloalkoxy, haloalkyl, halogen, heteroaryl, heteroarylalkyl, heterocycle, heterocyclealkyl, heterocyclecarbonyl, heterocycleoxy, hydroxy, hydroxyalkyl, nitro, $R_fR_gN-$, $R_fR_g$Nalkyl, $R_fR_g$Ncarbonyl and $R_fR_g$Nsulfonyl, wherein $R_f$ and $R_g$ are independently selected from the group consisting of hydrogen, alkyl, alkoxyalkyl, alkoxycarbonyl, alkylcarbonyl, alkylsulfonyl, cycloalkyl, haloalkyl, haloalkylcarbonyl and cycloalkylalkyl wherein the cycloalkyl, the cycloalkyl of cycloalkylalkyl as represented by $R_f$ and $R_g$ are each independently unsubstituted or substituted with 1, 2 or 3 substituents independently selected from the group consisting of halogen, alkyl and haloalkyl. The substituent aryl, the aryl of arylalkyl, the aryl of arylcarbonyl, the aryl of aryloxy, the aryl of arylsulfonyl, the heteroaryl, the heteroaryl of heteroarylalkyl, the substituent heterocycle, the heterocycle of heterocyclealkyl, the heterocycle of heterocyclecarbonyl, the heterocycle of heterocycleoxy, may be optionally substituted with 1, 2 or 3 substituents independently selected from the group consisting of alkoxy, alkoxyalkyl, alkoxycarbonyl, alkyl, alkylcarbonyl, alkynyl, carboxy, carboxyalkyl, cyano, haloalkyl, halogen, hydroxy, hydroxyalkyl, nitro, $R_fR_gN-$, $R_fR_g$Nalkyl, $R_fR_g$Ncarbonyl and $R_fR_g$Nsulfonyl wherein $R_f$ and $R_g$ are as described herein.

The term "heterocyclealkyl" as used herein, refers to a heterocycle, as defined herein, appended to the parent molecular moiety through an alkyl group, as defined herein. Representative examples of heterocyclealkyl include, but are not limited to, pyridin-3-ylmethyl and 2-pyrimidin-2-ylpropyl.

The term "heterocyclealkoxy" as used herein, refers to a heterocycle, as defined herein, appended to the parent molecular moiety through an alkoxy group, as defined herein.

The term "heterocycleoxy" as used herein, refers to a heterocycle, as defined herein, appended to the parent molecular moiety through an oxy group, as defined herein.

The term "heterocycleoxyalkyl" as used herein, refers to a hetcrocycleoxy, as defined herein, appended to the parent molecular moiety through an alkyl group, as defined herein.

The term "heterocycle-NH—" as used herein, refers to a heterocycle, as defined herein, appended to the parent molecular moiety through a nitrogen atom.

The term "heterocycle-NH-alkyl" as used herein, refers to a heterocycle-NH—, as defined herein, appended to the parent molecular moiety through an alkyl group, as defined herein.

The term "heterocyclecarbonyl" as used herein, refers to a heterocycle, as defined herein, appended to the parent molecular moiety through a carbonyl group, as defined herein. Representative examples of heterocyclecarbonyl include, but are not limited to, 1-piperidinylcarbonyl, 4-morpholinylcarbonyl, pyridin-3-ylcarbonyl and quinolin-3-ylcarbonyl.

The term "heterocyclesulfonyl" as used herein, refers to a heterocycle, as defined herein, appended to the parent molecular moiety through a sulfonyl group, as defined herein. Representative examples of heterocyclesulfonyl include, but are not limited to, 1-piperidinylsulfonyl, 4-morpholinylsulfonyl, pyridin-3-ylsulfonyl and quinolin-3-ylsulfonyl.

The term "hydroxy" as used herein, refers to an —OH group.

The term "hydroxyalkyl" as used herein, refers to a hydroxy group, as defined herein, appended to the parent molecular moiety through an alkyl group, as defined herein. Representative examples of hydroxyalkyl include, but are not limited to, hydroxymethyl, 2-hydroxyethyl, 3-hydroxypropyl and 2-ethyl-4-hydroxyheptyl.

The term "oxo" as used herein, refers to a =O group.

The term "oxy" as used herein, refers to a —O— group.

The compounds of the present invention can exist as therapeutically acceptable salts. The term "therapeutically acceptable salt," refers to salts or zwitterions of the compounds that are water or oil-soluble or dispersible, suitable for treatment of disorders without undue toxicity, irritation and allergic response, commensurate with a reasonable benefit/risk ratio and effective for their intended use. The salts can be prepared during the final isolation and purification of the compounds or separately by reacting an amino group of the compounds with a suitable acid. For example, a compound can be dissolved in a suitable solvent, such as, but not limited to, methanol and water, and treated with at least one equivalent of an acid such as hydrochloric acid. The resulting salt can precipitate out and be isolated by filtration and dried under reduced pressure. Alternatively, the solvent and excess acid can be removed under reduced pressure to provide the salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, pierate, oxalate, maleate, pivalate, propionate, succinate, tartrate, trichloroacetate, trifluoroacetate, glutamate, para-toluenesulfonate, undecanoate, hydrochloric, hydrobromic, sulfuric, phosphoric, and the like. The amino groups of the compounds can also be quaternized with alkyl chlorides, bromides, and iodides such as methyl, ethyl, propyl, isopropyl, butyl, lauryl, myristyl, stearyl, and the like.

Basic addition salts can be prepared during the final isolation and purification of the present compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine Quaternary amine salts derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine and the like, are contemplated as being within the scope of the present invention.

The term "pharmaceutically acceptable prodrug," refers to those prodrugs or zwitterions, which are suitable for use in contact with the tissues of patients without undue toxicity, irritation, and allergic response, are commensurate with a reasonable benefit/risk ratio, and are effective for their intended use. The term "prodrug," refers to compounds that are rapidly transformed in vivo to the parent compounds of formula (I), for example, by hydrolysis in blood. The term "prodrug," refers to compounds that contain, but are not limited to, substituents known as "therapeutically acceptable esters." The term "therapeutically acceptable ester" refers to alkoxycarbonyl groups appended to the parent molecule on an available carbon atom. More specifically, a "therapeutically acceptable ester" refers to alkoxycarbonyl groups appended to the parent molecule on one or more available aryl, cycloalkyl, and/or heterocycle groups as defined herein. Examples of prodrug ester groups include pivaloyloxymethyl, acetoxymethyl, phthalidyl, indanyl and methoxymethyl, as well as other such groups known in the art. Other examples of prodrug ester groups are found in T. Higuchi and V. Stella, Pro-drugs as Novel Delivery Systems, Vol. 14 of the A.C.S. Symposium Series and in Edward B. Roche, ed., *Bioreversible Carriers in Drug Design*, American Pharmaceutical Association and Pergamon Press, 1987, both of which are incorporated herein by reference in their entirety.

The term "therapeutically effective amount" refers to a sufficient amount of a compound of formula (I) to effectively ameliorate disorders by inhibiting 11-beta-hydroxysteroid dehydrogenase Type 1 enzyme at a reasonable benefit/risk ratio applicable to any medical treatment. The specific therapeutically effective dose level for any particular patient can depend upon a variety of factors including the disorder being treated and the severity of the disorder; the activity of the compound employed; the specific composition employed; the age, body weight, general health, sex, and diet of the patient; the time of administration, route of administration, rate of excretion; the duration of the treatment; and drugs used in combination or coincidental therapy.

Methods of the Invention

Compounds and compositions of the invention are useful for treating central nervous system disorders, cognitive deficits and dementias associated with a diversity of conditions, including age-related or glucocorticoid-related declines in cognitive function such as those seen in Alzheimer's and associated dementias, major depressive disorder, psychotic depression, anxiety, panic disorder, post traumatic stress disorder, depression in Cushing's syndrome, and treatment resistant depression.

The compounds of the invention, including but not limited to those specified in the examples, are selective inhibitors of 11β-HSD-1. 11β-HSD-1 is expressed in mammalian brain, and published data indicates that elevated levels of glucocorticoids may cause neuronal degeneration and dysfunction, particularly in the aged (de Quervain et al.; *Hum Mol Genet*. Vol. 13 pages 47-52, 2004; Belanoff et al. *J. Psychiatr Res*. Vol. 35, pages 127-35, 2001). In addition, chronic excessive cortisol levels in the brain may result in neuronal loss and neuronal dysfunction. (See, D. S. Kerr et al., *Psychobiology*, Vol. 22 pages 123-133, 1994, C. Woolley, *Brain Res*. Vol. 531 pages 225-231, 1990, P. W. Landfield, *Science*, Vol. 272 pages 1249-1251, 1996). As such, the 11β-HSD-1 inhibitors disclosed herein, are suitable for the treatment of cognitive disorders including, for example, Alzheimer's and associated dementias.

It has been recently shown that 11β-HSD-1 mRNA is expressed in human hippocampus, frontal cortex and cerebellum, and that treatment of elderly diabetic individuals with the non-selective 11β-HSD-1 and 11β-HSD-2 inhibitor carbenoxolone improved verbal fluency and memory (Thekkapat et al., *Proc Natl Acad Sci USA*. Vol. 101, pages 6743-6749, 2004). Therefore, the 11β-HSD-1 inhibitors disclosed herein can counter the memory and expression deficits of Alzheimer's and other neurodegenerative diseases.

Excessive glucocorticoid levels also affects psychopathology, as shown in animal models, it leads to increased anxiety and aggression. Chronic elevation of cortisol has been also associated with depression in Cushing's disease (McEwen, *Metab. Clin. & Exp*. Vol. 54, pages 20-23 (2005)). A number of animal and clinical studies have provided evidence for the correlation between increases in glucocorticoid levels and neuropsychiatric disorders such as major depressive disorder, psychotic depression, anxiety, panic disorder, post traumatic stress disorder, and depression in Cushing's syndrome (Budziszewska, *Polish J. of Pharmacol*. Vol. 54 pages 343-349, 2002; Ströhle and Holboer, *Pharmacopsychiatry* Vol. 36 pages S207-S214, 2003; DeBattista and Belanoff, *TRENDS in Endocr. Metab.*, Vol. 17 pages 117-120, 2006; Norman and Burrows, *Expert Rev. Neurotherapeutics* Vol. 7, pages 203-213, 2007). As such, the 11β-HSD-1 inhibitors disclosed herein are suitable for the treatment of major depressive disorder, psychotic depression, anxiety, panic disorder, post-traumatic stress disorder, depression in Cushing's syndrome, and treatment resistant depression.

Compounds of the Invention

The selective 11β-HSD1 inhibitors discussed in the present application can be selected from a group of compounds having formula (I),

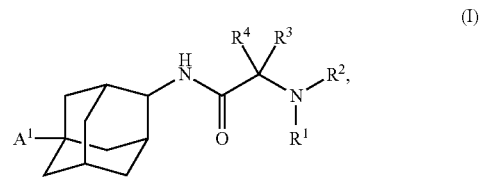

wherein $A^1$ is selected from the group consisting of alkyl, alkyl-NH-alkyl, alkylcarbonyl, alkylsulfonyl, cycloalkyl, cycloalkylcarbonyl, cycloalkylsulfonyl, arylcarbonyl, arylsulfonyl, heterocyclecarbonyl, heterocyclesulfonyl, aryl, arylalkyl, aryloxyalkyl, carboxyalkyl, carboxycycloalkyl, halogen, haloalkyl, heterocycle, heterocyclealkyl, heterocycleoxyalkyl, —NR$^7$—[C(R$^8$R$^9$)]$_n$—C(O)—R$^{10}$, —O—[C(R$^{11}$R$^{12}$)]$_p$—C(O)—R$^{13}$, —OR$^{14}$, —N(R$^{15}$R$^{16}$), —CO$_2$R$^{17}$, —C(O)—N(R$^{18}$R$^{19}$), —C(R$^{20}$R$^{21}$)—OR$^{22}$, and —C(R$^{23}$R$^{24}$)—N(R$^{25}$R$^{26}$);

R$^1$ and R$^2$ are each independently selected from the group consisting of hydrogen, alkyl, alkoxyalkyl, alkyl-NH-alkyl, aryloxyalkyl, aryl-NH-alkyl, carboxyalkyl, carboxycycloalkyl, heterocycleoxyalkyl, heterocycle-NH-alkyl, cycloalkyl, aryl, arylalkyl, haloalkyl, heterocycle, heterocyclealkyl, heterocycle-heterocycle, and aryl-heterocycle, or R$^1$ and R$^2$ together with the atom to which they are attached form a heterocycle;

R$^3$ and R$^4$ are each independently selected from the group consisting of hydrogen, alkyl, cycloalkyl, or R$^3$ and R$^4$ together with the atom to which they are attached form a ring selected from the group consisting of cycloalkyl;

or R$^2$ and R$^3$ together with the atoms to which they are attached form a non-aromatic heterocycle;

R$^7$ is selected from the group consisting of hydrogen, alkyl, carboxyalkyl, cycloalkyl, carboxycycloalkyl, aryl, arylalkyl, aryloxyalkyl, aryloxy, hydroxy, alkoxy, cycloalkyloxy, heterocycleoxy, heterocycle, heterocyclealkyl, and heterocycleoxyalkyl;

R$^8$ and R$^9$ are each independently selected from the group consisting of hydrogen, alkyl, carboxy, carboxyalkyl, cycloalkyl, carboxycycloalkyl, aryl, arylalkyl, aryloxyalkyl, heterocycle, heterocyclealkyl, and heterocycleoxyalkyl, or R$^8$ and R$^9$ together with the atom to which they are attached form a ring selected from the group consisting of cycloalkyl and non-aromatic heterocycle;

R$^{10}$ is selected from the group consisting of hydrogen, alkyl, carboxy, carboxyalkyl, cycloalkyl, carboxycycloalkyl, aryl, aryloxy, arylalkyl, aryloxyalkyl, hydroxy, alkoxy, cycloalkyloxy, heterocycleoxy, heterocycle, heterocyclealkyl, heterocycleoxyalkyl, and —N(R$^{27}$R$^{28}$);

R$^{11}$ and R$^{12}$ are each independently selected from the group consisting of hydrogen, alkyl, carboxy, carboxyalkyl, cycloalkyl, carboxycycloalkyl, aryl, arylalkyl, aryloxyalkyl, heterocycle, heterocyclealkyl, and heterocycleoxyalkyl, or R$^{11}$ and R$^{12}$ together with the atom to which they are attached form a ring selected from the group consisting of cycloalkyl and non-aromatic heterocycle;

R$^{13}$ is selected from the group consisting of hydrogen, alkyl, carboxy, carboxyalkyl, cycloalkyl, carboxycycloalkyl, aryl, arylalkyl, aryloxy, aryloxyalkyl, hydroxy, alkoxy, cycloalkyloxy, heterocycleoxy, heterocycle, heterocyclealkyl, heterocycleoxyalkyl, and —N(R$^{29}$R$^{30}$);

R$^{14}$ is selected from the group consisting of hydrogen, alkyl, carboxyalkyl, cycloalkyl, carboxycycloalkyl, aryl, arylalkyl, aryloxyalkyl, haloalkyl, heterocycle, heterocyclealkyl, and heterocycleoxyalkyl;

R$^{15}$ and R$^{16}$ are each independently selected from the group consisting of hydrogen, alkyl, carboxyalkyl, cycloalkyl, carboxycycloalkyl, aryl, arylalkyl, aryloxyalkyl, heterocycle, heterocyclealkyl, heterocycleoxyalkyl, alkylsufonyl, cycloalkylsulfonyl, arylsulfonyl, and heterocyclesulfonyl, or R$^{15}$ and R$^{16}$ together with the atom to which they are attached form a heterocycle;

R$^{17}$ is selected from the group consisting of hydrogen, alkyl, carboxyalkyl, cycloalkyl, carboxycycloalkyl, aryl, arylalkyl, aryloxyalkyl, heterocycle, heterocyclealkyl, and heterocycleoxyalkyl;

R$^{18}$ and R$^{19}$ are each independently selected from the group consisting of hydrogen, alkyl, carboxy, carboxyalkyl, cycloalkyl, cycloalkyloxy, carboxycycloalkyl, aryl, arylalkyl, aryloxy, aryloxyalkyl, heterocycle, heterocyclealkyl, heterocycleoxyalkyl, heterocycleoxy, hydroxy, alkoxy, alkylsufonyl, cycloalkylsulfonyl, arylsulfonyl, and heterocyclesulfonyl, or R$^{18}$ and R$^{19}$ together with the atom to which they are attached form a non-aromatic heterocycle;

R$^{20}$, R$^{21}$ and R$^{22}$ are each independently selected from the group consisting of hydrogen, alkyl, carboxyalkyl, carboxycycloalkyl, cycloalkyl, haloalkyl, aryl, and heterocycle;

R$^{23}$ and R$^{24}$ are each independently selected from the group consisting of hydrogen, alkyl, alkylcarbonyl, alkylsulfonyl, carboxyalkyl, carboxycycloalkyl, cycloalkylcarbonyl, cycloalkylsulfonyl, arylcarbonyl, arylsulfonyl, heterocyclecarbonyl, heterocyclesulfonyl, cycloalkyl, aryl, and heterocycle;

R$^{25}$ and R$^{26}$ are each independently selected from the group consisting of hydrogen, alkyl, alkylcarbonyl, alkylsulfonyl, carboxyalkyl, carboxycycloalkyl, cycloalkylcarbonyl, cycloalkylsulfonyl, arylcarbonyl, arylsulfonyl, heterocyclecarbonyl, heterocyclesulfonyl, hydroxy, alkoxy, cycloalkyloxy, aryloxy, heterocycleoxy, cycloalkyl, aryl, and heterocycle, or R$^{25}$ and R$^{26}$ together with the atom to which they are attached form a heterocycle;

R$^{27}$ and R$^{28}$ are each independently selected from the group consisting of hydrogen, alkyl, carboxy, carboxyalkyl, cycloalkyl, cycloalkyloxy, carboxycycloalkyl, aryl, arylalkyl, aryloxy, aryloxyalkyl, heterocycle, heterocyclealkyl, heterocycleoxyalkyl, heterocycleoxy, hydroxy, alkoxy, alkylsufonyl, cycloalkylsulfonyl, arylsulfonyl, and heterocyclesulfonyl, or R$^{27}$ and R$^{28}$ together with the atom to which they are attached form a non-aromatic heterocycle; and R$^{29}$ and R$^{30}$ are each independently selected from the group consisting of hydrogen, alkyl, carboxy, carboxyalkyl, cycloalkyl, cycloalkyloxy, carboxycycloalkyl, aryl, arylalkyl, aryloxy, aryloxyalkyl, heterocycle, heterocyclealkyl, heterocycleoxyalkyl, heterocycleoxy, hydroxy, alkoxy, alkylsufonyl, cycloalkylsulfonyl, arylsulfonyl, and heterocyclesulfonyl, or R$^{29}$ and R$^{30}$ together with the atom to which they are attached form a non-aromatic heterocycle;

or a pharmaceutically acceptable metabolite, salt, prodrug, salt of a prodrug, or a combination thereof.

Examples of compounds of formula (I) are

N—[(Z)-5-hydroxy-2-adamantyl]-2-{4-[5-(trifluoromethyl)pyridin-2-yl]piperazin-1-yl}acetamide;

N-[(E)-5-hydroxy-2-adamantyl]-2-{4-[5-(trifluoromethyl)pyridin-2-yl]piperazin-1-yl}acetamide;

N-[(E)-5-hydroxy-2-adamantyl]-2-{4-[5-(trifluoromethyl)pyridin-2-yl]piperazin-1-yl}propanamide;

2-[(cis)-2,6-dimethylmorpholin-4-yl]-N-[(E)-5-hydroxy-2-adamantyl]propanamide;

N—[(Z)-5-hydroxy-2-adamantyl]-2-(4-hydroxypiperidin-1-yl)propanamide;

N-[(E)-5-hydroxy-2-adamantyl]-2-(4-hydroxypiperidin-1-yl)propanamide;

2-azepan-1-yl-N-[(E)-5-hydroxy-2-adamantyl]propanamide;

(E)-4-[({4-[5-(trifluoromethyl)pyridin-2-yl]piperazin-1-yl}acetyl)amino]-1-adamantyl carbamate;

(E)-4-[(2-{4-[5-(trifluoromethyl)pyridin-2-yl]piperazin-1-yl}acetyl)amino]-1-adamantyl acetate;

N-[(E)-5-(acetylamino)-2-adamantyl]-2-{4-[5-(trifluoromethyl)pyridin-2-yl]piperazin-1-yl}acetamide;

N-[(E)-5-fluoro-2-adamantyl]-2-{4-[5-(trifluoromethyl)pyridin-2-yl]piperazin-1-yl}acetamide;

N-[(Z)-5-fluoro-2-adamantyl]-2-{4-[5-(trifluoromethyl)pyridin-2-yl]piperazin-1-yl}acetamide;

N-[(E)-5-hydroxy-2-adamantyl]-2-[4-(5-methylpyridin-2-yl)piperazin-1-yl]propanamide;

N-[(E)-5-hydroxy-2-adamantyl]-2-methyl-2-{4-[5-(trifluoromethyl)pyridin-2-yl]piperazin-1-yl}propanamide;
(E)-4-{2-methyl-2-[4-(5-trifluoromethyl-pyridin-2-yl)-piperazin-1-yl]-propionylamino}-adamantane-1-carboxylic acid;
(E)-4-({1-[4-(5-trifluoromethyl-pyridin-2-yl)-piperazin-1-yl]-cyclopropanecarbonyl}-amino)-adamantane-1-carboxylic acid;
(E)-4-({1-[4-(5-trifluoromethyl-pyridin-2-yl)-piperazin-1-yl]-cyclopropanecarbonyl}-amino)-adamantane-1-carboxyamide;
(E)-4-{2-[4-(5-trifluoromethyl-pyridin-2-yl)-piperazin-1-yl]-butyrylamino}-adamantane-1-carboxyamide;
(E)-4-{2-cyclopropyl-2-[4-(5-trifluoromethyl-pyridin-2-yl)-piperazin-1-yl]-acetylamino}-adamantane-1-carboxyamide;
(E)-4-({1-[4-(5-trifluoromethyl-pyridin-2-yl)-piperazin-1-yl]-cyclobutanecarbonyl}-amino)-adamantane-1-carboxyamide;
(E)-N-(5-hydroxymethyl-adamantan-2-yl)-2-[4-(5-trifluoromethyl-pyridin-2-yl)-piperazin-1-yl]-isobutyramide;
(E)-N-(5-formyl-adamantan-2-yl)-2-[4-(5-trifluoromethyl-pyridin-2-yl)-piperazin-1-yl]-isobutyramide;
(E)-4-{2-methyl-2-[4-(5-trifluoromethyl-pyridin-2-yl)-piperazin-1-yl]-propionylamino}-adamantane-1-carboxyamide;
(E)-4-{2-methyl-2-[4-(5-trifluoromethyl-pyridin-2-yl)-piperazin-1-yl]-propionylamino}-adamantane-1-carboxylic acid hydroxyamide;
(E)-4-{2-[4-(5-trifluormethyl-pyridin-2-yl)-piperazin-1-yl]-acetylamino}-adamantane-1-carboxylic acid;
(E)-4-[2-(3,3-difluoro-piperidin-1-yl)-acetylamino]-adamantane-1-carboxylic acid;
(E)-4-[2-(2-trifluoromethyl-pyrrolidin-1-yl)-acetylamino]-adamantane-1-carboxylic acid;
(E)-4-{2-[4-(5-trifluoromethyl-pyridin-2-yl)-piperazin-1-yl]-acetylamino}-adamantane-1-carboxyamide;
(E)-4-[2-(2-trifluoromethyl-pyrrolidin-1-yl)-acetylamino]-adamantane-1-carboxyamide;
(E)-4-[2-(3,3-difluoro-piperidin-1-yl)-acetylamino]-adamantane-1-carboxyamide;
(E)-4-[2-(3-fluoropyrrolidin-1-yl)-propionylamino]-adamantane-1-carboxyamide;
(E)-4-[2-(3,3-difluoropiperidine-1-yl)-propionylamino]-adamantane-1-carboxyamide;
(E)-4-[2-(2-trifluoromethylpyrrolidin-1-yl)-propionylamino]-adamantane-1-carboxyamide;
(E)-4-{2-[4-(5-chloro-pyridin-2-yl)-piperazin-1-yl]-2-methyl-propionylamino}-adamantane-1-carboxylic acid;
(E)-4-[2-methyl-2-(1,2,4,5-tetrahydro-benzo[d]azepin-3-yl)-propionylamino]-adamantane-1-carboxylic acid;
(E)-4-[2-methyl-2-(4-m-tolyl-[1,4]diazepan-1-yl)-propionylamino]-adamantane-1-carboxylic acid;
(E)-4-[2-methyl-2-(4-phenyl-piperidin-1-yl)-propionylamino]-adamantane-1-carboxylic acid;
(E)-4-{2-[4-(4-chloro-phenyl)-piperidin-1-yl]-2-methyl-propionylamino}-adamantane-1-carboxylic acid;
(E)-4-{2-[5-(6-chloro-pyridin-3-yl)-hexahydro-pyrrolo[3,4-c]pyrrol-2-yl]-2-methyl-propionylamino}-adamantane-1-carboxyamide;
(E)-4-{2-[4-(5-fluoro-pyridin-3-yl)-[1,4]diazepan-1-yl]-2-methyl-propionylamino}-adamantane-1-carboxyamide;
(E)-4-[2-methyl-2-(3-pyridin-3-yl-3,9-diazbicyclo[4.2.1]non-9-yl)-propionylamino]-adamantane-1-carboxyamide;
(E)-4-[2-methyl-2-(2-trifluoromethyl-pyrrolidin-1-yl)-propionylamino]-adamantane-1-carboxyamide;
(E)-4-[2-(3,3-difluoro-piperidin-1-yl)-2-methyl-propionylamino]-adamantane-1-carboxyamide;
(E)-4-[2-(3-fluoro-pyrrolidin-1-yl)-2-methyl-propionylamino]-adamantane-1-carboxyamide;
(E)-4-{2-[4-(5-trifluormethyl-pyridin-2-yl)-piperazin-1-yl]-acetylamino}-adamantane-1-carboxamide;
(E)-4-[2-(3,3-difluoro-piperidin-1-yl)-2-methyl-propionylamino]-adamantane-1-carboxylic acid 3,4-dimethoxybenzylamide;
(E)-4-[({4-[2-(3,3-difluoro-piperidin-1-yl)-2-methyl-propionylamino]-adamantane-1-carbonyl}-amino)-methyl]-benzoic acid;
(E)-4-[2-(3,3-difluoro-piperidin-1-yl)-2-methyl-propionylamino]-adamantane-1-carboxylic acid (furan-2-ylmethyl)-amide;
(E)-4-[2-(3,3-difluoro-piperidin-1-yl)-2-methyl-propionylamino]-adamantane-1-carboxylic acid (thiazol-5-ylmethyl)-amide;
(E)-4-[2-(3,3-difluoro-piperidin-1-yl)-2-methyl-propionylamino]-adamantane-1-carboxylic acid 2-methoxybenzylamide;
(E)-4-(2-methyl-2-phenylamino-propionylamino)-adamantane-1-carboxyamide;
(E)-4-[2-methyl-2-(3-pyridin-3-yl-3,9-diazbicyclo[4.2.1]non-9-yl)-propionylamino]-adamantane-1-carboxyamide;
(E)-4-{2-methyl-2-[5-(3-trifluoromethyl-phenyl)-[1,5]diazocan-1-yl]-propionylamino}-adamantane-1-carboxylic acid;
(E)-4-{2-[7-(5-bromo-pyridin-2-yl)-3,7-diazbicyclo[3.3.1]non-3-yl]-2-methyl-propionylamino}-adamantane-1-carboxyamide;
$N^2$-[2-(4-chlorophenyl)ethyl]-$N^1$-[(E)-5-hydroxy-2-adamantyl]alaninamide;
2-(4-benzylpiperidin-1-yl)-N-[(E)-5-hydroxy-2-adamantyl]propanamide;
N-[(E)-5-hydroxy-2-adamantyl]-2-(6,7,9,10-tetrahydro-8H-[1,3]dioxolo[4,5-g][3]benzazepin-8-yl)propanamide;
N-[(E)-5-hydroxy-2-adamantyl]-2-(4-pyridin-2-ylpiperazin-1-yl)propanamide;
2-[4-(4-fluorophenyl)piperazin-1-yl]-N-[(E)-5-hydroxy-2-adamantyl]propanamide;
N-[(E)-5-hydroxy-2-adamantyl]-2-[4-(4-methoxyphenyl)piperazin-1-yl]propanamide;
2-[4-(5-cyanopyridin-2-yl)piperazin-1-yl]-N-[(E)-5-hydroxy-2-adamantyl]propanamide;
2-[4-(2-furoyl)piperazin-1-yl]-N-[(1R,3S)-5-hydroxy-2-adamantyl]propanamide;
2-(1,3-dihydro-2H-isoindol-2-yl)-N-[(E)-5-hydroxy-2-adamantyl]propanamide;
N-[(E)-5-hydroxy-2-adamantyl]-2-{4-[4-(trifluoromethyl)phenyl]piperazin-1-yl}(2S)—N-[(E)-5-hydroxy-2-adamantyl]-2-{4-[5-(trifluoromethyl)pyridin-2-yl]piperazin-1-yl}propanamide;
(2R)—N-[(E)-5-hydroxy-2-adamantyl]-2-{4-[5-(trifluoromethyl)pyridin-2-yl]piperazin-1-yl}propanamide;
2-[3-(4-chlorophenoxy)azetidin-1-yl]-N-[(E)-5-hydroxy-2-adamantyl]propanamide;
2-[4-(2-fluorophenoxy)piperidin-1-yl]-N-[(E)-5-hydroxy-2-adamantyl]propanamide;
2-[3-(2-fluorophenoxy)piperidin-1-yl]-N-[(E)-5-hydroxy-2-adamantyl]propanamide;
2-[3-(3-fluorophenoxy)pyrrolidin-1-yl]-N-[(E)-5-hydroxy-2-adamantyl]propanamide;
$N^2$-[2-(3,4-dichlorophenyl)ethyl]-$N^1$-[(E)-5-hydroxy-2-adamantyl]-$N^2$-methylalaninamide;

N²-[2-(4-chlorophenyl)-1-methylethyl]-N¹-[(E)-5-hydroxy-2-adamantyl]-N²-methylalaninamide;

2-(5-chloro-2,3-dihydro-1H-indol-1-yl)-N-[(E)-5-hydroxy-2-adamantyl]propanamide;

2-[4-(6-chloropyridin-3-yl)piperazin-1-yl]-N-[(E)-5-hydroxy-2-adamantyl]propanamide;

N-[(E)-5-hydroxy-2-adamantyl]-2-(3-phenylazetidin-1-yl)propanamide;

(E)-N-methyl-4-[(2-methyl-2-{4-[5-(trifluoromethyl)pyridin-2-yl]piperazin-1-yl}propanoyl)amino]adamantane-1-carboxamide;

(E)-N-methoxy-4-[(2-methyl-2-{4-[5-(trifluoromethyl)pyridin-2-yl]piperazin-1-yl}propanoyl)amino]adamantane-1-carboxamide;

N-[(E)-5-(aminomethyl)-2-adamantyl]-2-methyl-2-{4-[5-(trifluoromethyl)pyridin-2-yl]piperazin-1-yl}propanamide;

N-[(E)-5-hydroxy-2-adamantyl]-1-{[4-(trifluoromethyl)benzyl]amino}cyclopropanecarboxamide;

N-[(E)-5-cyano-2-adamantyl]-2-methyl-2-{4-[5-(trifluoromethyl)pyridin-2-yl]piperazin-1-yl}propanamide;

N-[(E)-5-hydroxy-2-adamantyl]-1-piperidin-1-ylcyclopropanecarboxamide;

2-methyl-N-[(E)-5-(5-methyl-1,2,4-oxadiazol-3-yl)-2-adamantyl]-2-{4-[5-(trifluoromethyl)pyridin-2-yl]piperazin-1-yl}propanamide;

2-methyl-N-[(E)-5-(2H-tetraazol-5-yl)-2-adamantyl]-2-{4-[5-(trifluoromethyl)pyridin-2-yl]piperazin-1-yl}propanamide;

(E)-4-[(2-{4-[[(4-chlorophenyl)sulfonyl](cyclopropyl)amino]piperidin-1-yl}propanoyl)amino]adamantane-1-carboxamide;

N-[(E)-5-hydroxy-2-adamantyl]-2-methyl-2-[2-(trifluoromethyl)pyrrolidin-1-yl]propanamide;

(E)-4-({2-[(3S)-3-fluoropyrrolidin-1-yl]-2-methylpropanoyl}amino)adamantane-1-carboxamide;

methyl(E)-4-{[2-methyl-2-(4-pyridin-2-ylpiperazin-1-yl)propanoyl]amino}adamantane-1-carboxylate;

(E)-4-{[2-methyl-2-(4-pyridin-2-ylpiperazin-1-yl)propanoyl]amino}adamantane-1-carboxylic acid;

(E)-4-({2-methyl-2-[(2S)-2-methyl-4-pyridin-2-ylpiperazin-1-yl]propanoyl}amino)adamantane-1-carboxylic acid;

(E)-4-{[2-methyl-2-(4-pyridin-2-ylpiperazin-1-yl)propanoyl]amino}adamantane-1-carboxamide;

2-methyl-N-[(E)-5-(4H-1,2,4-triazol-3-yl)-2-adamantyl]-2-{4-[5-(trifluoromethyl)pyridin-2-yl]piperazin-1-yl}propanamide;

(E)-4-{[2-(3,3-difluoropiperidin-1-yl)-2-methylpropanoyl]amino}-N-(pyridin-4-ylmethyl)adamantane-1-carboxamide;

(E)-4-[(2-methyl-2-{4-[4-(trifluoromethyl)phenyl]piperazin-1-yl}propanoyl)amino]adamantane-1-carboxylic acid;

(E)-4-({2-methyl-2-[(2R)-2-methyl-4-(5-methylpyridin-2-yl)piperazin-1-yl]propanoyl}amino)adamantane-1-carboxylic acid;

(E)-4-({2-[(3S)-3-fluoropiperidin-1-yl]propanoyl}amino)adamantane-1-carboxamide;

(E)-4-[((2S)-2-{4-[5-(trifluoromethyl)pyridin-2-yl]piperazin-1 propanoyl)amino]adamantane-1-carboxamide;

(E)-4-[((2R)-2-{4-[5-(trifluoromethyl)pyridin-2-yl]piperazin-1-yl}propanoyl)amino]adamantane-1-carboxamide;

(E)-4-[({2-(trifluoromethyl)-4-[5-(trifluoromethyl)pyridin-2-yl]piperazin-1-yl}acetyl)amino]adamantane-1-carboxamide;

(E)-4-[(cyclopropyl{4-[5-(trifluoromethyl)pyridin-2-yl]piperazin-1-yl}acetyl)amino]adamantane-1-carboxylic acid;

(E)-4-{[(1-{4-[5-(trifluoromethyl)pyridin-2-yl]piperazin-1-yl}cyclobutyl)carbonyl]amino}adamantane-1-carboxylic acid;

(E)-4-({2-[9-(6-chloropyridin-3-yl)-3,9-diazabicyclo[4.2.1]non-3-yl]-2-methylpropanoyl}amino)adamantane-1-carboxamide;

(E)-4-({2-[4-(2,3-dichlorophenyl)piperazin-1-yl]-2-methylpropanoyl}amino)adamantane-1-carboxylic acid;

(E)-4-{[2-methyl-2-(4-phenylpiperazin-1-yl)propanoyl]amino}adamantane-1-carboxylic acid;

(E)-4-({2-methyl-2-[4-(4-methylphenyl)piperazin-1-yl]propanoyl}amino)adamantane-1-carboxylic acid;

(E)-4-({2-[4-(1,3-benzothiazol-2-yl)piperazin-1-yl]-2-methylpropanoyl}amino)adamantine-1-carboxylic acid;

(E)-4-({2-[4-(3,4-dichlorophenyl)piperazin-1-yl]-2-methylpropanoyl}amino)adamantane-1-carboxylic acid;

(E)-4-({2-methyl-2-[4-(3-methylphenyl)piperazin-1-yl]propanoyl}amino)adamantane-1-carboxylic acid;

(E)-4-[(2-methyl-2-{4-[2-(trifluoromethyl)phenylpiperazin-1-yl}propanoyl)amino]adamantane-1-carboxylic acid;

(E)-4-({2-[4-(2,4-difluorophenyl)piperazin-1-yl]-2-methylpropanoyl}amino)adamantane-1-carboxylic acid;

(E)-4-({2-methyl-2-[4-(6-methylpyridin-2-yl)piperazin-1-yl]propanoyl}amino)adamantane-1-carboxylic acid;

(E)-4-{[2-methyl-2-(4-pyrimidin-2-ylpiperazin-1-yl)propanoyl]amino}adamantane-1-carboxylic acid;

(E)-4-({2-[4-(4-fluorophenyl)piperazin-1-yl]-2-methylpropanoyl}amino)adamantane-1-carboxylic acid;

(E)-4-[(2-methyl-2-{4-[3-(trifluoromethyl)phenyl]piperazin-1-yl}propanoyl)amino]adamantane-1-carboxylic acid;

(E)-4-[(2-methyl-2-{4-[3-(trifluoromethyl)pyridin-2-yl]piperazin-1-yl}propanoyl)amino]adamantane-1-carboxylic acid;

(E)-4-({2-[4-(3-chlorophenyl)piperazin-1-yl]-2-methylpropanoyl}amino)adamantane-1-carboxylic acid;

(E)-4-({2-[4-(4-acetylphenyl)piperazin-1-yl]-2-methylpropanoyl}amino)adamantane-1-carboxylic acid;

(E)-N,N-dimethyl-4-[(2-methyl-2-{4-[5-(trifluoromethyl)pyridin-2-yl]piperazin-1-yl}propanoyl)amino]adamantane-1-carboxamide;

N-[(E)-5-(acetylamino)-2-adamantyl]-2-{4-[5-(trifluoromethyl)pyridin-2-yl]piperazin-1-yl}propanamide;

(E)-4-{[2-methyl-2-(4-pyrimidin-2-ylpiperazin-1-yl)propanoyl]amino}adamantane-1-carboxamide;

(E)-4-{[2-methyl-2-(4-pyrazin-2-ylpiperazin-1-yl)propanoyl]amino}adamantane-1-carboxamide;

(E)-4-({2-[4-(4-fluorophenyl)piperazin-1-yl]-2-methylpropanoyl}amino)adamantane-1-carboxamide;

(E)-4-({2-[4-(3-cyanopyridin-2-yl)piperazin-1-yl]-2-methylpropanoyl}amino)adamantane-1-carboxamide;

(E)-4-({2-[4-(6-methylpyridin-3-yl)-1,4-diazepan-1-yl]propanoyl}amino)adamantane-1-carboxamide;

(E)-4-[(2-{4-[3-chloro-5-(trifluoromethyl)pyridin-2-yl]piperazin-1-yl}-2-methylpropanoyl)amino]adamantane-1-carboxylic acid;

4-(2-{[((E)-4-{[2-(3,3-difluoropiperidin-1-yl)-2-methylpropanoyl]amino}-1-adamantyl)carbonyl]amino}ethyl)benzoic acid;

N-{(E)-5-[(methylsulfonyl)amino]-2-adamantyl}-2-{4-[5-(trifluoromethyl)pyridin-2-yl]piperazin-1-yl}propanamide;

N-[(E)-5-(1-hydroxy-1-methylethyl)-2-adamantyl]-2-methyl-2-{4-[5-(trifluoromethyl)pyridin-2-yl]piperazin-1-yl}propanamide;

(E)-4-{[2-methyl-2-(4-phenylpiperazin-1-yl)propanoyl]
   amino}adamantane-1-carboxamide;
(E)-4-({2-[4-(2-methoxyphenyl)piperazin-1-yl]-2-
   methylpropanoyl}amino)adamantane-1-carboxamide;
(E)-4-[(N,2-dimethyl-N-phenylalanyl)amino]adamantane-
   1-carboxamide;
(E)-4-({2-[4-(2,4-dimethoxyphenyl)piperazin-1-yl]-2-
   methylpropanoyl}amino)adamantine-1-carboxamide;
(E)-4-({2-[4-(2,3-dicyanophenyl)piperazin-1-yl]-2-
   methylpropanoyl}amino)adamantane-1-carboxamide;
N-[(E)-5-(cyanomethyl)-2-adamantyl]-2-methyl-2-{4-[5-
   (trifluoromethyl)pyridin-2-yl]piperazin-1-
   yl}propanamide;
(E)-4-({2-methyl-2-[4-(4-nitrophenyl)piperazin-1-yl]
   propanoyl}amino)adamantane-1-carboxylic acid;
(E)-4-({2-[4-(2,4-dichlorophenyl)piperazin-1-yl]-2-
   methylpropanoyl}amino)adamantane-1-carboxylic acid;
{(E)-4-[(2-methyl-2-{4-[5-(trifluoromethyl)pyridin-2-yl]
   piperazin-1-yl}propanoyl)amino]-1-adamantyl}acetic
   acid;
(E)-4-({2-[4-(4-chloro-2-fluorophenyl)piperazin-1-yl]-2-
   methylpropanoyl}amino)adamantane-1-carboxylic acid;
(E)-4-[(2-methyl-2-{4-[4-(trifluoromethyl)pyrimidin-2-yl]
   piperazin-1-yl}propanoyl)amino]adamantane-1-carbox-
   ylic acid;
(E)-4-({2-[4-(3-chloro-4-fluorophenyl)piperazin-1-yl]-2-
   methylpropanoyl}amino)adamantane-1-carboxylic acid;
(E)-4-({2-[4-(4-cyanophenyl)piperazin-1-yl]-2-
   methylpropanoyl}amino)adamantane-1-carboxylic acid;
(E)-4-({2-[4-(4-bromophenyl)piperazin-1-yl]-2-
   methylpropanoyl}amino)adamantane-1-carboxylic acid;
(E)-4-({2-[4-(5-chloro-2-methoxyphenyl)piperazin-1-yl]-2-
   methylpropanoyl}amino)adamantane-1-carboxylic acid;
(E)-4-({2-[4-(2-chlorophenyl)piperazin-1-yl]-2-
   methylpropanoyl}amino)adamantane-1-carboxylic acid;
(E)-4-({2-[4-(2-cyanophenyl)piperazin-1-yl]-2-
   methylpropanoyl}amino)adamantane-1-carboxylic acid;
(E)-4-({2-[4-(2-fluorophenyl)piperazin-1-yl]-2-
   methylpropanoyl}amino)adamantane-1-carboxylic acid;
(E)-4-({2-methyl-2-[4-(2-methylphenyl)piperazin-1-yl]
   propanoyl}amino)adamantane-1-carboxylic acid;
(E)-4-({2-[4-(4-chlorophenyl)piperazin-1-yl]-2-
   methylpropanoyl}amino)adamantane-1-carboxylic acid;
(E)-4-({2-[4-(3-chloropyridin-2-yl)piperazin-1-yl]-2-
   methylpropanoyl}amino)adamantine-1-carboxylic acid;
(E)-4-[(2-{4-[2-chloro-4-(trifluoromethyl)phenyl]piper-
   azin-1-yl}-2-methylpropanoyl)amino]adamantane-1-car-
   boxylic acid;
(E)-4-({2-[(3R)-3-fluoropyrrolidin-1-yl]-2-
   methylpropanoyl}amino)-N-(pyridin-3-ylmethyl)ada-
   mantane-1-carboxamide;
(E)-4-{[2-methyl-2-(3-phenylpiperidin-1-yl)propanoyl]
   amino}adamantane-1-carboxamide;
(E)-4-({2-[4-(2-chloro-4-methylphenyl)piperazin-1-yl]-2-
   methylpropanoyl}amino)adamantane-1-carboxylic acid;
(E)-4-({2-[4-(2-fluorophenyl)piperidin-1-yl]-2-
   methylpropanoyl}amino)adamantane-1-carboxylic acid;
(E)-4-({2-methyl-2-[4-(2-methylphenyl)piperidin-1-yl]
   propanoyl}amino)adamantane-1-carboxylic acid;
(E)-4-({2-[4-(2-chloro-4-fluorophenyl)piperazin-1-yl]-2-
   methylpropanoyl}amino)adamantane-1-carboxamide;
(E)-4-({2-[4-(2-furoyl)piperazin-1-yl]-2-
   methylpropanoyl}amino)adamantane-1-carboxylic acid;
(E)-4-({2-[4-(2-chloro-4-cyanophenyl)piperazin-1-yl]-2-
   methylpropanoyl}amino)adamantane-1-carboxylic acid;
(E)-4-({2-[4-(2-chloro-4-fluorophenyl)piperazin-1-yl]-2-
   methylpropanoyl}amino)adamantane-1-carboxylic acid;
(E)-4-[(2-methyl-2-{4-[5-(trifluoromethyl)pyridin-2-yl]pip-
   erazin-1-yl}propanoyl)amino]-1-adamantyl carbamate;
(E)-4-[(2-{4-[(4-chlorophenyl)sulfonyl]piperazin-1-yl}-2-
   methylpropanoyl)amino]adamantane-1-carboxylic acid;
(E)-4-({2-[4-(2,4-difluorophenyl)piperidin-1-yl]-2-
   methylpropanoyl}amino)adamantane-1-carboxylic acid;
(E)-4-({2-[4-(4-cyano-2-fluorophenyl)piperazin-1-yl]-2-
   methylpropanoyl}amino)adamantane-1-carboxylic acid;
(E)-4-[(2-methyl-2-{3-methyl-4-[5-(trifluoromethyl)pyri-
   din-2-yl]piperazin-1-yl}propanoyl)amino]adamantane-1-
   carboxylic acid;
(E)-4-({2-[4-(4-cyanophenyl)-3,5-dimethyl-1H-pyrazol-1-
   yl]-2-methylpropanoyl}amino)adamantane-1-carboxylic
   acid;
(E)-4-({2-[4-(4-cyanophenyl)-3,5-dimethyl-1H-pyrazol-1-
   yl]-2-methylpropanoyl}amino)adamantane-1-carboxam-
   ide;
(E)-4-{[2-methyl-N-(3-methylphenyl)alanyl]
   amino}adamantane-1-carboxamide;
tert-butyl 4-(2-{[(E)-5-(aminocarbonyl)-2-adamantyl]
   amino}-1,1-dimethyl-2-oxoethyl)piperazine-1-carboxy-
   late;
(2R)-2-[(3R)-3-fluoropyrrolidin-1-yl]-N-[(E)-5-hydroxy-2-
   adamantyl]propanamide;
(E)-4-({2-[4-(2-bromophenyl)piperazin-1-yl]-2-
   methylpropanoyl}amino)adamantane-1-carboxylic acid;
(E)-4-{[N-(3-chlorophenyl)-2-methylalanyl]
   amino}adamantane-1-carboxamide;
(E)-4-{[N-(3-methoxyphenyl)-2-methylalanyl]
   amino}adamantane-1-carboxamide;
(E)-4-({2-[4-(4-cyanophenyl)-3,5-dimethyl-1H-pyrazol-1-
   yl]-2-methylpropanoyl}amino)-N-(1,3-thiazol-5-ylm-
   ethyl)adamantane-1-carboxamide;
(E)-4-({2-[4-(6-chloropyrimidin-4-yl)piperazin-1-yl]-2-
   methylpropanoyl}amino)adamantane-1-carboxylic acid;
(E)-4-({2-[4-(6-chloropyridazin-3-yl)piperazin-1-yl]-2-
   methylpropanoyl}amino)adamantane-1-carboxylic acid;
(E)-4-({2-[4-(2-chloropyrimidin-4-yl)piperazin-1-yl]-2-
   methylpropanoyl}amino)adamantane-1-carboxylic acid;
N-[({(E)-4-[(2-methyl-2-{4-[5-(trifluoromethyl)pyridin-2-
   yl]piperazin-1-yl}propanoyl)amino]-1-
   adamantyl}amino)carbonyl]glycine;
(E)-4-({2-[4-(5-cyanopyridin-2-yl)piperazin-1-yl]-2-
   methylpropanoyl}amino)adamantine-1-carboxylic acid;
(E)-4-({2-[4-(3-chloro-5-cyanopyridin-2-yl)piperazin-1-
   yl]-2-methylpropanoyl}amino)adamantane-1-carboxylic
   acid;
(E)-4-({2-methyl-2-[4-(1,3-thiazol-2-yl)piperazin-1-yl]
   propanoyl}amino)adamantane-1-carboxylic acid;
(E)-4-{[N-(4-methoxyphenyl)-2-methylalanyl]
   amino}adamantane-1-carboxamide;
(E)-4-({N-[4-(dimethylamino)phenyl]-2-
   methylalanyl}amino)adamantane-1-carboxamide;
(E)-4-({2-methyl-N-[4-(trifluoromethyl)phenyl]
   alanyl}amino)adamantane-1-carboxamide;
(E)-4-({2-methyl-N-[3-(trifluoromethyl)phenyl]
   alanyl}amino)adamantane-1-carboxamide;
(E)-4-({2-[4-(2-hydroxyphenyl)piperazin-1-yl]-2-
   methylpropanoyl}amino)adamantane-1-carboxylic acid;
4-(2-{[(E)-5-(aminocarbonyl)-2-adamantyl]amino}-1,1-di-
   methyl-2-oxoethyl)-N-(tert-butyl)piperazine-1-carbox-
   amide; and
N-[(E)-5-(formylamino)-2-adamantyl]-2-methyl-2-{4-[5-
   (trifluoromethyl)pyridin-2-yl]piperazin-1-
   yl}propanamide.

Also included in the present application are selective 11β-HSD1 inhibitors that can be selected from a group of compounds having formula (II),

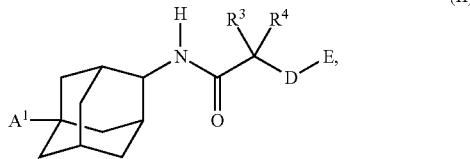

(II)

wherein $A^1$, is selected from the group consisting of hydrogen, alkenyl, alkyl, alkyl-NH-alkyl, alkylcarbonyl, alkylsulfonyl, carboxyalkyl, carboxycycloalkyl, cyano, cycloalkyl, cycloalkylcarbonyl, cycloalkylsulfonyl, aryl, arylalkyl, aryloxyalkyl, arylcarbonyl, arylsulfonyl, heteroaryl, heteroarylalkyl, heteroaryloxyalkyl, heteroarylsulfonyl, heterocycle, heterocyclealkyl, heterocycleoxyalkyl, heterocyclesulfonyl, halogen, haloalkyl, $-NR^5-[C(R^6R^7)]_n-C(O)-R^8$, $-O-[C(R^9R^{10})]_p-C(O)-R^{11}$, $-OR^{12}$, $-S$-alkyl, $-S(O)$-alkyl, $-N(R^{13}R^{14})$, $-CO_2R^{15}$, $-C(O)-N(R^{16}R^{17})$, $-C(R^{18}R^{19})-OR^{20}$, $-C(R^{21}R^{22})-N(R^{23}R^{24})$, $-C(=NOH)-N(H)_2$, $-C(R^{18a}R^{19a})-C(O)N(R^{23}R^{24})$, $-S(O)_2-N(R^{25}R^{26})$, and $-C(R^{18a}R^{19a})-S(O)_2-N(R^{25}R^{26})$;

$R^{18a}$ and $R^{19a}$ are each independently selected from the group consisting of hydrogen and alkyl;

n is 0 or 1;

p is 0 or 1;

D is a member selected from the group consisting of a $-O-$, $-S-$, $-S(O)-$ and $-S(O)_2-$; E is a member selected from the group consisting of alkyl, alkoxyalkyl, carboxyalkyl, carboxycycloalkyl, cycloalkyl, cycloalkylalkyl, aryl, arylalkyl, haloalkyl, heteroaryl, heteroarylalkyl, heterocycle, heterocyclealkyl, or $R^4$ and E taken together with the atoms to which they are attached form a heterocycle;

$R^3$ and $R^4$ are each independently selected from the group consisting of hydrogen, alkyl, carboxyalkyl, carboxycycloalkyl, cycloalkyl, haloalkyl, aryl, arylalkyl, heteroaryl, heteroarylalkyl, heterocycle and heterocyclealkyl, or $R^3$ and $R^4$ taken together with the atoms to which they are attached form a ring selected from the group consisting of cycloalkyl and heterocycle;

$R^5$ is a member selected from the group consisting of hydrogen, alkyl, carboxyalkyl, cycloalkyl, carboxycycloalkyl, aryl, arylalkyl, aryloxyalkyl, hydroxy, alkoxy, heteroaryl, heteroarylalkyl, heteroaryloxyalkyl, heterocycle, heterocyclealkyl and heterocycleoxyalkyl;

$R^6$ and $R^7$ are each independently selected from the group consisting of hydrogen and alkyl, or $R^6$ and $R^7$ taken together with the atom to which they are attached form a ring selected from the group consisting of cycloalkyl and heterocycle;

$R^8$ is selected from the group consisting of hydrogen, alkyl, carboxy, carboxyalkyl, cycloalkyl, carboxycycloalkyl, aryl, arylalkyl, aryloxy, aryloxyalkyl, hydroxy, alkoxy, cycloalkyloxy, heteroaryl, heteroarylalkyl, heteroaryloxy, heteroaryloxyalkyl, heterocycle, heterocyclealkyl, heterocycleoxy, heterocycleoxyalkyl and $-N(R^{27}R^{28})$;

$R^9$ and $R^{10}$ are each independently selected from the group consisting of hydrogen and alkyl, or $R^9$ and $R^{10}$ taken together with the atom to which they are attached form a ring selected from the group consisting of cycloalkyl and heterocycle;

$R^{11}$ is selected from the group consisting of hydroxy and $-N(R^{29}R^{30})$;

$R^{12}$ is selected from the group consisting of hydrogen, alkyl, carboxyalkyl, cycloalkyl, carboxycycloalkyl, aryl, arylalkyl, aryloxyalkyl, haloalkyl, heteroaryl, heteroarylalkyl, heteroaryloxyalkyl, heterocycle, heterocyclealkyl and heterocycleoxyalkyl;

$R^{13}$ and $R^{14}$ are each independently selected from the group consisting of hydrogen, alkyl, alkylsufonyl, aryl, arylalkyl, aryloxyalkyl, arylsulfonyl, carboxyalkyl, cycloalkyl, carboxycycloalkyl, cycloalkylsulfonyl, heteroaryl, heteroarylalkyl, heteroaryloxyalkyl, heteroarylsulfonyl, heterocycle, heterocyclealkyl, heterocycleoxyalkyl and heterocyclesulfonyl;

$R^{15}$ is selected from the group consisting of hydrogen, alkyl, carboxyalkyl, cycloalkyl, carboxycycloalkyl, aryl, arylalkyl, aryloxyalkyl, heteroaryl, heteroarylalkyl, heteroaryloxyalkyl, heterocycle, heterocyclealkyl and heterocycleoxyalkyl;

$R^{16}$ and $R^{17}$ are each independently selected from the group consisting of hydrogen, alkyl, alkoxy, alkylsufonyl, aryl, arylalkyl, aryloxy, aryloxyalkyl, arylsulfonyl, carboxy, carboxyalkyl, carboxycycloalkyl, cycloalkyl, cycloalkyloxy, cycloalkylsulfonyl, heteroaryl, heteroarylalkyl, heteroaryloxyalkyl, heteroaryloxy, heteroarylsulfonyl, heterocycle, heterocyclealkyl, heterocycleoxyalkyl, heterocycleoxy, heterocyclesulfonyl, hydroxy, and alkyl-C(O)N($R^{201}R^{202}$), or, $R^{16}$ and $R^{17}$ taken together with the atom to which they are attached form a heterocycle;

$R^{201}$ and $R^{202}$ are independently selected from the group consisting of hydrogen and alkyl;

$R^{18}$, $R^{19}$ and $R^{20}$ are each independently selected from the group consisting of hydrogen, alkyl, aryl, arylalkyl, carboxyalkyl, carboxycycloalkyl, cycloalkyl, haloalkyl, heteroaryl, heteroarylalkyl, heterocycle and heterocyclealkyl;

$R^{21}$ and $R^{22}$ are each independently selected from the group consisting of hydrogen, alkyl, alkylcarbonyl, alkylsulfonyl, aryl, arylcarbonyl, arylsulfonyl, cycloalkyl, carboxyalkyl, carboxycycloalkyl, cycloalkylcarbonyl, cycloalkylsulfonyl, heteroaryl, heteroarylcarbonyl, heteroarylsulfonyl, heterocycle, heterocyclecarbonyl and heterocyclesulfonyl;

$R^{23}$ and $R^{24}$ are each independently selected from the group consisting of hydrogen, alkyl, alkylcarbonyl, alkoxy, alkylsulfonyl, aryl, arylcarbonyl, aryloxy, arylsulfonyl, carboxyalkyl, carboxycycloalkyl, cycloalkyl, cycloalkylcarbonyl, cycloalkyloxy, cycloalkylsulfonyl, heteroaryl, heteroarylcarbonyl, heteroaryloxy, heteroarylsulfonyl, heterocycle, heterocyclecarbonyl, heterocycleoxy, heterocyclesulfonyl and hydroxy, or, $R^{23}$ and $R^{24}$ taken together with the atom to which they are attached form a ring selected from the group consisting of heteroaryl and heterocycle;

$R^{25}$ and $R^{26}$ are each independently selected from the group consisting of hydrogen, alkyl, alkoxy, alkylsufonyl, aryl, arylalkyl, aryloxy, aryloxyalkyl, arylsulfonyl, carboxy, carboxyalkyl, carboxycycloalkyl, cycloalkyl, cycloalkyloxy, cycloalkylsulfonyl, heteroaryl, heteroarylalkyl, heteroaryloxyalkyl, heteroaryloxy, heteroarylsulfonyl, heterocycle, heterocyclealkyl, heterocycleoxyalkyl, heterocycleoxy, heterocyclesulfonyl, and hydroxy, or, $R^{25}$ and $R^{26}$ taken together with the atom to which they are attached form a heterocycle;

$R^{27}$ and $R^{28}$ are each independently selected from the group consisting of hydrogen, alkyl, alkoxy, alkylsulfonyl, aryl, arylalkyl, aryloxy, aryloxyalkyl, arylsulfonyl, carboxy, carboxyalkyl, cycloalkyl, cycloalkyloxy, carboxycycloalkyl, cycloalkylsulfonyl, heteroaryl, heteroarylalkyl, heteroaryloxy, heteroaryloxyalkyl, heteroarylsulfonyl, heterocycle, heterocyclealkyl, heterocycleoxy, heterocycleoxyalkyl, heterocyclesulfonyl and hydroxy, or, $R^{27}$ and $R^{28}$ taken together with the atom to which they are attached form a heterocycle; and $R^{29}$ and $R^{30}$ are each independently selected from the group consisting of hydrogen, alkyl, alkoxy, alkylsufonyl, aryl, arylalkyl, aryloxy, aryloxyalkyl, arylsulfonyl, carboxy, carboxyalkyl, cycloalkyl, cycloalkyloxy, carboxycycloalkyl, cycloalkylsulfonyl, heteroaryl, heteroarylalkyl, heteroaryloxy, heteroaryloxyalkyl, heteroarylsulfonyl, heterocycle, heterocyclealkyl, heterocycleoxy, heterocycleoxyalkyl, heterocyclesulfonyl, and hydroxy, or, $R^{29}$ and $R^{30}$ taken together with the atom to which they are attached form a heterocycle; provided that, if $R^1$ is hydrogen; then at least one of $A^1$, $A^2$, $A^3$ and $A^4$ is not hydrogen;

or a pharmaceutically acceptable metabolite, salt, prodrug, salt of a prodrug, or a combination thereof.

Examples of compounds of formula (II) that can be used in the methods of the invention are (E)-4-[(2-methyl-2-phenoxypropanoyl)amino]adamantane-1-carboxamide;

(E)-4-[(2-methyl-2-{[4-(trifluoromethyl)benzyl]oxy}propanoyl)amino]adamantane-1-carboxamide;

(E)-4-({2-methyl-2-[(2-methylcyclohexyl)oxy]propanoyl}amino)adamantane-1-carboxylic acid;

(E)-4-({2-methyl-2-[(3-methylcyclohexyl)oxy]propanoyl}amino)adamantane-1-carboxylic acid;

(E)-4-{[2-(cycloheptyloxy)-2-methylpropanoyl]amino}adamantane-1-carboxylic acid;

(E)-4-{[2-(cyclohexylmethoxy)-2-methylpropanoyl]amino}adamantane-1-carboxylic acid;

(E)-4-{[2-(4-chlorophenoxy)-2-methylpropanoyl]amino}adamantane-1-carboxylic acid;

(E)-4-{[2-(4-chlorophenoxy)-2-methylpropanoyl]amino}adamantane-1-carboxamide;

(E)-4-({2-methyl-2-[(4-methylcyclohexyl)oxy]propanoyl}amino)adamantane-1-carboxamide;

(E)-4-[(2-phenoxypropanoyl)amino]adamantane-1-carboxamide;

(E)-4-{[2-methyl-2-(2-methylphenoxy)propanoyl]amino}adamantane-1-carboxylic acid;

(E)-4-{[2-methyl-2-(4-methylphenoxy)propanoyl]amino}adamantane-1-carboxylic acid;

(E)-4-{[2-(2-chlorophenoxy)-2-methylpropanoyl]amino}adamantane-1-carboxylic acid;

(E)-4-{[2-(2-methoxyphenoxy)-2-methylpropanoyl]amino}adamantane-1-carboxamide;

(E)-4-{[2-(4-methoxyphenoxy)-2-methylpropanoyl]amino}adamantane-1-carboxamide;

(E)-4-({2-methyl-2-[3-(trifluoromethyl)phenoxy]propanoyl}amino)adamantane-1-carboxamide;

(E)-4-{[2-(3-methoxyphenoxy)-2-methylpropanoyl]amino}adamantane-1-carboxamide;

(E)-2-(4-chloro-phenoxy)-N-(5-hydroxy-adamantan-2-yl)-2-methyl-propionamide;

(E)-{[2-methyl-2-(4-methylphenoxy)propanoyl]amino}adamantane-1-carboxamide;

(E)-4-{[2-(3-chlorophenoxy)-2-methylpropanoyl]amino}adamantane-1-carboxamide;

(E)-4-({2-methyl-2-[4-(trifluoromethoxy)phenoxy]propanoyl}amino)adamantane-1-carboxamide;

(E)-4-{[2-(3-bromophenoxy)-2-methylpropanoyl]amino}adamantane-1-carboxylic acid;

4-({[((E)-4-{[2-(4-chlorophoxy)-2-methylpropanoyl]amino}-1-adamantyl)carbonyl]amino}methyl)benzoic acid;

(E)-4-{[2-(2,3-dimethylphenoxy)-2-methylpropanoyl]amino}adamantane-1-carboxylic acid;

tert-butyl 4-(2-{[(E)-5-(aminocarbonyl)-2-adamantyl]amino}-1,1-dimethyl-2-oxoethoxy)phenylcarbamate;

(E)-N-[4-(aminocarbonyl)benzyl]-4-{[2-(4-chlorophenoxy)-2-methylpropanoyl]amino}adamantane-1-carboxamide;

(E)-N-[4-(aminocarbonyl)methyl]-4-{[2-(4-chlorophenoxy)-2-methylpropanoyl]amino}adamantane-1-carboxamide;

3-({[((E)-4-{[2-(4-chlorophenoxy)-2-methylpropanoyl amino}-1-adamantyl)carbonyl]amino}methyl)benzoic acid;

(E)-4-({2-[(5-bromopyridin-2-yl)oxy]-2-methylpropanoyl}amino)adamantane-1-carboxamide;

(E)-4-{[2-(2-cyanophenoxy)-2-methylpropanoyl]amino}adamantane-1-carboxamide;

(E)-4-{[2-(4-hydroxyphenoxy)-2-methylpropanoyl]amino}adamantane-1-carboxamide;

((E)-4-{[2-(4-chlorophenoxy)-2-methylpropanoyl]amino}-1-adamantyl)acetic acid;

N-[(E)-5-(2-amino-2-oxoethyl)-2-adamantyl]-2-(4-chlorophenoxy)-2-methylpropanamide;

2-(4-chlorophenoxy)-2-methyl-N-[(E)-5-(2H-tetraazol-5-ylmethyl)-2-adamantyl]propanamide;

N-{(E)-5-[(aminosulfonyl)methyl]-2-adamantyl}-2-(4-chlorophenoxy)-2-methyl propanamide;

N-{(E)-5-[(Z)-amino(hydroxyimino)methyl]-2-adamantyl-2-(4-chlorophenoxy)-2-methyl propanamide;

(E)-N-[4-(aminosulfonyl)benzyl]-4-{[2-(4-chlorophenoxy)-2-methylpropanoyl]amino}adamantane-1-carboxamide;

(E)-4-{[2-(4-chlorophenoxy)-2-methylpropanoyl]amino}-N-(4{[(methylsulfonyl)amino]carbonyl}benzyl)adamantane-1-carboxamide;

(E)-4-({2-[(4-chlorophenyl)thio]-2-methylpropanoyl}amino)adamantane-1-carboxylic acid;

(E)-4-({2-[(4-methoxyphenyl)thio]-2-methylpropanoyl}amino)adamantane-1-carboxamide amide;

(E)-4-({2-[(4-methoxyphenyl)sulfinyl]-2-methylpropanoyl}amino)adamantane-1-carboxamide;

(E)-4-({2-[(4-methoxyphenyl)sulfonyl]-2-methylpropanoyl}amino)adamantane-1-carboxamide;

(E)-4-({2-[4-chloro-2-(pyrrolidin-1-ylsulfonyl)phenoxy]-2-methylpropanoyl}amino)adamantane-1-carboxamide;

(E)-4-({2-methyl-2-[4-(methylsulfonyl)phenoxy]propanoyl}amino)adamantane-1-carboxamide;

(E)-4-({2-methyl-2-[2-(methylsulfonyl)phenoxy]propanoyl}amino)adamantane-1-carboxamide;

(E)-4-[(2-{4-chloro-2-[(diethylamino)sulfonyl]phenoxyl}-2-methylpropanoyl)amino]adamantane-1-carboxamide;

(E)-4-({2-methyl-2-[4-(pyrrolidin-1-ylsulfonyl)phenoxy]propanoyl}amino)adamantane-1-carboxamide;

2-(2-chloro-4-fluorophenoxy)-N-[(E)-5-hydroxy-2-adamantyl]-2-methylpropanamide;

2-(2-chloro-4-fluorophenoxy)-2-methyl-N-[(E)-5-(2H-tetraazol-5-yl)-2-adamantyl]propanamide;

2-(2-chloro-4-fluorophenoxy)-2-methyl-N-[(E)-5-(methylthio)-2-adamantyl]propanamide;

2-(2-chloro-4-fluorophenoxy)-2-methyl-N-[(E)-5-(methylsulfonyl)-2-adamantyl]propanamide;

2-(2-chloro-4-fluorophenoxy)-2-methyl-N-[(E)-5-(methylsulfinyl)-2-adamantyl]propanamide;

N-[(E)-5-(aminosulfonyl)-2-adamantyl]-2-(4-chlorophenoxy)-2-methylpropanamide;
(E)-4-({[1-(4-chlorophenoxy)cyclobutyl]carbonyl}amino)adamantane-1-carboxamide;
4-[({[((E)-4-{[2-(4-chlorophenoxy)-2-methylpropanoyl]amino}-1-adamantyl)methyl]sulfonyl}amino)methyl]benzoic acid;
2-(4-chlorophenoxy)-N-[(E)-5-(1H-imidazol-2-yl)-2-adamantyl]-2-methylpropanamide;
(2E)-3-((E)-4-{[2-(4-Chlorophenoxy)-2-methylpropanoyl]amino}-1-adamantyl)acrylic acid;
(E)-4-[(2-methyl-2-{[5-(1H-pyrazol-1-yl)pyridin-2-yl]oxy}propanoyl)amino]adamantine-1-carboxamide;
2-(4-chlorophenoxy)-N-[(E)-5-isoxazol-5-yl-2-adamantyl]-2-methylpropanamide;
2-(4-chlorophenoxy)-2-methyl-N-{(E)-5-[(2-morpholin-4-ylethoxy)methyl]-2-adamantyl}propanamide;
N-[(E)-5-(aminosulfonyl)-2-adamantyl]-2-(2-chlorophenoxy)-2-methylpropanamide;
N-[(E)-5-(aminosulfonyl)-2-adamantyl]-2-methyl-2-(2-methylphenoxy)propanamide;
N-[(E)-5-(aminosulfonyl)-2-adamantyl]-2-methyl-2-(4-methylphenoxy)propanamide;
N-[(E)-5-(aminosulfonyl)-2-adamantyl]-2-methyl-2-[2-(trifluoromethyl)phenoxy]propanamide;
N-[(E)-5-(aminosulfonyl)-2-adamantyl]-2-methyl-2-[2-(trifluoromethoxy)phenoxy]propanamide;
N-[(E)-5-(aminosulfonyl)-2-adamantyl]-2-(2-chloro-4-fluorophenoxy)-2-methyl-propanamide;
(E)-4-{[2-(2-chlorophenoxy)-2-methyl-3-phenylpropanoyl]amino}adamantane-1-carboxamide;
2-(4-chlorophenoxy)-N-[(E)-5-hydroxy-2-adamantyl]-2-methylpropanamide;
(E)-4-({2-methyl-2-[(5-morpholin-4-ylpyridin-2-yl)oxy]propanoyl}amino)adamantane-1-carboxamide;
(E)-4-{[2-methyl-2-(pyridin-2-yloxy)propanoyl]amino}adamantane-1-carboxamide;
2-(4-chlorophenoxy)-2-methyl-N-{(E)-5-[(methylamino)sulfonyl]-2-adamantyl}propanamide;
3-((E)-4-{[2-(4-chlorophenoxy)-2-methylpropanoyl]amino}-1-adamantyl)propanoic acid;
2-(4-chlorophenoxy)-N-{(E)-5-[(dimethylamino)sulfonyl]-2-adamantyl}-2-methylpropanamide;
(E)-4-[(2-{[5-(1H-imidazol-1-yl)pyridin-2-yl]oxy}-2-methylpropanoyl)amino]adamantine-1-carboxamide;
2-(4-chlorophenoxy)-2-methyl-N-[(E)-5-(1H-pyrazol-3-yl)-2-adamantyl]propanamide;
N-[(E)-5-(aminosulfonyl)-2-adamantyl]-2-(3-chlorophenoxy)-2-methylpropanamide;
N-[(E)-5-(aminosulfonyl)-2-adamantyl]-2-methyl-2-(3-methylphenoxy)propanamide;
N-[(E)-5-(aminosulfonyl)-2-adamantyl]-2-(2-methoxyphenoxy)-2-methylpropanamide;
N-[(E)-5-(aminosulfonyl)-2-adamantyl]-2-(3-methoxyphenoxy)-2-methylpropanamide;
N-[(E)-5-(aminosulfonyl)-2-adamantyl]-2-(4-methoxyphenoxy)-2-methylpropanamide;
N-[(E)-5-(aminosulfonyl)-2-adamantyl]-2-(4-cyanophenoxy)-2-methylpropanamide;
(E)-4-{[2-methyl-2-(2-methylphenoxy)propanoyl]amino}adamantane-1-carboxamide;
(E)-4-{[2-methyl-2-(3-methylphenoxy)propanoyl]amino}adamantane-1-carboxamide;
(E)-4-[(2-methyl-2-{[(1S,2S)-2-methylcyclohexyl]oxy}propanoyl)amino]adamantane-1-carboxylic acid;
(E)-4-({2-methyl-2-[(2-methylcyclohexyl)oxy]propanoyl}amino)adamantane-1-carboxamide
(E)-4-{[2-(cycloheptyloxy)-2-methylpropanoyl]amino}adamantane-1-carboxamide;
(E)-4-{[2-(cyclohexylmethoxy)-2-methylpropanoyl]amino}adamantane-1-carboxamide;
(E)-4-({2-methyl-2-[(3-methylcyclohexyl)oxy]propanoyl}amino)adamantane-1-carboxamide;
(E)-4-{[2-(2-chlorophenoxy)-2-methylpropanoyl]amino}adamantane-1-carboxamide;
4-{[({(E)-4-[(2-methyl-2-phenoxypropanoyl)amino]-1-adamantyl}carbonyl)amino]methyl}benzoic acid;
(E)-4-({2-[(4,4-dimethylcyclohexyl)oxy]-2-methylpropanoyl}amino)adamantane-1-carboxylic acid;
(E)-4-{[2-methyl-2-(1,2,3,4-tetrahydronaphthalen-2-yloxy)propanoyl]amino}adamantane-1-carboxylic acid;
(E)-4-{[2-(4-bromophenoxy)-2-methylpropanoyl]amino}adamantane-1-carboxylic acid;
(E)-4-{[2-methyl-2-(1-naphthyloxy)propanoyl]amino}adamantane-1-carboxylic acid;
(E)-4-{[2-(2,3-dichlorophenoxy)-2-methylpropanoyl]amino}adamantane-1-carboxylic acid;
(E)-4-{[2-(2,4-dichlorophenoxy)-2-methylpropanoyl]amino}adamantane-1-carboxylic acid;
(E)-4-{[2-(2,5-dichlorophenoxy)-2-methylpropanoyl]amino}adamantane-1-carboxylic acid;
(E)-4-{[2-(2,4-dimethylphenoxy)-2-methylpropanoyl]amino}adamantane-1-carboxylic acid;
(E)-4-{[2-(2,5-dimethylphenoxy)-2-methylpropanoyl]amino}adamantane-1-carboxylic acid;
(E)-4-{[2-methyl-2-(2-naphthyloxy)propanoyl]amino}adamantane-1-carboxylic acid;
(E)-4-{[2-(4-bromo-2-fluorophenoxy)-2-methylpropanoyl]amino}adamantane-1-carboxylic acid;
(E)-4-({2-methyl-2-[(7-methyl-2,3-dihydro-1H-inden-4-yl)oxy]propanoyl}amino)adamantane-1-carboxylic acid;
(E)-4-{[2-(4-bromo-2-chlorophenoxy)-2-methylpropanoyl]amino}adamantane-1-carboxylic acid;
(E)-4-{[2-(1,1'-biphenyl-3-yloxy)-2-methylpropanoyl]amino}adamantane-1-carboxylic acid;
(E)-4-{[2-(2-bromophenoxy)-2-methylpropanoyl]amino}adamantane-1-carboxylic acid;
(E)-N-[4-(aminocarbonyl)benzyl]-4-[(2-methyl-2-phenoxypropanoyl)amino]adamantane-1-carboxamide;
(E)-4-{[2-(4-chlorophenoxy)-2-methylpropanoyl]amino}-N-(1,3-thiazol-5-ylmethyl)adamantane-1-carboxamide;
(E)-4-{[2-(4-chlorophenoxy)-2-methylpropanoyl]amino}-N-(pyridin-4-ylmethyl)adamantine-1-carboxamide;
(E)-4-{[2-(4-aminophenoxy)-2-methylpropanoyl]amino}adamantane-1-carboxamide;
(E)-4-({2-methyl-2-[2-(trifluoromethoxy)phenoxy]propanoyl}amino)adamantane-1-carboxamide;
(E)-4-({2-methyl-2-[2-(trifluoromethyl)phenoxy]propanoyl}amino)adamantane-1-carboxamide;
(E)-4-({2-methyl-2-[4-(pyrrolidin-1-ylsulfonyl)phenoxy]propanoyl}amino)adamantane-1-carboxamide;
2-(2-chloro-4-fluorophenoxy)-N-[(E)-5-hydroxy-2-adamantyl]-2-methylpropanamide;
2-(2-chloro-4-fluorophenoxy)-N-[(E)-5-cyano-2-adamantyl]-2-methylpropanamide;
(E)-4-[(2-methyl-2-{4-[(trifluoroacetyl)amino]phenoxy}propanoyl)amino]adamantane-1-carboxamide;
(E)-4-{[2-(3-bromo-4-methoxyphenoxy)-2-methylpropanoyl]amino}adamantane-1-carboxamide;
(E)-4-{[2-(2,5-dibromo-4-methoxyphenoxy)-2-methylpropanoyl]amino}adamantane-1-carboxamide;
(E)-4-{[2-(2-bromo-4-methoxyphenoxy)-2-methylpropanoyl]amino}adamantane-1-carboxamide;

(E)-4-{[2-(2-chloro-4-fluorophenoxy)-2-methylpropanoyl] amino}-N,N-dimethyladamantane-1-carboxamide;
2-(4-chlorophenoxy)-N-((E)-5-{[(4-methoxy-6-methylpyrimidin-2-yl)amino]methyl}-2-adamantyl)-2-methylpropanamide;
(E)-4-{[2-(4-{[(tert-butylamino)carbonyl]amino}phenoxy)-2-methylpropanoyl]amino}adamantane-1-carboxamide;
ethyl 4-(2-{[(E)-5-(aminocarbonyl)-2-adamantyl]amino}-1,1-dimethyl-2-oxoethoxy)phenylcarbamate;
(E)-4-[(2-methyl-2-{4-[(propylsulfonyl)amino] phenoxy}propanoyl)amino]adamantane-1-carboxamide;
(E)-4-[(2-{4-[(3,3-dimethylbutanoyl)amino]phenoxy}-2-methylpropanoyl)amino]adamantane-1-carboxamide;
(E)-4-{[2-methyl-2-(phenylsulfinyl)propanoyl] amino}adamantane-1-carboxylic acid;
(E)-4-{[2-methyl-2-(phenylsulfonyl)propanoyl] amino}adamantane-1-carboxylic acid;
N-[(E)-5-cyano-2-adamantyl]-2-[(4-methoxyphenyl)sulfonyl]-2-methylpropanamide;
2-[(4-methoxyphenyesulfonyl]-2-methyl-N-[(E)-5-(2H-tetraazol-5-yl)-2-adamantyl]propanamide; and
(E)-4-({2-[4-(benzyloxy)phenoxy]-2-methylpropanoyl}amino)adamantane-1-carboxamide.

Also included in the present application are selective 11β-HSD1 inhibitors selected from a group of compounds having formula (III),

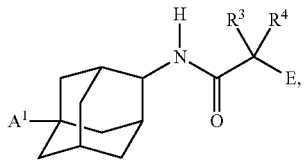

wherein $A^1$, is selected from the group consisting of alkyl-NH-alkyl, alkylcarbonyl, alkylsulfonyl, cycloalkyl, cycloalkylcarbonyl, cycloalkylsulfonyl, arylcarbonyl, arylsulfonyl, heteroaryl, heteroarylalkyl, heteroaryloxyalkyl, heterocyclecarbonyl, heterocyclesulfonyl, aryl, arylalkyl, aryloxyalkyl, carboxyalkyl, carboxycycloalkyl, haloalkyl, heterocyclealkyl, heterocycleoxyalkyl, —S(O)$_2$—N(R$^5$R$^6$), —NR$^7$—[C(R$^8$R$^9$)]$_n$—C(O)—R$^{10}$, —O—[C(R$^{11}$R$^{12}$)]$_p$—C(O)—R$^{13}$, —OR$^{14a}$, —N(R$^{15}$R$^{16}$), —CO$_2$R$^{17}$, —C(O)—N(R$^{18}$R$^{19}$), —C(R$^{20}$R$^{21}$)—OR$^{22}$, —C(R$^{23}$R$^{24}$)—N(R$^{25}$R$^{26}$), and heterocycle, with the exception that 5 membered heterocycles may not contain two oxygen atoms, n is 0 or 1;
p is 0 or 1;

E is selected from the group consisting of a cycloalkyl, alkyl, aryl, heteroaryl and heterocycle, wherein the heteroaryl and the heterocycle are appended to the parent molecular moiety through an available carbon atom, or $R^4$ and E together with the atoms to which they are attached form a ring selected from the group consisting of cycloalkyl and heterocycle;

$R^3$ and $R^4$ are each independently selected from the group consisting of hydrogen, alkyl, carboxyalkyl, carboxycycloalkyl, cycloalkyl, haloalkyl, aryl, arylalkyl, heteroaryl, heteroarylalkyl, heterocycle and heterocyclealkyl, or $R^3$ and $R^4$ together with the atom to which they are attached form a ring selected from the group consisting of cycloalkyl and heterocycle; $R^5$ and $R^6$ are each independently selected from the group consisting of hydrogen, alkoxy, alkyl, alkylcarbonyl, alkylsufonyl, carboxy, carboxyalkyl, carboxycycloalkyl, cycloalkyl, cycloalkyloxy, cycloalkylsulfonyl, aryl, arylalkyl, arylalkylcarbonyl, arylcarbonyl, aryloxy, aryloxyalkyl, arylsulfonyl, heteroaryl, heteroarylalkyl, heteroarylalkylcarbonyl, heteroarylcarbonyl, heteroaryloxyalkyl, heteroarylsulfonyl, heterocycle, heterocyclealkyl, heterocyclealkylcarbonyl, heterocyclecarbonyl, heterocycleoxyalkyl, heterocycleoxy, heterocyclesulfonyl and hydroxy, or $R^5$ and $R^6$ together with the atom to which they are attached form a heterocycle;

$R^7$ is selected from the group consisting of hydrogen, alkyl, carboxyalkyl, cycloalkyl, carboxycycloalkyl, aryl, arylalkyl, aryloxyalkyl, hydroxy, alkoxy, heteroaryl, heteroarylalkyl, heteroaryloxyalkyl, heterocycle, heterocyclealkyl and heterocycleoxyalkyl;

$R^8$ and $R^9$ are each independently selected from the group consisting of hydrogen and alkyl, or $R^8$ and $R^9$ taken together with the atom to which they are attached form a ring selected from the group consisting of cycloalkyl and heterocycle;

$R^{10}$ is selected from the group consisting of hydrogen, alkyl, carboxyalkyl, cycloalkyl, carboxycycloalkyl, aryl, arylalkyl, aryloxy, aryloxyalkyl, hydroxy, alkoxy, cycloalkyloxy, heteroaryl, heteroarylalkyl, heteroaryloxy, heteroaryloxyalkyl, heterocycle, heterocyclealkyl, heterocycleoxy, heterocycleoxyalkyl and —N(R$^{32}$R$^{33}$);

$R^{11}$ and $R^{12}$ are each independently selected from the group consisting of hydrogen and alkyl or $R^{11}$ and $R^{12}$ taken together with the atom to which they are attached form a ring selected from the group consisting of cycloalkyl and heterocycle;

$R^{13}$ is selected from the group consisting of hydroxy and —N(R$^{34}$R$^{35}$);

$R^{14a}$ is selected from the group consisting of carboxyalkyl, cycloalkyl, carboxycycloalkyl, aryl, arylalkyl, aryloxyalkyl, haloalkyl, heteroaryl, heteroarylalkyl, heteroaryloxyalkyl, heterocycle, heterocyclealkyl and heterocycleoxyalkyl;

$R^{14b}$ is selected from the group consisting of hydrogen, alkyl, carboxyalkyl, cycloalkyl, carboxycycloalkyl, aryl, arylalkyl, aryloxyalkyl, haloalkyl, heteroaryl, heteroarylalkyl, heteroaryloxyalkyl, heterocycle, heterocyclealkyl and heterocycleoxyalkyl;

$R^{15}$ and $R^{16}$ are each independently selected from the group consisting of hydrogen, alkyl, alkylcarbonyl, carboxyalkyl, cycloalkyl, carboxycycloalkyl, aryl, arylalkyl, arylalkylcarbonyl, arylcarbonyl, aryloxyalkyl, heteroaryl, heteroarylalkyl, heteroarylalkylcarbonyl, heteroarylcarbonyl, heteroaryloxyalkyl, heteroarylsulfonyl, heterocycle, heterocyclealkyl, heterocyclealkylcarbonyl, heterocyclecarbonyl, heterocycleoxyalkyl, heterocyclesulfonyl, alkylsufonyl, cycloalkylsulfonyl and arylsulfonyl, or $R^{15}$ and $R^{16}$ together with the atom to which they are attached form a heterocycle;

$R^{17}$ is selected from the group consisting of hydrogen, alkyl, carboxyalkyl, cycloalkyl, carboxycycloalkyl, aryl, arylalkyl, aryloxyalkyl, heteroaryl, heteroarylalkyl, heteroaryloxyalkyl, heterocycle, heterocyclealkyl and heterocycleoxyalkyl;

$R^{18}$ and $R^{19}$ are each independently selected from the group consisting of hydrogen, alkoxy, alkyl, alkylsufonyl, carboxy, carboxyalkyl, carboxycycloalkyl, cycloalkyl, cycloalkyloxy, cycloalkylsulfonyl, aryl, arylalkyl, aryloxy, aryloxyalkyl, arylsulfonyl, heteroaryl, heteroarylalkyl, heteroaryloxyalkyl, heteroarylsulfonyl, heterocycle, heterocyclealkyl, heterocycleoxyalkyl, heterocycleoxy, heterocyclesulfonyl and hydroxy, or $R^{18}$ and $R^{19}$ together with the atom to which they are attached form a heterocycle;

$R^{20}$, $R^{21}$ and $R^{22}$ are each independently selected from the group consisting of hydrogen, alkyl, aryl, arylalkyl, carboxyalkyl, carboxycycloalkyl, cycloalkyl, haloalkyl, heteroaryl, heteroarylalkyl, heterocycle and heterocyclealkyl;

$R^{23}$ and $R^{24}$ are each independently selected from the group consisting of hydrogen, alkyl, alkylcarbonyl, alkylsulfonyl, aryl, arylcarbonyl, arylsulfonyl, carboxyalkyl, carboxycycloalkyl, cycloalkyl, cycloalkylcarbonyl, cycloalkylsulfonyl, heteroaryl, heteroarylcarbonyl, heteroarylsulfonyl, heterocycle, heterocyclecarbonyl and heterocyclesulfonyl;

$R^{25}$ and $R^{26}$ are each independently selected from the group consisting of hydrogen, alkoxy, alkyl, alkylcarbonyl, alkylsulfonyl, aryl, arylcarbonyl, aryloxy, arylsulfonyl, carboxyalkyl, carboxycycloalkyl, cycloalkyl, cycloalkylcarbonyl, cycloalkyloxy, cycloalkylsulfonyl, heteroaryl, heteroarylcarbonyl, heteroaryloxy, heteroarylsulfonyl, heterocycle, heterocyclecarbonyl, heterocycleoxy, heterocyclesulfonyl and hydroxy, or $R^{25}$ and $R^{26}$ together with the nitrogen to which they are attached form a ring selected from the group consisting of heteroaryl and heterocycle; $R^{32}$ and $R^{33}$ are each independently selected from the group consisting of hydrogen, alkyl, carboxy, carboxyalkyl, cycloalkyl, cycloalkyloxy, carboxycycloalkyl, aryl, arylalkyl, aryloxy, aryloxyalkyl, heterocycle, heterocyclealkyl, heterocycleoxyalkyl, heterocycleoxy, hydroxy, alkoxy, alkylsufonyl, cycloalkylsulfonyl, arylsulfonyl, and heterocyclesulfonyl, or $R^{32}$ and $R^{33}$ together with the atom to which they are attached form a heterocycle;

$R^{34}$ and $R^{35}$ are each independently selected from the group consisting of hydrogen, alkyl, carboxy, carboxyalkyl, cycloalkyl, cycloalkyloxy, carboxycycloalkyl, awl, arylalkyl, aryloxy, aryloxyalkyl, heterocycle, heterocyclealkyl, heterocycleoxyalkyl, heterocycleoxy, hydroxy, alkoxy, alkylsufonyl, cycloalkylsulfonyl, arylsulfonyl, and heterocyclesulfonyl, or $R^{34}$ and $R^{35}$ together with the atom to which they are attached form a heterocycle; and $R^{36}$ and $R^{37}$ are each independently selected from the group consisting of hydrogen, alkyl and aryl;

or a pharmaceutically acceptable metabolite, salt, prodrug, salt of a prodrug, or a combination thereof.

Examples of compounds of formula (III) that are useful for the methods disclosed in the present application are (E)-4-{[1-(4-chloro-phenyl)-cyclobutanecarbonyl]-amino}-adamantane-1-carboxylic acid;
(E)-4-[(1-phenyl-cyclopropanecarbonyl)-amino]-adamantane-1-carboxylic acid;
(E)-4-(2-methyl-2-phenyl-propionylamino)-adamantane-1-carboxylic acid;
(E)-4-{[1-(4-chloro-phenyl)-cyclobutanecarbonyl]-amino}-adamantane-1-carboxylic acid amide;
(E)-4-[(1-phenyl-cyclopropanecarbonyl)-amino]-adamantane-1-carboxylic acid amide;
(E)-4-(2-methyl-2-phenyl-propionylamino)-adamantane-1-carboxylic acid amide;
(E)-4-({[1-(4-chlorophenyecyclohexyl]carbonyl}amino)adamantane-1-carboxamide;
(E)-4-({[1-(4-chlorophenyl)cyclopropyl]carbonyl}amino)adamantane-1-carboxamide;
(E)-4-({[1-(4-chlorophenyl)cyclopentyl]carbonyl}amino)adamantane-1-carboxamide;
(E)-4-{[2-(4-chlorophenyl)-2-methylpropanoyl]amino}adamantane-1-carboxamide;
(E)-4-{[(1-phenylcyclopentyl)carbonyl]amino}adamantane-1-carboxamide;
(E)-4-({[1-(3-fluorophenyl)cyclopentyl]carbonyl}amino)adamantane-1-carboxamide;
(E)-4-({[1-(2-chloro-4-fluorophenyl)cyclopentyl]carbonyl}amino)adamantane-1-carboxamide;
(E)-4-({[1-(4-fluorophenyl)cyclopentyl]carbonyl}amino)adamantane-1-carboxamide;
(E)-4-({[1-(2-fluorophenyl)cyclopentyl]carbonyl}amino)adamantane-1-carboxamide;
(E)-4-{[(1-methylcyclohexyl)carbonyl]amino}adamantane-1-carboxamide;
(E)-4-({[1-(2,4-dichlorophenyl)cyclopropyl]carbonyl}amino)adamantane-1-carboxamide;
(E)-4-({[1-(4-methoxyphenyl)cyclopropyl]carbonyl}amino)adamantane-1-carboxamide;
(E)-4-({[1-(4-methylphenyl)cyclopropyl]carbonyl}amino)adamantane-1-carboxamide;
(E)-4-{[2-methyl-2-(4-pyridin-4-ylphenyl)propanoyl]amino}adamantane-1-carboxamide;
(E)-4-[(2-methyl-2-thien-2-ylpropanoyl)amino]adamantane-1-carboxamide;
(E)-4-[(2-methyl-2-thien-3-ylpropanoyl)amino]adamantane-1-carboxamide;
(E)-4-({2-methyl-2-[5-(trifluoromethyl)pyridin-2-yl]propanoyl}amino)adamantane-1-carboxamide;
(E)-4-[(2-methyl-2-{4-[5-(trifluoromethyl)pyridin-2-yl]phenyl}propanoyl)amino]adamantane-1-carboxamide;
(E)-4-({[1-(4-methoxyphenyl)cyclopentyl]carbonyl}amino)adamantane-1-carboxamide;
(E)-4-{[2-(4-bromophenyl)-2-methylpropanoyl]amino}adamantane-1-carboxamide;
(E)-4-[5-(aminocarbonyl)-2-adamantyl]-3-methyl-1-(2-methylbenzyl)-2-oxopiperidine-3-carboxamide;
(E)-4-(aminocarbonyl)-2-adamantyl]-1-benzyl-3-methyl-2-oxopyrrolidine-3-carboxamide;
(E)-4-(aminocarbonyl)-2-adamantyl]-3-methyl-1-(2-methylbenzyl)-2-oxopyrrolidine-3-carboxamide;
(E)-4-(aminocarbonyl)-2-adamantyl]-1-(2-chlorobenzyl)-3-methyl-2-oxopyrrolidine-3-carboxamide;
(E)-4-(aminocarbonyl)-2-adamantyl]-1-(3-chlorobenzyl)-3-methyl-2-oxopyrrolidine-3-carboxamide;
(E)-4-({2-methyl-2-[4-(1-methyl-1H-pyrazol-4-yl)phenyl]propanoyl}amino)adamantane-1-carboxamide;
(E)-4-{[2-(3-bromophenyl)-2-methylpropanoyl]amino}adamantane-1-carboxamide;
(E)-4-({2-[4-(3,5-dimethylisoxazol-4-yl)phenyl]-2-methylpropanoyl}amino)adamantane-1-carboxamide;
(E)-4-{[2-methyl-2-(4-pyridin-3-ylphenyl)propanoyl]amino}adamantane-1-carboxamide;
4-{[({(E)-4-[(2-methyl-2-thien-2-ylpropanoyl)amino]-1-adamantyl}carbonyl)amino]methyl}benzoic acid;
(E)-4-({2-methyl-2-[4-(1H-pyrazol-4-yl)phenyl]propanoyl}amino)adamantane-1-carboxamide;
(E)-4-(aminocarbonyl)-2-adamantyl]-3-methyl-1-(1-methyl-1-phenylethyl)-2-oxopyrrolidine-3-carboxamide;
(E)-4-(aminocarbonyl)-2-adamantyl]-3-methyl-2-oxo-1-[(1R)-1-phenylethyl]pyrrolidine-3-carboxamide;
(E)-4-(aminocarbonyl)-2-adamantyl]-3-methyl-2-oxo-1-[(1S)-1-phenylethyl]pyrrolidine-3-carboxamide;
(E)-4-{[2-methyl-2-(1,3-thiazol-2-yl)propanoyl]amino}adamantane-1-carboxamide;
(E)-4-(aminocarbonyl)-2-adamantyl]-1-(4-chlorobenzyl)-3-methylpiperidine-3-carboxamide;
(E)-4-{[2-(4-hydroxyphenyl)-2-methylpropanoyl]amino}adamantane-1-carboxamide;
(E)-4-(aminocarbonyl)-2-adamantyl]-1-benzyl-3-methyl-2-oxopiperidine-3-carboxamide;
(E)-4-{[2-methyl-2-(4-phenoxyphenyl)propanoyl]amino}adamantane-1-carboxamide;

(E)-4-{[2-(1-benzothien-3-yl)-2-methylpropanoyl]amino}adamantane-1-carboxamide;

(E)-4-{[2-(5-fluoropyridin-2-yl)-2-methylpropanoyl]amino}adamantane-1-carboxamide; and (E)-4-[(2-methyl-2-quinoxalin-2-ylpropanoyl)amino]adamantane-1-carboxamide.

The present application also comprises selective 11β-HSD1 inhibitors selected from a group of compounds having formula (IV),

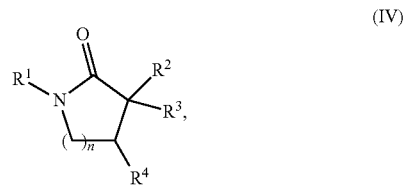

wherein n is 1 or 2;

$R^1$ is cycloalkyl or heterocycle, each of which is independently unsubstituted or substituted with 1, 2, 3 or 4 substituents independently selected from the group consisting of alkyl, alkenyl, haloalkyl, Cl, Br, F, I, —CN, —NO$_2$, —OR$_b$, —SR$_b$, —S(O)R$_7$, —S(O)$_2$R$_7$, —NR$_a$R$_b$, —C(O)R$_b$, —C(O)OR$_b$, —C(O)NR$_a$R$_b$, —S(O)$_2$NR$_a$R$_b$, —C(=NOH)NH$_2$, —C(=NH)NH$_2$, R$_c$, —(CR$_d$R$_e$)$_m$—CN, —(CR$_d$R$_e$)$_m$—OR$_b$, —(CR$_d$R$_e$)$_m$—SR$_b$, —(CR$_d$R$_e$)$_m$—S(O)$_2$R$_Z$, —(CR$_d$R$_e$)$_m$—NR$_a$R$_b$, —(CR$_d$R$_e$)$_m$—C(O)R$_b$, —(CR$_d$R$_e$)$_m$—C(O)OR$_b$, —(CR$_d$R$_e$)$_m$—S(O)$_2$NR$_a$R$_b$, —(CR$_d$R$_e$)$_m$—R$_c$, —N(R$_a$)—(CR$_d$R$_e$)$_m$—C(O)R$_b$, —N(R$_a$)—(CR$_d$R$_e$)$_m$—C(O)OR$_b$, —N(R$_a$)—(CR$_d$R$_e$)$_m$—C(O)NR$_a$R$_b$, —O—(CR$_d$R$_e$)$_m$—C(O)R$_b$, —O—(CR$_d$R$_e$)$_m$—C(O)OR$_b$, and —O—(CR$_d$R$_e$)$_m$—C(O)NR$_a$R$_b$;

$R^2$ and $R^3$, at each occurrence, are each independently hydrogen, alkyl, R$_c$ or —(CR$_d$R$_e$)$_m$—R$_c$ or $R^2$ and $R^3$ taken together with the atoms to which they are attached form a cycloalkyl;

$R^4$ is -E-G or —(CR$_d$R$_e$)$_m$-E-G, wherein E, at each occurrence, is independently O, S, S(O), S(O)$_2$, N(R$_e$), or a bond and G, at each occurrence, is independently alkyl, haloalkyl, —(CR$_d$R$_e$)$_m$—OR$_d$, —(CR$_d$R$_e$)$_m$—C(O)OR$_d$, —R$_A$, or —(CR$_d$R$_e$)$_m$—R$_A$, wherein R$_A$, at each occurrence, is independently selected from the group consisting of aryl, heteroaryl, cycloalkyl and heterocycle, and each R$_A$ is independently unsubstituted or substituted with 1, 2, 3 or 4 substituents independently selected from the group consisting of alkyl, alkenyl, haloalkyl, Cl, Br, F, I, —CN, —NO$_2$, —OR$_d$, —S(R$_d$), —S(O)(alkyl), —S(O)(haloalkyl), —S(O)$_2$(alkyl), —S(O)$_2$(haloalkyl), —NR$_d$R$_e$, —C(O)(R$_d$), —C(O)OR$_d$, —C(O)NR$_d$R$_e$, —S(O)$_2$NR$_d$R$_e$, R$_c$, —(CR$_d$R$_e$)$_m$—CN, —(CR$_d$R$_e$)$_m$—NO$_2$, —(CR$_d$R$_e$)$_m$—OR$_d$, —(CR$_d$R$_e$)$_m$—S(R$_d$), —(CR$_d$R$_e$)$_m$—S(O)(alkyl), —(CR$_d$R$_e$)$_m$—S(O)(haloalkyl), —(CR$_d$R$_e$)$_m$—S(O)$_2$(alkyl), —(CR$_d$R$_e$)$_m$—S(O)$_2$(haloalkyl), —(CR$_d$R$_e$)$_m$—NR$_d$R$_e$, —(CR$_d$R$_e$)$_m$—C(O)(R$_d$), —(CR$_d$R$_e$)$_m$—C(O)OR$_d$, —(CR$_d$R$_e$)$_m$—C(O)NR$_d$R$_e$, —(CR$_d$R$_e$)$_m$—S(O)$_2$NR$_d$R$_e$, and —(CR$_d$R$_e$)$_m$—R$_c$;

R$_a$, at each occurrence, is independently hydrogen or alkyl;

R$_b$, at each occurrence, is independently hydrogen, alkyl, haloalkyl, R$_c$ or —(CR$_d$R$_e$)$_m$—R$_e$;

R$_Z$, at each occurrence, is independently alkyl, haloalkyl, R$_c$ or —(CR$_d$R$_e$)$_m$—R$_e$;

R$_e$, at each occurrence, is independently aryl, heteroaryl, cycloalkyl or heterocycle; wherein each R$_e$ is independently unsubstituted or substituted with 1, 2, 3 or 4 substituents independently selected from the group consisting of alkyl, alkenyl, haloalkyl, Cl, Br, F, I, —CN, —NO$_2$, —OR$_d$, —S(R$_d$), —S(O)(alkyl), —S(O)(haloalkyl), —S(O)$_2$(alkyl), —S(O)$_2$(haloalkyl), —NR$_d$R$_e$, —C(O)(R$_d$), —C(O)OR$_d$, —C(O)NR$_d$R$_e$, —S(O)$_2$NR$_d$R$_e$, —(CR$_d$R$_e$)$_m$—CN, —(CR$_d$R$_e$)$_m$—NO$_2$, —(CR$_d$R$_e$)$_m$—OR$_d$, —(CR$_d$R$_e$)$_m$—S(R$_d$), —(CR$_d$R$_e$)$_m$—S(O)(alkyl), —(CR$_d$R$_e$)$_m$—S(O)(haloalkyl), —(CR$_d$R$_e$)$_m$—S(O)$_2$(alkyl), —(CR$_d$R$_e$)$_m$—S(O)$_2$(haloalkyl), —(CR$_d$R$_e$)$_m$—NR$_d$R$_e$, —(CR$_d$R$_e$)$_m$—C(O)(R$_d$), —(CR$_d$R$_e$)$_m$—C(O)OR$_d$, —(CR$_d$R$_e$)$_m$—C(O)NR$_d$R$_e$, and —(CR$_d$R$_e$)$_m$—S(O)$_2$NR$_d$R$_e$;

R$_d$ and R$_e$, at each occurrence, are independently hydrogen, alkyl or haloalkyl; and m is 0, 1, 2, 3, 4, 5 or 6;

or a pharmaceutically acceptable metabolite, salt, prodrug, salt of a prodrug, or a combination thereof.

Examples of compounds of formula (IV) that are comprised in the present invention are 6-[(1-cycloheptyl-4,4-dimethyl-5-oxopyrrolidin-3-yl)methoxy]nicotinonitrile;

4-(4-{[(5-cyanopyridin-2-yl)oxy]methyl}-3,3-dimethyl-2-oxopyrrolidin-1-yl)azepane-1-carboxamide;

1-cycloheptyl-3,3-dimethyl-4-(phenoxymethyl)pyrrolidin-2-one;

1-cycloheptyl-4-{[(2-fluorophenyl)(methyl)amino]methyl}-3,3-dimethylpyrrolidin-2-one;

6-{[1-(5-hydroxycyclooctyl)-4,4-dimethyl-5-oxopyrrolidin-3-yl]methoxy}nicotinonitrile;

(E)-4-(4-{[(5-cyanopyridin-2-yl)oxy]methyl}-3,3-dimethyl-2-oxopyrrolidin-1-yl)adamantine-1-carboxamide;

9-(4-{[(5-cyanopyridin-2-yl)oxy]methyl}-3,3-dimethyl-2-oxopyrrolidin-1-yl)bicycle[3.3.1]nonane-3-carboxamide;

trans ethyl(1R,7S)-4-(4-{[(5-cyanopyridin-2-yl)oxy]methyl}-3,3-dimethyl-2-oxopyrrolidin-1-yl)bicyclo[5.1.0]octane-8-carboxylate trans ethyl(1S,7R)-4-(4-{[(5-cyanopyridin-2-yl)oxy]methyl}-3,3-dimethyl-2-oxopyrrolidin-1-yl)bicyclo[5.1.0]octane-8-carboxylate;

6-{[4,4-dimethyl-1-(4-methylbicyclo[2.2.2]oct-1-yl)-5-oxopyrrolidin-3-yl]methoxy}nicotinonitrile;

6-{[1-(5-cyanocyclooctyl)-4,4-dimethyl-5-oxopyrrolidin-3-yl]methoxy}nicotinonitrile;

(E)-4-(4-{[(5-cyanopyridin-2-yl)oxy]methyl}-3,3-dimethyl-2-oxopyrrolidin-1-yl)adamantane-1-carbonitrile;

(E)-4-(3,3-dimethyl-2-oxo-4-{[4-(1H-1,2,4-triazol-1-yl)phenoxy]methyl}pyrrolidin-1-yl)adamantane-1-carboxamide;

(E)-4-(4-{[4-(1H-imidazol-1-yl)phenoxy]methyl}-3,3-dimethyl-2-oxopyrrolidin-1-yl)adamantane-1-carboxamide;

(E)-4-[3,3-dimethyl-2-oxo-4-({[5-(trifluoromethyl)pyridin-2-yl]oxy}methyl)pyrrolidin-1-yl]-N'-hydroxyadamantane-1-carboximidamide;

(E)-4-[3,3-dimethyl-2-oxo-4-({[5-(trifluoromethyl)pyridin-2-yl]oxy}methyl)pyrrolidin-1-yl]adamantane-1-carboxamide; and (E)-4-[3,3-dimethyl-2-oxo-4-({[5-(trifluoromethyl)pyridin-2-yl]oxy}methyl)pyrrolidin-1-yl]adamantane-1-carboximidamide.

Compounds including geometric isomers of carbon-carbon double bonds and carbon-nitrogen double are included in the present invention. Substituents around a carbon-carbon or a carbon-nitrogen double bond are designated as being of Z or E configuration and substituents around a cycloalkyl or heterocycloalkyl are designated as being of cis or trans configuration. Furthermore, substituents around an adamantane ring system are designated as being of Z or E relative configuration. For examples, see C. D. Jones, M. Kaselj, R. N. Salvatore, W. J. le Noble *J. Org. Chem.* Vol. 63 pages 2758-2760, 1998. All geometric isomeric forms and mixtures thereof of the compounds described herein are encompassed within the scope of the present invention.

Asymmetric centers exist in the present compounds. Individual stereoisomers of the compounds are prepared by synthesis from chiral starting materials or by preparation of racemic mixtures and separation by conversion to a mixture of diastereomers followed by separation or recrystallization, chromatographic techniques, or direct separation of the enantiomers on chiral chromatographic columns. Starting materials of particular stereochemistry are either commercially available or are made by the methods described herein and resolved by techniques well known in the art.

Compounds of this invention include at least one chiral center and can exist as single stereoisomers (e.g. single enantiomer), mixtures of stereoisomers (e.g. any mixture of enantiomers or diastereomers) or racemic mixtures thereof. As a result, all stereoisomers of the compounds of the invention are included in the present invention, including racemic mixtures, mixtures of diastereomers, mixtures of enantiomers, as well as individual optical isomers, including, enantiomers and single diastereomers of the compounds of the invention substantially free from their enantiomers or other diastereomers. By "substantially free" is meant greater than about 80% free of other enantiomers or diastereomers of the compound, more preferably greater than about 90% free of other enantiomers or diastereomers of the compound, even more preferably greater than about 95% free of other enantiomers or diastereomers of the compound, even more highly preferably greater than about 98% free of other enantiomers or diastereomers of the compound and most preferably greater than about 99% free of other enantiomers or diastereomers of the compound. Where the stereochemistry of the chiral centers present in the chemical structures illustrated herein is not specified, the chemical structure is intended to encompass compounds including either stereoisomer of each chiral center present in the compound.

Disorders that can be treated or prevented in a patient by administering to the patient, a therapeutically effective amount of the compound of the present invention in such an amount and for such time as is necessary to achieve the desired result.

The total daily dose of the compounds of the present invention necessary to inhibit the action of 11-beta-hydroxysteroid dehydrogenase Type 1 enzyme in single or divided doses can be in amounts, for example, from about 0.01 to 50 mg/kg body weight. In a more preferred range, compounds of the present invention inhibit the action of 11-beta-hydroxysteroid dehydrogenase Type 1 enzyme in a single or divided doses from about 0.05 to 25 mg/kg body weight. Single dose compositions can contain such amounts or submultiple doses thereof of the compounds of the present invention to make up the daily dose. In general, treatment regimens include administration to a patient in need of such treatment from about 1 mg to about 1000 mg of the compounds per day in single or multiple doses.

The present invention will be further clarified by the following examples, which are only intended to illustrate the present invention and are not intended to limit the scope of the present invention.

Example 1

Selective 11β-HSD1 Inhibitors Enhance Memory Consolidation in Mice After 2-Week Food-in-Diet Dosing Episodic memory is a type of long-term memory that requires one exposure for memory formation to occur. Patients with Alzheimer's disease suffer from episodic memory dysfunction, among other cognitive deficits. In addition, studies indicate that patients with a genetic risk for Alzheimer's disease have early deficits in episodic memory and executive function (Ringman, J. Geriatr. Psychiatry Neurology, 2005, 18:228-233).

The 24-hour inhibitory avoidance task in mice is a measure of one-trial learning and memory consolidation in response to a discrete aversive event (foot-shock). Mice are first placed in an illuminated compartment of a two-compartment apparatus. Mice will naturally step through into an adjoining dark compartment, which they prefer. When the mice enter the dark they receive a mild foot-shock. To assess memory, mice are tested 24 hours later and the length of time the animal refrains from entering the dark compartment is recorded (higher latencies indicate improved memory for the aversive event).

Male CD-1 mice were obtained from Charles River, Wilmington, Mass. Mice were group-housed 10 per cage. The body weight upon arrival was 20-25 g. Food and water were available ad libitum except during experiments Animals were acclimated to the animal facilities for a period of at least one week prior to commencement of experiments Animals were tested in the light phase of a 12-hour light: 12-hour dark schedule (lights on 0600 hours).

Compound A ([2-(2-Chloro-4-fluorophenoxy)-2-methyl-N-[(E)-5-(methylsulfonyl)-2-adamantyl]propanamide]) was synthesized at Abbott Laboratories. Compound A was administered via a drug-in-diet administration (100 mg/kg/day in Western diet) or (10 mg/kg/day in Western diet).

On the first day of testing (17 days after drug-in-diet was presented) mice were removed from the colony room in their home cage, brought to the testing room, and left undisturbed for 2 hours prior to testing initiation. Following this habituation period, drug-in-diet mice were tested. Upon testing initiation, mice were placed one at a time into the light (safe) compartment of a two-chambered apparatus (Gemini apparatus, San Diego Instruments, San Diego, Calif.), during which time the retractable door was closed. After 30 sec at the completion of the acclimation period the door between the light and dark compartments was opened. Measurement of the training latency commenced at this point. This measure (training) provides some indication of general locomotor activity. If a mouse has not crossed within 60 s the animal's data is excluded from the analysis. After the mouse crossed into the dark chamber the door was lowered and inescapable footshock (0.13 mA, 1 sec duration) was presented to the mouse after it completely entered the chamber and the door closed. The mouse was immediately removed from the chamber and returned to the home cage. 24-hours later the mouse was tested using methods identical to those on the training day, except without being dosed and without shock presentation. The latency to enter the dark chamber was recorded and was the dependent variable measured for assessing memory retention (latency is defined as entry of the whole mouse; all 4 paws on the grids in the dark side, plus the tail in the chamber for 5 sec; 180 sec is maximum latency). Data were analyzed using Mann Whitney U comparisons. P<0.05 was regarded as significant. As illustrated in FIG. 1, there was a significant improvement in memory retention following the administration of Compound A at both doses compared to the response of vehicle control mice.

Example 2

A Selective 11β-HSD1 Inhibitor Enhances Phosphorylated CREB, a Biochemical Marker of Cognitive Enhancement, in Mice After 2-Week Food-in-Diet Dosing In vivo signaling studies were conducted to examine the biochemical pathways that may be mechanistically involved in the cognitive efficacy associated with Compound A. An important signaling process that serves as a biochemical correlate of synaptic plasticity underlying learning and memory is the phosphorylation of CREB (c-AMP-response element binding protein), a transcription factor critical to long-term memory. To investigate the effects of Compound A on CREB phosphorylation, CD1 mice treated and tested (data presented in FIG. 1) were given a 24-hour rest after testing before immunohistochemical procedures commenced.

Male CD-1 mice were obtained from Charles River, Wilmington, Mass. Mice were group-housed 10 per cage. The body weight upon arrival was 20-25 g. Food and water were available ad libitum except during experiments Animals were acclimated to the animal facilities for a period of at least one week prior to commencement of experiments Animals were tested in the light phase of a 12-hour light: 12-hour dark schedule (lights on 0600 hours).

Figure 2:
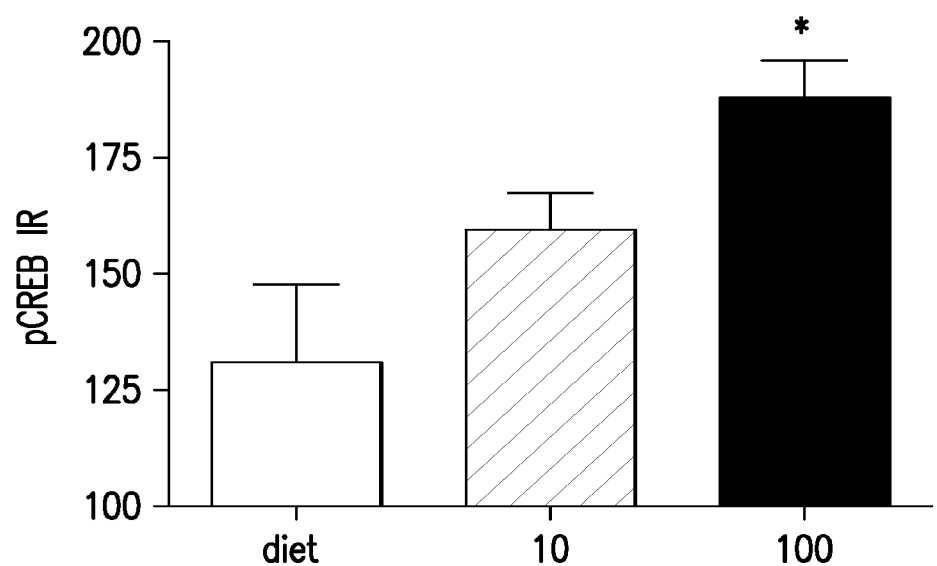
FIG. 2 depicts amount of phosphorylation of CREB in treated and untreated mice.

Compound A was administered via a drug-in-diet administration (100 mg/kg/day in Western diet) or (10 mg/kg/day in Western diet). 18-days after receiving Compound A food-in-diet (10 and 100 mg/kg/day) rats were anesthetized and perfused through the aorta with normal saline followed by 10% formalin. Following perfusion, brains were removed and postfixed in 20% sucrose-PBS (phosphate buffered saline) overnight and subsequently cut on a cryostat (40 µm coronal sections) and collected as free-floating sections in PBS. Sections were then immunostained for Fos protein using a 3-step ABC-peroxidase technique beginning with a 30-min incubation with blocking serum. Sections were next incubated with anti-phsopho-CREB (rabbit IgG, 1:1000, Cell signaling) antibodies for 48 hrs at 4 degrees C., washed with PBS and incubated for 1-hr with either biotinylated secondary anti-sheep or anti-mouse antibody (Ab) solution (1:200). Finally, sections were washed in PBS, incubated with ABC reagent (Vector) and then developed in a peroxidase substrate solution. The sections were mounted, coverslipped and examined and photographed with a light microscope (Leica, DMRB). Immuno-reactivity (IR) was quantified using an image analysis system (Leica, Quantimet 500) that determined number and/or area of peroxidase substrate-positive stained neurons from digitized photomicrographs according to a pixel gray level empirically determined prior to analysis. Overall statistical significance was determined using a one-way ANOVA, with Dunnett's post hoc analyses used to determine significance (p<0.05 was considered significant). FIG. 2 shows the increase in phosphorylated CREB following the administration of Compound A mg/kg/day.

Example 3

Selective 11β-HSD1 Inhibitors Enhance Memory Consolidation in Mice After Subchronic Dosing The 24-hour inhibitory avoidance model in mice was used to evaluate the effects of Compound A and Compound B ([N-{(E)-5-[(Z)-Amino(hydroxyimino)methyl]-2-adamantyl}-2-(4-chlorophenoxy)-2-methylpropanamide]) following a subchronic (3 administration) dosing regimen. Male CD-1 mice were obtained from Charles River, Wilmington, Mass. Mice were group-housed 10 per cage. The body weight upon arrival was 20-25 g. Food and water were available ad libitum except during experiments Animals were acclimated to the animal facilities for a period of at least one week prior to commencement of experiments Animals were tested in the light phase of a 12-hour light: 12-hour dark schedule (lights on 0600 hours).

Compound A and Compound B were synthesized at Abbott Laboratories. Compounds A and B were solubilized in a solution of 5% Tween80 water. Compound A was administered in a cloudy, fine suspension, while Compound B was administered in a solution.

Mice were weighed and dosed BID (≈8 AM and 3 PM) PO with Compound A (30 mg/kg), or Compound B (30 mg/kg) or vehicle the day before training. On training day, mice were injected with Compound A, Compound B or vehicle one-hour PO before training. One hour following injection (start of training) mice were subjected to a training session in which they were placed in a lighted compartment of a two-compartment chamber (Gemini apparatus, San Diego Instruments, San Diego, Calif.) with a manually operated gate separating the compartments. Following a 30 second habituation period in the lighted compartment, the door to the adjacent dark compartment was opened. Once the mouse had completely transferred, the door was closed and a 0.13 mA current was applied to the grid floor for 1 s. The mouse was then immediately removed and returned to the home cage. Twenty-four hours later mice were again tested in the same apparatus, except without shock, and the transfer latency from the lighted to the dark compartment recorded and used as an index of memory for the punished response 24 hours earlier. The electric shock parameters of this test were established such that vehicle treated mice would only have minimal retention of the conditioning trial, thus allowing a large window for improvement of the memory following drug treatment. Data were analyzed using Mann Whitney U comparisons. P<0.05 was regarded as significant.

Figure 3:
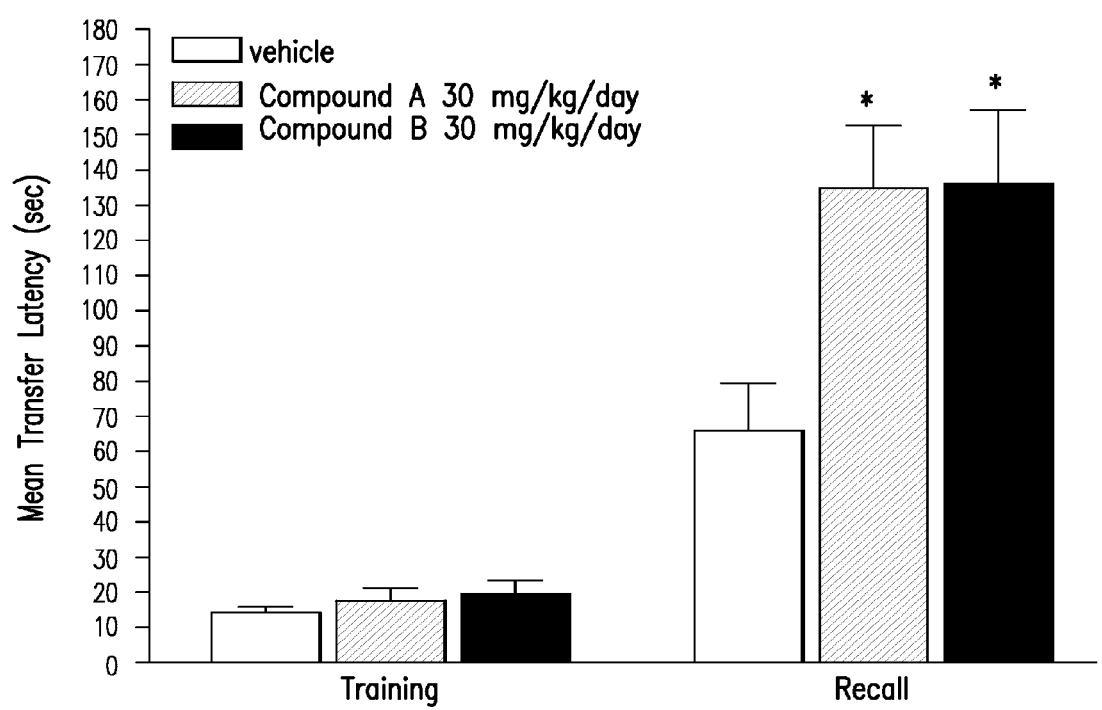
FIG. 3 shows the results of memory consolidation in treated and untreated mice measured as Mean Transfer Latency.

As illustrated in FIG. 3, there was a significant improvement in memory retention following the administration of both Compounds A and B compared to the response of vehicle control mice.

Example 4

A Selective 11β-HSD1 Inhibitor Enhances Short-Term Memory in Rats After Subchronic Dosing Social memory and social cognition are impaired in disorders such as Alzheimer's disease and schizophrenia. One of the more commonly used preclinical models of social recognition memory is short-term social recognition in the rat, a model of short-term memory based on the recognition of a juvenile rat by an adult rat. When adult rats are allowed to interact with a juvenile rat for 5 min, the adult exhibits behaviors such as close following, grooming or sniffing the juvenile for as much as 40-50% of the duration of a 5 min trial. The juvenile rat is then removed and reintroduced 120 min later, and interactive behavior of the adult rat is again monitored. If memory has been lost over the interval between trials 1 and 2, the extent of interaction is equal (expressed as a ratio of investigation time of T1/T2) and the ratio will be close to 1. However, if the adult remembers the juvenile, the investigation ratio declines. To test for non-specific effects, a novel juvenile is introduced at 120 minutes instead of the familiar juvenile. If the ratio is less than 1, this indicates the drug is having effects that may not be specific to cognition.

Male Sprague Dawley rats from Charles Rivers (Portage, Mich., USA) were used. Adults weighed 370-500 g, and juveniles weighed 70-120 g at the time of testing. All animals were housed in a quiet room under conditions of 12 h lights on/12 h lights off (on at 06:00 am) in groups of four with food and water available ad libitum. Studies were conducted between 08:00 h and 16:00 h, and treatment groups were arranged for equal representation of time of day. Compound C ([N-[(E)-5-Hydroxy-2-adamantyl]-2-{4-[5-(trifluoromethyppyridin-2-yl]piperazin-1-yl}acetamide], 30 mg/kg) was dissolved in PEG 400 using a warm sonicator bath. Compound was administered in solution in a volume of 1 mL/1 g body weight, p.o.

Rats were pre-dosed po at 24, 18 and 1 hour before first juvenile rat exposure with vehicle, or Compound C (30 mg/kg). During testing, the adult rat was placed into the test cage. After 30 min, a juvenile rat was placed into the test cage with the adult rat for 5 min. The time the adult spent exploring (sniffing, grooming, close following) the juvenile during this test session was recorded, and defined as the first investigation duration. The juvenile was then removed from the test cage, and placed into its borne cage. Following a further 90 min, the adult was placed back into the same test chamber, for a second 30-min habituation. Following this second habituation the same juvenile (familiar) was again placed into the test cage for a 5-min test session; the time spent exploring the juvenile during this test session was defined as the second investigation duration. Vehicle treated rats do not remember the familiar juvenile following this two hr delay. Data were analyzed using a one-way analysis of variance. If there was a significant effect, subsequent post hoc significance was determined using Dunnett's multiple comparison testing (p<0.05 was regarded as significant).

Figure 4:
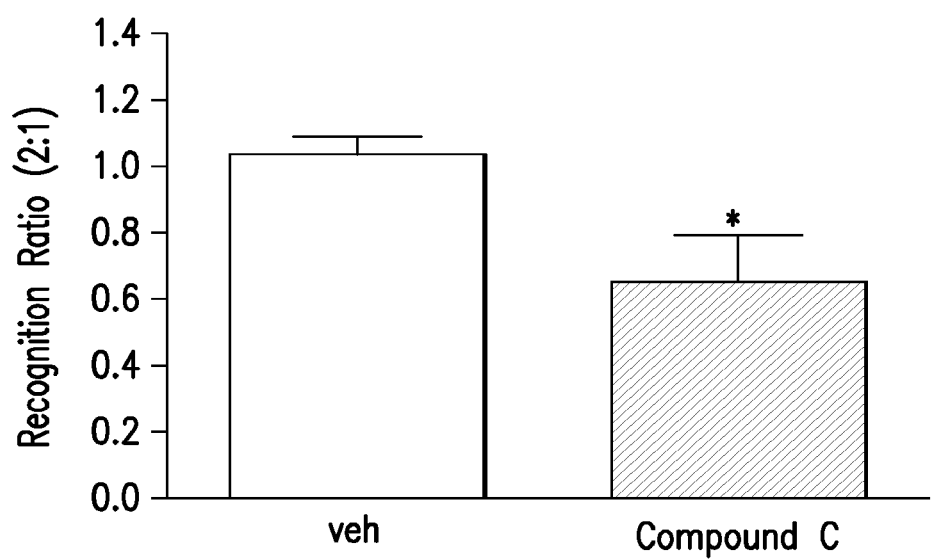
FIG. 4 shows the results of short memory retention in treated and untreated mice measured as Mean Transfer Latency.

As shown in FIG. 4, there was a significant improvement in short-term memory retention following the administration of Compound C compared to the response of vehicle control rats.

Example 5

Figure 5A:
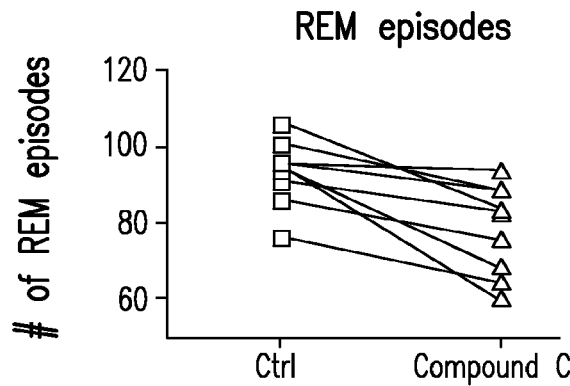
FIGS. 5a-5c show REM episodes, time and latency to first episode, respectively, on rat treated with an exemplary 11β-HSD-1 inhibitor.
Figure 5B:
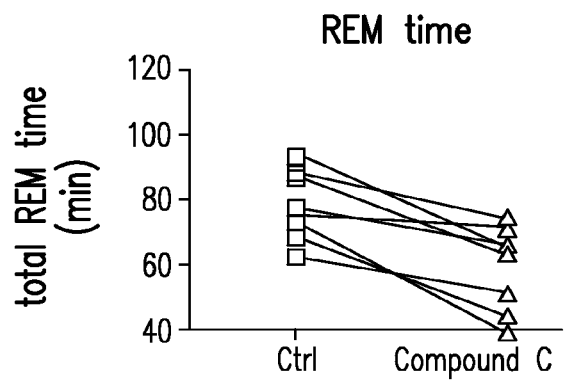
Figure 5C:
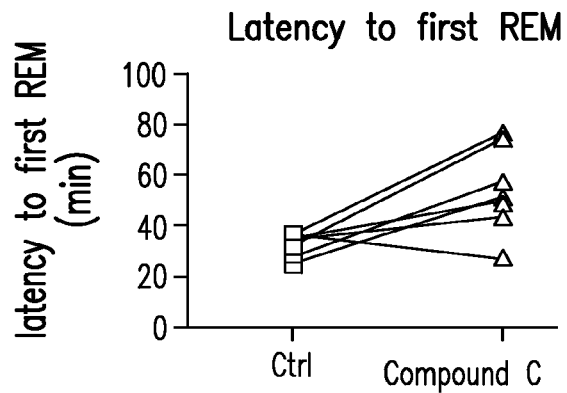

Effects of 11βHSD-1 Inhibitor on Rat Wake EEG Power Spektrum and REM Sleep Parameter EEG of Fisher rats (n=8/group) with chronically implanted supracortical EEG-electrodes were analyzed for an 8 h period. Intraindividual drug-induced changes of power spectra were analyzed. For REM sleep the number of REM episodes, latency to first REM, and total REM time was analyzed. Compound C (30 mg/kg; 3 times at 24, 26, and 0.1 hours before measurement) significantly reduced the number of REM sleep episodes by 16% (total sleep time by 10%); the corresponding REM time was reduced by 23%. The latency to first REM significantly increased by 62% (See FIGS. 5a, 5b and 5c, respectively).

The observed effects on REM were in line with the effects of antidepressants like SSRIs and TCAs. These effects differ from the procognitive effects induced by inhibitors of ACh-esteras like donepezil and physostigmine.

Example 6

Modulation of Cortical/Hippocampal Acetylcholine Serotonin Release by 11β-HSD1 Inhibition Microdialysis studies (resting or challenging conditions) in freely moving, male Sprague Dawley rats (Janvier, 295-315 g, n=5-8 treatment group) were performed using stereotactically instrumented microdialysis probes (CMA/12-14-2): mPFC, hippocampus. Aliquots of the same microdialysate fractions (6 before, and 9-12 after compound administration) were analyzed either for acetylcholine or for serotonin by HPLC and electrochemical detection.

Microdialysate Acetylcholine Levels

Figure 6A:
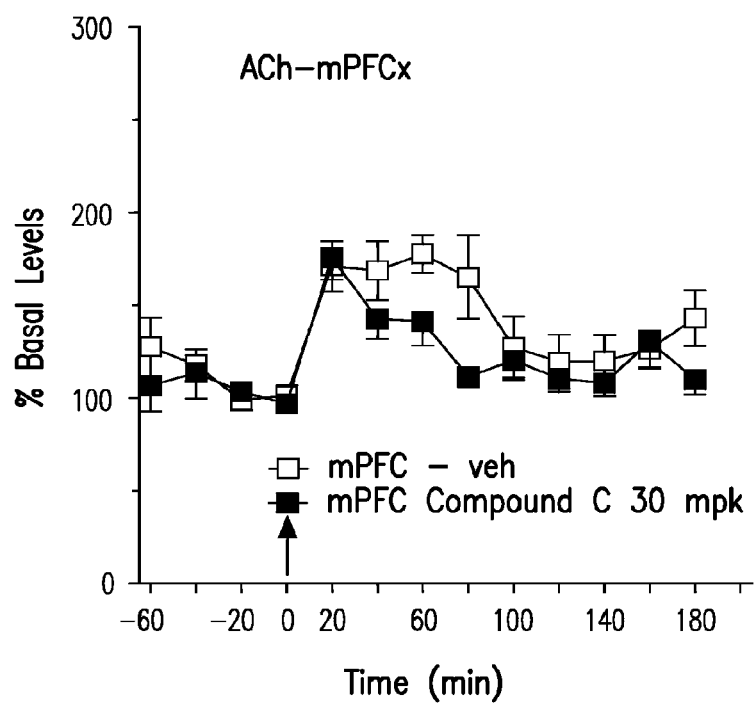
FIGS. 6a, 6b and 6c show the effects of an exemplary 11β-HSD-1 inhibitor on cortical and hippocampal Ach release.
Figure 6B:
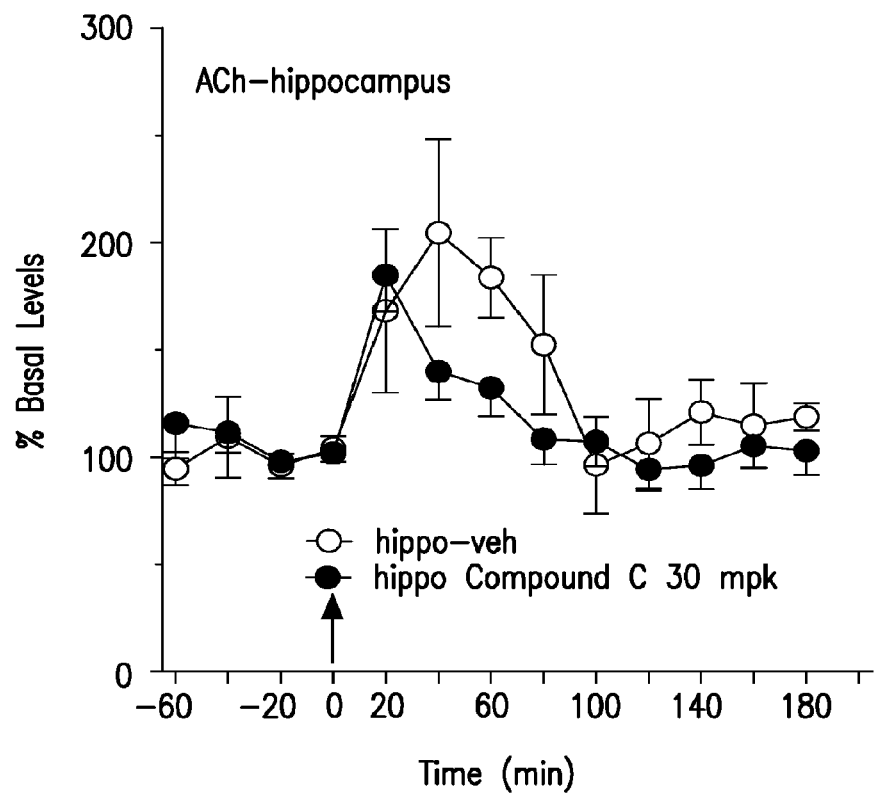
Figure 6C:
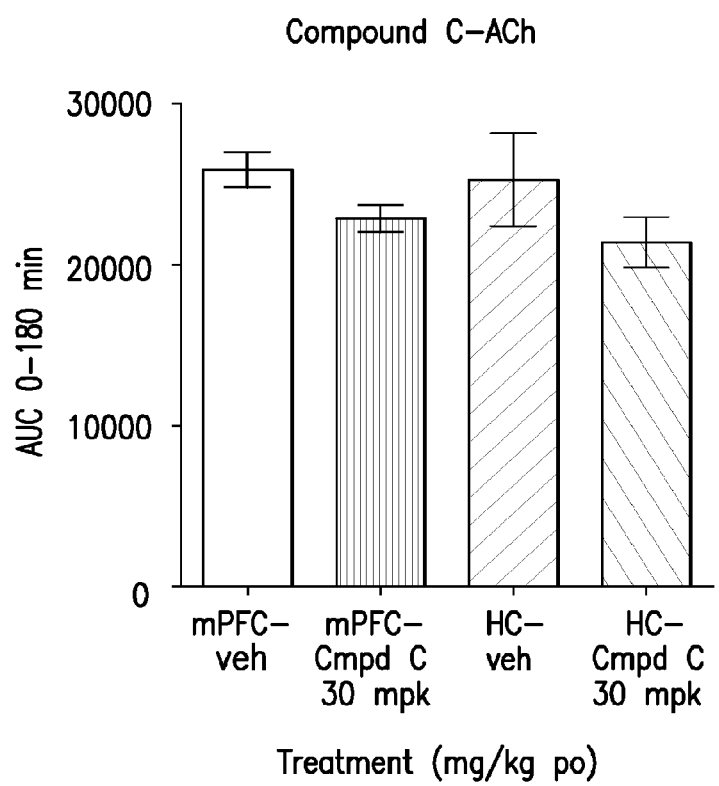
Figure 7A:
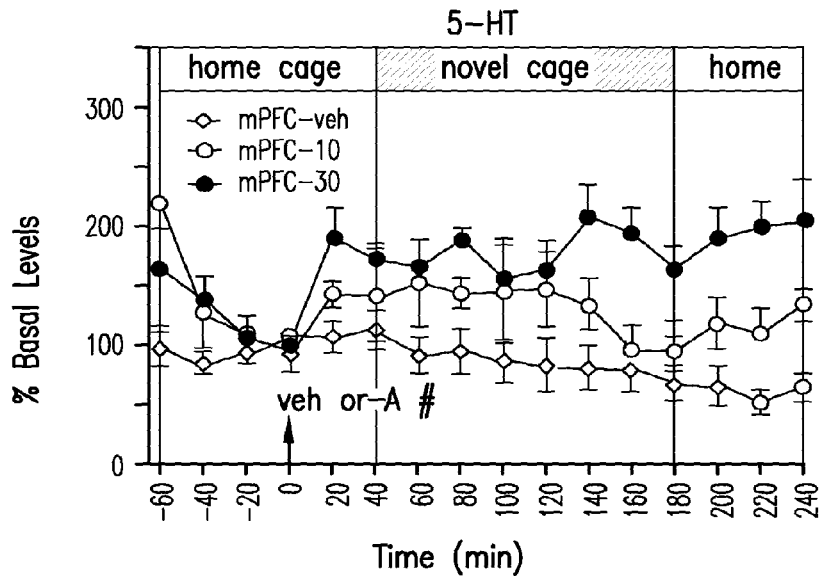
FIGS. 7a and 7b show the effects of an exemplary 11β-HSD-1 inhibitor on cortical and hippocampal 5-HT release.
Figure 7B:
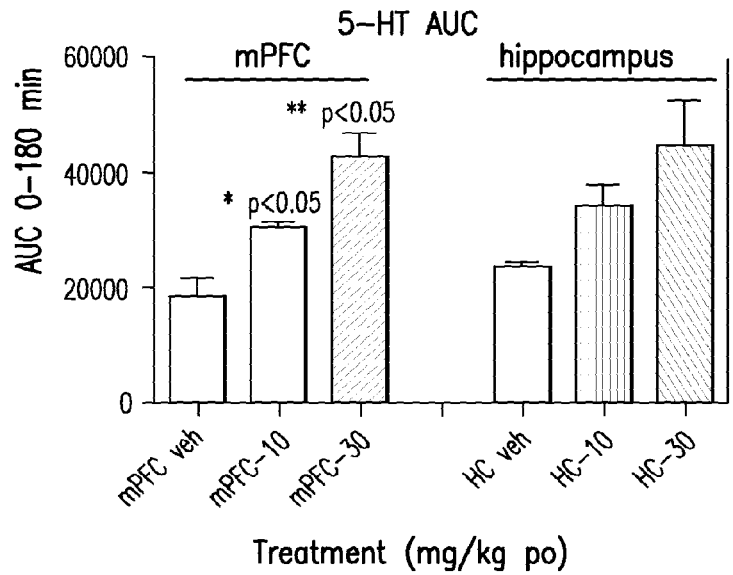

Acute, single administration of Compound C (30 mg/kg, p.o.) did not change ACh release under resting conditions. Challeging conditions as the transfer from home cage to novel cage, and back to home cage resulted in stimulation of ACh release (see FIGS. 6a, 6b and 6c). Single administration of Compound C did not induce any further stimulation of ACh release, neither in the cortex nor in the hippocampus.

B. Microdialysate Serotonin Levels

Single administration of Compound C (30 mg/kg, p.o.) resulted in a long-lasting increase of serotonin (5-HT) levels in the medial prefrontal cortex and in the hippocampus. This is a feature shared by marketed anti-depressive drugs and might indicate the potential use for 11β-HSD1 inhibitors as antidepressants/anxiolytic drugs. These findings remain to be confirmed by (i) investigating 11β-HSD1 inhibitors from different chemotype(s) in selected microdialysis studies and/or (ii) in animal models of depression/anxiety. Additionally, these results differentiate 11β-HSD-1 inhibition from acetylcholine esterase inhibition, the current therapeutic principle for symptomatic treatment of Alzheimer's disease.

What is claimed is:

1. A method for treating a patient suffering from a glucocorticoid-related central nervous system disorder, comprising administering to the patient an effective amount of a selective inhibitor of 11-beta-hydroxysteroid dehydrogenase Type 1 enzyme activity, wherein the disorder is selected from the group consisting of Alzheimer's disease, decline in cognitive function in Alzheimer's disease and associated dementias, cognitive deficits associated with aging and neurodegeneration, dementia, senile dementia, AIDS dementia, depression, anxiety, panic disorder, post traumatic stress disorder, steroid-induced acute psychosis, cognitive deficits associated with diabetes, attention deficit disorder in general, attention deficit hyperactivity disorder (ADHD), mild cognitive impairment, and schizophrenia, and wherein the inhibitor is a compound of formula (IV)

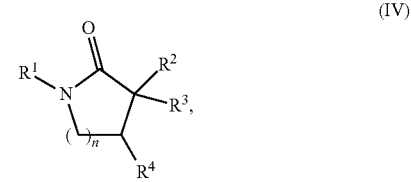

wherein:
n is 2;
R$^1$ is

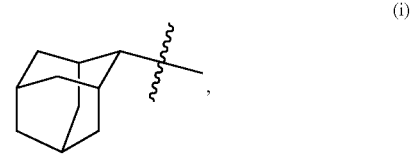

-continued

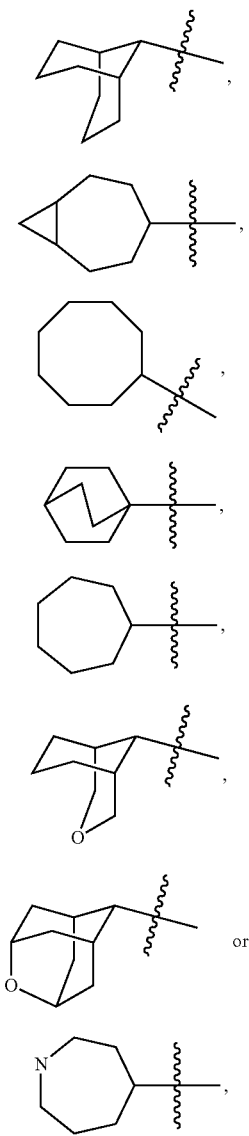

each of which is independently unsubstituted or substituted with 1 or 2 substituents independently selected from the group consisting of alkyl, alkenyl, haloalkyl, Cl, Br, F, I, —CN, —NO$_2$, —OR$_b$, —SR$_b$, —S(O)R$_2$, —S(O)$_2$R$_2$, —NR$_a$R$_b$, —C(O)R$_b$, —C(O)OR$_b$, —C(O)NR$_a$R$_b$, —S(O)$_2$NR$_a$R$_b$, —C(=NOH)NH$_2$, —C(=NH)NH$_2$, R$_c$, —(CR$_d$R$_e$)$_m$—CN, —(CR$_d$R$_e$)$_m$—OR$_b$, —(CR$_d$R$_e$)$_m$—SR$_b$, —(CR$_d$R$_e$)$_m$—S(O)$_2$R$_Z$, —(CR$_d$R$_e$)$_m$—NR$_a$R$_b$, —(CR$_d$R$_e$)$_m$—C(O)R$_b$, —(CR$_d$R$_e$)$_m$—C(O)OR$_b$, —(CR$_d$R$_e$)$_m$—S(O)$_2$NR$_a$R$_b$, —(CR$_d$R$_e$)$_m$—R$_c$, —N(R$_a$)—(CR$_d$R$_e$)$_m$—C(O)R$_b$, —N(R$_a$)—(CR$_d$R$_e$)$_m$—C(O)O R$_b$, —N(R$_a$)—(CR$_d$R$_e$)$_m$—C(O)NR$_a$R$_b$, —O—(CR$_d$R$_e$)$_m$—C(O)R$_b$, —O—(CR$_d$R$_e$)$_m$—C(O)OR$_b$, and —O—(CR$_d$R$_e$)$_m$—C(O)NR$_a$R$_b$;

R$^2$ and R$^3$, at each occurrence, are each independently hydrogen or alkyl;

R$^4$ is —(CR$_d$R$_e$)$_m$-E-G, wherein E, at each occurrence, is independently O, or N(R$_e$), and G, at each occurrence, is independently phenyl or pyridinyl, wherein each G is independently unsubstituted or substituted with 1 or 2 substituents independently selected from the group consisting of alkyl, alkenyl, haloalkyl, Cl, Br, F, I, —CN, —NO$_2$, —OR$_d$, —S(R$_d$), —S(O)(alkyl), —S(O)(haloalkyl), —S(O)$_2$ (alkyl), —S(O)$_2$ (haloalkyl), —NR$_d$R$_e$, —C(O)(R$_d$), —C(O)OR$_d$, —C(O)NR$_d$R$_e$, —S(O)$_2$NR$_d$R$_e$, R$_c$, —(CR$_d$R$_e$)$_m$—CN, —(CR$_d$R$_e$)$_m$—NO$_2$, —(CR$_d$R$_e$)$_m$—OR$_d$, —(CR$_d$R$_e$)$_m$—S(R$_d$), —(CR$_d$R$_e$)$_m$—S(O)(alkyl), —(CR$_d$R$_e$)$_m$—S(O)(haloalkyl), —(CR$_d$R$_e$)$_m$—S(O)$_2$(alkyl), —(CR$_d$R$_e$)$_m$—S(O)$_2$ (haloalkyl), —(CR$_d$R$_e$)$_m$—NR$_d$R$_e$, —(CR$_d$R$_e$)$_m$—C(O)(R$_d$), —(CR$_d$R$_e$)$_m$—C(O)OR$_d$, —(CR$_d$R$_e$)$_m$—C(O)NR$_d$R$_e$, —(CR$_d$R$_e$)$_m$—S(O)$_2$NR$_d$R$_e$, and —(CR$_d$R$_e$)$_m$—R$_c$;

R$_a$, at each occurrence, is independently hydrogen or alkyl;

R$_b$, at each occurrence, is independently hydrogen, alkyl, haloalkyl, R$_c$ or —(CR$_d$R$_e$)$_m$—R$_c$;

R$_Z$, at each occurrence, is independently alkyl, haloalkyl, R$_c$, or —(CR$_d$R$_e$)$_m$—R$_c$;

R$_c$ at each occurrence, is independently aryl, heteroaryl, cycloalkyl or heterocycle; wherein each R$_c$ is independently unsubstituted or substituted with 1, 2, 3 or 4 substituents independently selected from the group consisting of alkyl, alkenyl, haloalkyl, Cl, Br, F, I, —CN, —NO$_2$, —OR$_d$, —S(R$_d$), —S(O) (alkyl), —S(O)(haloalkyl), —S(O)$_2$(alkyl), —S(O)$_2$ (haloalkyl), —NR$_d$R$_e$, —C(O)(R$_d$), —C(O)OR$_d$, —C(O)NR$_d$R$_e$, —S(O)$_2$NR$_d$R$_e$, —(CR$_d$R$_e$)$_m$—CN, —(CR$_d$R$_e$)$_m$—NO$_2$, —(CR$_d$R$_e$)$_m$—OR$_d$, —(CR$_d$R$_e$)$_m$—S(R$_d$), —(CR$_d$R$_e$)$_m$—S(O)(alkyl), —(CR$_d$R$_e$)$_m$—S(O)(haloalkyl), —(CR$_d$R$_e$)$_m$—S(O)$_2$(alkyl), —(CR$_d$R$_e$)$_m$—S(O)$_2$(haloalkyl), —(CR$_d$R$_e$)$_m$—NR$_d$R$_e$, —(CR$_d$R$_e$)$_m$—C(O)(R$_d$), —(CR$_d$R$_e$)$_m$—C(O)OR$_d$, —(CR$_d$R$_e$)$_m$—C(O)NR$_d$R$_e$, and —(CR$_d$R$_e$)$_m$—S(O)$_2$NR$_d$R$_e$;

R$_d$ and R$_e$, at each occurrence, are independently hydrogen or alkyl; and m is 1;

or a pharmaceutically acceptable salt thereof, or a combination thereof.

2. The method of claim 1, wherein the disorder is Alzheimer's disease.

3. The method of claim 1, wherein the disorder is depression.

4. The method of claim 2, wherein depression is major depressive disorder, psychotic depression, depression in Cushing's syndrome or treatment resistant depression.

5. The method of claim 1, wherein the disorder is anxiety.

6. The method of claim 1, wherein the disorder is panic disorder.

7. The method of claim 1, wherein the disorder is post traumatic stress disorder.

8. The method of claim 1, wherein the disorder is steroid-induced acute psychosis.

9. The method of claim 1, wherein the disorder is cognitive deficits associated with diabetes.

10. The method of claim 1, wherein the disorder is attention deficit hyperactivity disorder (ADHD).

11. The method of claim 1, wherein the disorder is schizophrenia.

* * * * *

UNITED STATES PATENT AND TRADEMARK OFFICE
CERTIFICATE OF CORRECTION

PATENT NO. : 9,464,072 B2
APPLICATION NO. : 14/569203
DATED : October 11, 2016
INVENTOR(S) : Bitner et al.

It is certified that error appears in the above-identified patent and that said Letters Patent is hereby corrected as shown below:

In the Claims

Column No: 39, Line(s): 50 Claim: 1, "-S(O)R$_2$" to read as --S(O)R$_Z$--
Column No: 39, Line(s): 51 Claim: 1, "-S(O)$_2$R$_2$" to read as --S(O)$_2$R$_Z$--

Signed and Sealed this
Tenth Day of July, 2018

Andrei Iancu
*Director of the United States Patent and Trademark Office*